United States Patent
Utsumi et al.

(10) Patent No.: US 9,097,969 B2
(45) Date of Patent: Aug. 4, 2015

(54) COMPOUND, RESIST COMPOSITION AND METHOD OF FORMING RESIST PATTERN

(71) Applicant: Tokyo Ohka Kogyo Co., Ltd., Kawasaki-shi (JP)

(72) Inventors: Yoshiyuki Utsumi, Kawasaki (JP); Hideto Nito, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 13/914,903

(22) Filed: Jun. 11, 2013

(65) Prior Publication Data
US 2013/0337382 A1  Dec. 19, 2013

(30) Foreign Application Priority Data

Jun. 13, 2012 (JP) .................... 2012-134177
Oct. 26, 2012 (JP) .................... 2012-237236

(51) Int. Cl.
| | | |
|---|---|---|
| G03F 7/023 | (2006.01) | |
| G03F 7/30 | (2006.01) | |
| C07C 245/12 | (2006.01) | |
| C07C 303/32 | (2006.01) | |
| C07C 309/04 | (2006.01) | |
| C07C 309/06 | (2006.01) | |
| C07C 309/12 | (2006.01) | |
| C07C 309/19 | (2006.01) | |
| C07D 333/46 | (2006.01) | |
| C07D 335/02 | (2006.01) | |

(52) U.S. Cl.
CPC .............. *G03F 7/023* (2013.01); *C07C 245/12* (2013.01); *C07D 333/46* (2013.01); *C07D 335/02* (2013.01); *G03F 7/0233* (2013.01); *C07C 303/32* (2013.01); *C07C 309/04* (2013.01); *C07C 309/06* (2013.01); *C07C 309/12* (2013.01); *C07C 309/19* (2013.01); *G03F 7/30* (2013.01)

(58) Field of Classification Search
CPC ......... G03F 7/023; G03F 7/0233; G03F 7/30; C07C 303/32; C07C 309/04; C07C 309/06; C07C 309/12; C07C 309/19; C07C 245/12; C07D 333/46; C07D 335/02; C07D 245/12
USPC ......... 430/191, 192, 193, 919, 920, 921, 922; 534/556, 557; 562/100, 109, 113; 568/77; 549/13, 28, 29, 78
See application file for complete search history.

(56) References Cited

U.S. PATENT DOCUMENTS

| | | | |
|---|---|---|---|
| 5,609,982 A * | 3/1997 | Sato et al. ................. | 430/192 |
| 6,949,325 B2 | 9/2005 | Li et al. | |
| 2001/0049073 A1 | 12/2001 | Hada et al. | |
| 2004/0110085 A1 | 6/2004 | Iwai et al. | |
| 2007/0231708 A1 | 10/2007 | Matsumaru et al. | |
| 2009/0197204 A1 | 8/2009 | Shiono et al. | |
| 2009/0317743 A1 | 12/2009 | Shiono et al. | |
| 2010/0310985 A1 | 12/2010 | Mori et al. | |
| 2011/0117499 A1 | 5/2011 | Matsumiya et al. | |

FOREIGN PATENT DOCUMENTS

| | | |
|---|---|---|
| JP | A-2000-206694 | 7/2000 |
| JP | A-2003-241385 | 8/2003 |
| JP | A-2005-336452 | 12/2005 |
| JP | A-2006-045311 | 2/2006 |
| JP | A-2006-259582 | 9/2006 |
| JP | A-2006-317803 | 11/2006 |
| JP | A-2009-025723 | 2/2009 |
| JP | A-2010-002870 | 1/2010 |
| JP | A-2010-032994 | 2/2010 |
| JP | A-2010-277043 | 12/2010 |
| JP | A-2011-013569 | 1/2011 |
| JP | A-2011-128226 | 6/2011 |

* cited by examiner

*Primary Examiner* — John Chu
(74) *Attorney, Agent, or Firm* — Knobbe Martens Olson & Bear LLP

(57) ABSTRACT

A compound represented by general formula (b1) shown below (in the formula, $Y^1$ represents a divalent linking group; W represents S, Se or I; $R^1$ represents a hydrocarbon group; represents an alkyl group of 1 to 5 carbon atoms or an alkoxy group of 1 to 5 carbon atoms; when W represents I, m+n=2, and when W represents S or Se, m+n=3, provided that m≥1 and n≥0; p represents an integer of 0 to 5; and $X^-$ represents a counteranion.

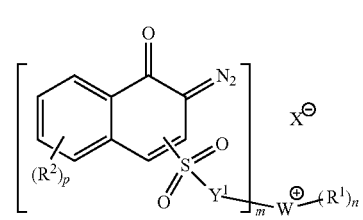

(b1)

19 Claims, No Drawings

COMPOUND, RESIST COMPOSITION AND METHOD OF FORMING RESIST PATTERN

TECHNICAL FIELD

The present invention relates to a compound which is useful for acid generation in a resist composition, a resist composition containing the compound, and a method for forming a resist pattern using the resist composition.

Priority is claimed on Japanese Patent Application No. 2012-134177, filed Jun. 13, 2012, and Japanese Patent Application No. 2012-237236, filed Oct. 26, 2012, the contents of which are incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter (energy higher) than these excimer lasers, such as electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified composition is used, which includes a base material component that exhibits a changed solubility in a developing solution under the action of acid and an acid-generator component that generates acid upon exposure. For example, in the case where the developing solution is an alkali developing solution (alkali developing process), a chemically amplified positive resist which contains, as a base component (base resin), a resin which exhibits increased solubility in an alkali developing solution under action of acid, and an acid generator is typically used. If a resist film formed using such a resist composition is selectively exposed at the time of forming a resist pattern, in exposed areas, an acid is generated from the acid generator component, and the polarity of the base resin increases by the action of the generated acid, thereby making the exposed areas soluble in the alkali developing solution. Thus, by conducting alkali developing, the unexposed portions remain to form a positive resist pattern. On the other hand, in the case of applying a solvent developing process using a developing solution containing an organic solvent (organic developing solution), when the polarity of the base resin increases, the solubility in the organic developing solution is relatively decreased. Therefore, unexposed areas of the resist film are dissolved in and removed by the organic developing solution, whereby a negative-type resist pattern in which exposed areas remain as a pattern is formed. Such a solvent developing process for forming a negative-tone resist composition is sometimes referred to as "negative-tone developing process" (for example, see Patent Document 1).

Currently, resins that contain structural units derived from (meth)acrylate esters within the main chain (acrylic resins) are now widely used as base resins for resist compositions that use ArF excimer laser lithography, as they exhibit excellent transparency in the vicinity of 193 nm (for example, see Patent Document 2).

On the other hand, as acid generators usable in a chemically amplified resist composition, various types have been proposed including, for example, onium salt acid generators; oxime sulfonate acid generators; diazomethane acid generators; nitrobenzylsulfonate acid generators; iminosulfonate acid generators; and disulfone acid generators. In recent years, base resins that include a structural unit which functions as an acid generator have also been used (see for example, Patent Document 3).

DOCUMENTS OF RELATED ART

Patent Document

[Patent Document 1] Japanese Unexamined Patent Application, First Publication No. 2009-025723
[Patent Document 2] Japanese Unexamined Patent Application, First Publication No. 2003-241385
[Patent Document 3] Japanese Unexamined Patent Application, First Publication No. 2006-045311

SUMMARY OF THE INVENTION

As further progress is made in lithography techniques and miniaturization of resist patterns, further improvements in resist materials have been demanded in terms of various lithography properties such as LWR, MEEF, and EL margin, and a resist pattern shape.

However, in the case of using conventional acid generators or constituent units having acid-generating ability as those disclosed in Patent Documents 2 and 3, there was still room for improvements in lithography properties and the resist pattern shape.

The present invention takes the above circumstances into consideration, with an object of providing a compound which is useful for acid generation in a resist composition, a resist composition containing the compound, and a method for forming a resist pattern using the resist composition.

For solving the above-mentioned problems, the present invention employs the following aspects.

Specifically, a first aspect of the present invention is a compound represented by general formula (b1) shown below.

[Chemical Formula 1]

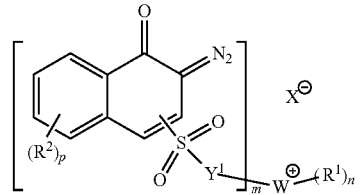

In the formula, $Y^1$ represents a divalent linking group; W represents S, Se or I; $R^1$ represents a hydrocarbon group which may have a substituent; R² represents an alkyl group of 1 to 5 carbon atoms or an alkoxy group of 1 to 5 carbon atoms; when W represents I, m+n=2, and when W represents S or Se, m+n=3, provided that m≥1 and n≥0; p represents an integer of 0 to 5; and X⁻ represents a counteranion.

A second aspect of the present invention is a resist composition including a base component (A) which exhibits changed solubility in an alkali developing solution under action of acid and an acid generator component (B) which generates acid upon exposure, the acid generator component (B) including an acid generator (B1) containing a compound represented by general formula (b1-1) shown below.

[Chemical Formula 2]

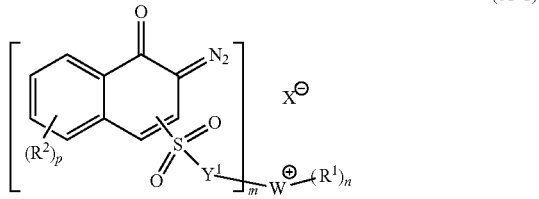

(b1-1)

In the formula, Y¹ represents a divalent linking group; W represents S, Se or I; R¹ represents a hydrocarbon group which may have a substituent; R² represents an alkyl group of 1 to 5 carbon atoms or an alkoxy group of 1 to 5 carbon atoms; when W represents I, m+n=2, and when W represents S or Se, m+n=3, provided that m≥1 and n≥0; p represents an integer of 0 to 5; and X⁻ represents a counteranion.

A third aspect of the present invention is a method of forming a resist pattern, including: using a resist composition according to the second aspect to form a resist film on a substrate, subjecting the resist film to exposure, and subjecting the resist film to developing to form a resist pattern.

The present invention is able to provide a compound which is useful for acid generation in a resist composition. Furthermore, the present invention is able to provide a resist composition containing the compound according to the present invention, which is excellent in terms of various lithography properties such as LWR, MEEF, and EL margin, and a resist pattern shape, and a method for forming a resist pattern using the resist composition.

MODE FOR CARRYING OUT THE INVENTION

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified.

The term "alkylene group" includes linear, branched or cyclic, divalent saturated hydrocarbon, unless otherwise specified. The same applies for the alkyl group within an alkoxy group.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with fluorine atom(s).

The term "structural unit" refers to a monomer unit that contributes to the formation of a polymeric compound (resin, polymer, copolymer).

A "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid (CH₂=CH—COOH) has been substituted with an organic group.

The acrylate ester may have the hydrogen atom bonded to the carbon atom on the α-position substituted with a substituent. The substituent (Rᵅ) with which the hydrogen atom bonded to the carbon atom at the α-position is substituted is an atom other than the hydrogen atom or a group, and examples thereof include an alkyl group having from 1 to 5 carbon atoms, a halogenated alkyl group having from 1 to 5 carbon atoms, and a hydroxyalkyl group. A carbon atom on the α-position of an acrylate ester refers to the carbon atom bonded to the carbonyl group, unless specified otherwise.

Hereafter, an acrylate ester having the hydrogen atom bonded to the carbon atom on the α-position substituted with a substituent is sometimes referred to as "α-substituted acrylate ester". Further, acrylate esters and α-substituted acrylate esters are collectively referred to as "(α-substituted) acrylate ester".

A "structural unit derived from hydroxystyrene or a hydroxystyrene derivative" refers to a structural unit that is formed by the cleavage of the ethylenic double bond of hydroxystyrene or a hydroxystyrene derivative.

The term "hydroxystyrene derivative" includes compounds in which the hydrogen atom at the α-position of hydroxystyrene has been substituted with another substituent such as an alkyl group or a halogenated alkyl group; and derivatives thereof. Examples of the derivatives thereof include hydroxystyrene in which the hydrogen atom of the hydroxy group has been substituted with an organic group and may have the hydrogen atom on the α-position substituted with a substituent; and hydroxystyrene which has a substituent other than a hydroxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

As the substituent which substitutes the hydrogen atom on the α-position of hydroxystyrene, the same substituents as those described above for the substituent on the α-position of the aforementioned α-substituted acrylate ester can be mentioned.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include benzoic acid in which the hydrogen atom of the carboxy group has been substituted with an organic group and may have the hydrogen atom on the α-position substituted with a substituent; and benzoic acid which has a substituent other than a hydroxy group and a carboxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

The term "styrene" is a concept including styrene and compounds in which the hydrogen atom at the α-position of styrene is substituted with other substituent such as an alkyl group and a halogenated alkyl group.

A "structural unit derived from styrene" or "structural unit derived from a styrene derivative" refers to a structural unit that is formed by the cleavage of the ethylenic double bond of styrene or a styrene derivative.

As the alkyl group as a substituent on the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group as the substituent on the α-position include groups in which part or all of the hydrogen atoms of the aforementioned "alkyl group as the substituent on the α-position" are substituted with halogen atoms. Examples of the halogen atom include a fluorine atom, a chlorine atom, a bromine atom and an iodine atom, and a fluorine atom is particularly desirable.

Specific examples of the hydroxyalkyl group of 1 to 5 carbon atoms as the substituent on the α-position include groups in which part or all of the hydrogen atoms of the aforementioned "alkyl group as the substituent on the α-position" are substituted with a hydroxy group. The number of hydroxy groups within the hydroxyalkyl group is preferably 1 to 5, and most preferably 1.

The case of describing "may have a substituent" includes both of the case where the hydrogen atom (—H) is substituted with a monovalent group and the case where the methylene group (—CH$_2$—) is substituted with a divalent group.

The term "exposure" is used as a general concept that includes irradiation with any form of radiation.

An "organic group" refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

<<Compound (b1)>>

A first aspect of the present invention is a compound represented by general formula (b1) shown below.

[Chemical Formula 3]

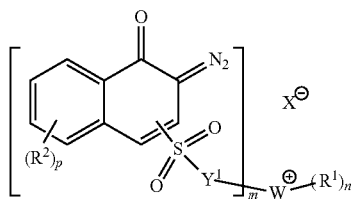

(b1)

In the formula, $Y^1$ represents a divalent linking group; W represents S, Se or I; $R^1$ represents a hydrocarbon group which may have a substituent; $R^2$ represents an alkyl group of 1 to 5 carbon atoms or an alkoxy group of 1 to 5 carbon atoms; when W represents I, m+n=2, and when W represents S or Se, m+n=3, provided that m≥1 and n≥0; p represents an integer of 0 to 5; and $X^-$ represents a counteranion.

In general formula (b1), $Y^1$ represents a divalent linking group. The divalent linking group for $Y^1$ is not particularly limited, and examples thereof include the same divalent linking groups as those defined for the structural unit (a2) described later which may have a substituent, and divalent linking groups which may have a hetero atom. Among these examples, divalent linking groups represented by general formulae (Y-lg-1) to (Y-lg-14) shown below are preferable. In general formulae (Y-lg-1) to (Y-lg-14), * represents a valence bond. The valence bond on the left-hand side is bonded to $SO_2$ in general formula (b1), and the valence bond on the right-hand side is bonded to $W^+$ in general formula (b1).

[Chemical Formula 4]

(Y-lg-1)

(Y-lg-2)

(Y-lg-3)

(Y-lg-4)

(Y-lg-5)

(Y-lg-6)

(Y-lg-7)

(Y-lg-8)

(Y-lg-9)

(Y-lg-10)

(Y-lg-11)

(Y-lg-12)

(Y-lg-13)

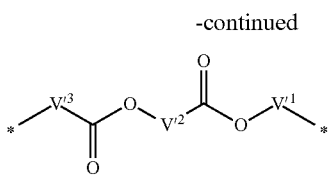
(Y-lg-14)

In the formulae, $V'^1$ to $V'^3$ each independently represents a divalent hydrocarbon group which may have a substituent; $V'^4$ represents a divalent hydrocarbon group which may have a substituent; and $R'^1$ a hydrogen atom or an alkyl group of 1 to 5 carbon atoms.

In formulae (Y-lg-1) to (Y-lg-14), $V'^1$ to $V'^3$ each independently represents a divalent hydrocarbon group which may have a substituent.

The hydrocarbon group as a divalent linking group may be either an aliphatic hydrocarbon group or an aromatic hydrocarbon group.

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof can be given.

Specific examples of the linear or branched aliphatic hydrocarbon group include the same group as exemplified above for $Va^1$ in formula (a1-1) described later.

The linear or branched aliphatic hydrocarbon group may or may not have a substituent. Examples of the substituent include a fluorine atom, a fluorinated alkyl group of 1 to 5 carbon atoms, and a carbonyl group.

As examples of the hydrocarbon group containing a ring in the structure thereof, a cyclic aliphatic hydrocarbon group containing a hetero atom in the ring structure thereof and may have a substituent (a group in which two hydrogen atoms have been removed from an aliphatic hydrocarbon ring), a group in which the cyclic aliphatic hydrocarbon group is bonded to the terminal of the aforementioned chain-like aliphatic hydrocarbon group, and a group in which the cyclic aliphatic group is interposed within the aforementioned linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

Specific examples of the cyclic aliphatic hydrocarbon group include the same group as exemplified for $Va^1$ in formula (a1-1) described later.

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

Specific examples of the aromatic hydrocarbon group as a divalent hydrocarbon group include the same group as exemplified for $Va^1$ in formula (a1-1) described later.

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group of 1 to 5 carbon atoms, and a methyl group, an ethyl group, a propyl group, an n-butyl group or a tert-butyl group is particularly desirable.

As the alkoxy group, the halogen atom and the halogenated alkyl group for the substituent, the same groups as the aforementioned substituent groups for substituting a hydrogen atom within the cyclic aliphatic hydrocarbon group can be used.

In general formulae (Y-lg-1) to (Y-lg-14), $V'^1$ is preferably divalent aromatic hydrocarbon group which may have a substituent, and most preferably an arylene group or an aralkylene group.

In general formulae (Y-lg-1) to (Y-lg-14), each of $V'^2$ and $V'^3$ is preferably an alkylene group which may have a substituent, and most preferably a chain-like alkylene group which may have a substituent.

In general formulae (Y-lg-1) to (Y-lg-14), $V'^4$ represents a divalent hydrocarbon group which has a fluorine atom.

As the divalent hydrocarbon group for $V'^4$ which has a fluorine atom, those given as examples of the divalent hydrocarbon group for $V'^1$ to $V'^3$ in general formulae (Y-lg-1) to (Y-lg-14) are preferable, an alkylene group of 1 to 5 carbon atoms is more preferable, and a methylene group or an ethylene group is more preferable. It is preferable that part or all of the hydrogen atom within the hydrocarbon group constituting $V'^4$ are substituted with fluorine, and it is more preferable that 30 to 100% of the hydrogen atoms within the hydrocarbon group are substituted with fluorine. Among these, a (per)fluoroalkylene group in which part or all of the hydrogen atoms of the alkylene group given as examples of the divalent hydrocarbon group for the aforementioned $V'^1$ to $V'^3$ has been substituted with fluorine is most preferable.

Examples of the alkyl group of 1 to 5 carbon atoms for $R'^1$ in general formulae (Y-lg-1) to (Y-lg-14) include a methyl group, an ethyl group, a propyl group, an isopropyl group, an n-butyl group, an isobutyl group, a tert-butyl group, a pentyl group, an isopentyl group, and a neopentyl group.

In general formula (b1), $R^1$ represents a hydrocarbon group which may have a substituent, and is the same as defined for $R^{101}$, $R^{104}$ to $R^{108}$ in general formulae (b-1) to (b-3) described later.

The hydrocarbon group for $R^1$ which may have a substituent is preferably aryl group which may have a substituent, an alkyl group which may have a substituent or an alkenyl group which may have a substituent is preferable, and is the same as defined for $R^{201}$ to $R^{207}$, $R^{211}$ and $R^{212}$ in general formulae (ca-1) to (ca-3) described later. The substituent for $R^1$ is also the same as defined for $R^{201}$ to $R^{207}$, $R^{211}$ and $R^{212}$, and an alkyl group, an aryl group or an arylthio group is most preferable.

In general formula (b1), $R^2$ represents an alkyl group of 1 to 5 carbon atoms or an alkoxy group of 1 to 5 carbon atoms. Examples of the alkyl group of 1 to 5 carbon atoms include a methyl group, an ethyl group, a propyl group, an n-butyl group and a tert-butyl group. The alkoxy group of 1 to 5 carbon atoms for $R^2$ is preferably linear or branched. Specific examples of the alkoxy group include the aforementioned alkyl groups for the substituent having an oxygen atom (—O—) bonded thereto.

In general formula (b1), p represents an integer of 0 to 5. In general formula (b1), p is preferably an integer of 0 to 3, more preferably 0 or 1, and most preferably 0.

In general formula (b1), the position at which the sulfonyl group is bonded to the naphthoquinonediazide structure is preferably the 4th, 5th or 6th position, more preferably the 4th or 5th position, and most preferably the 4th position.

Specific examples of the cation moiety of the compound represented by general formula (b1) are shown below.

[Chemical Formula 5]

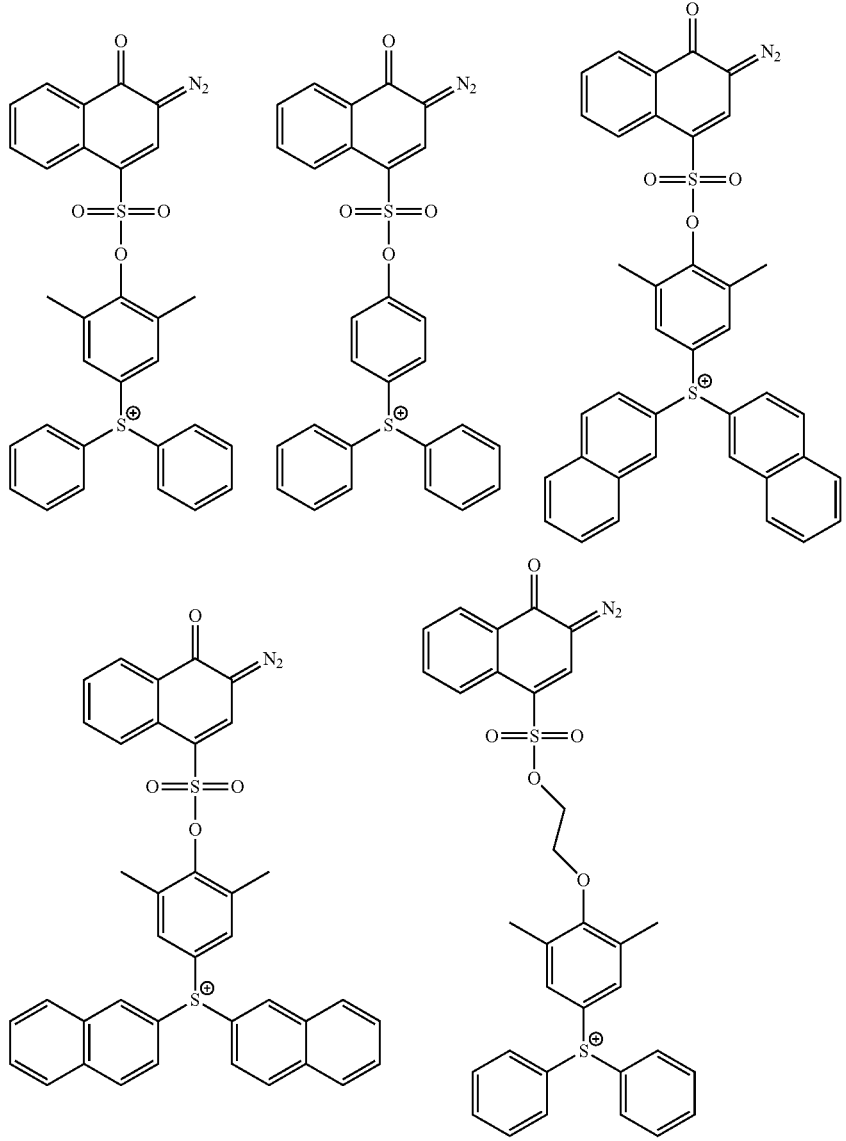

[Chemical Formula 6]
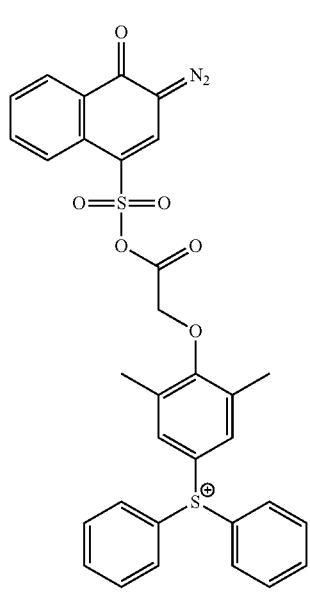 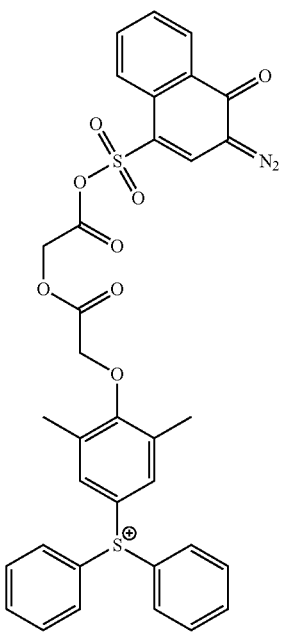 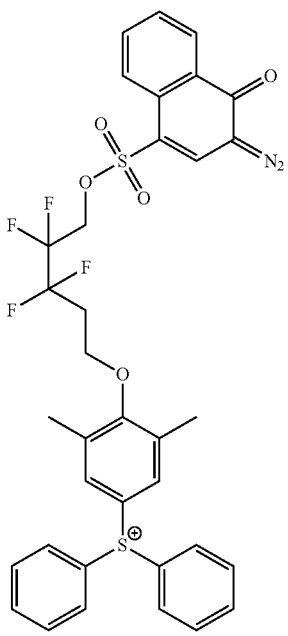
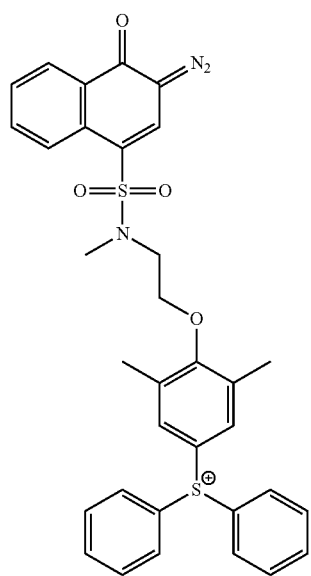

[Chemical Formula 7]
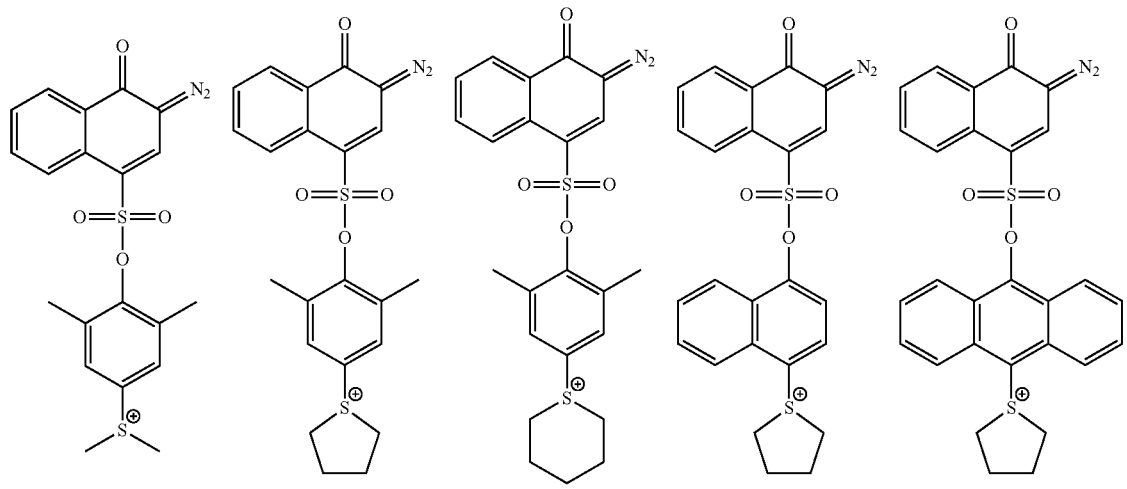
[Chemical Formula 8]
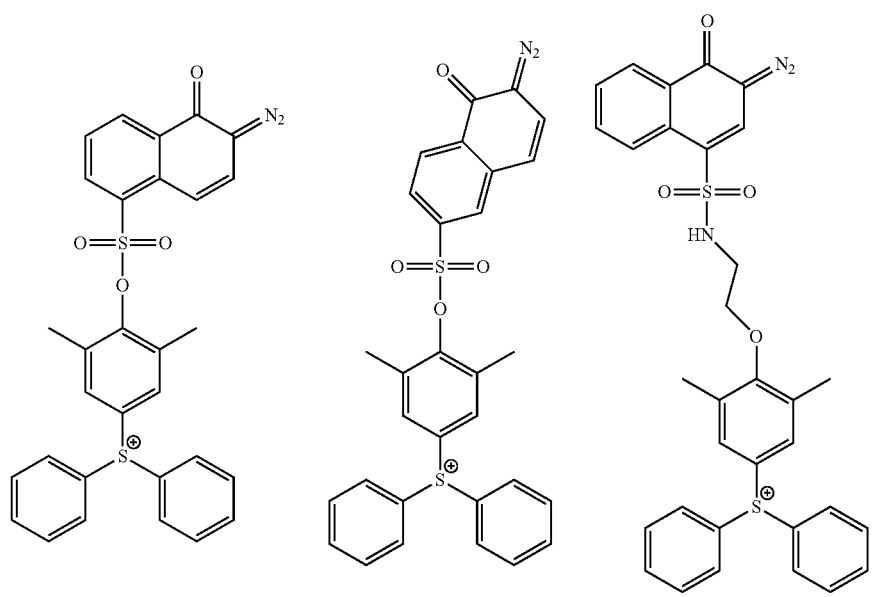

-continued
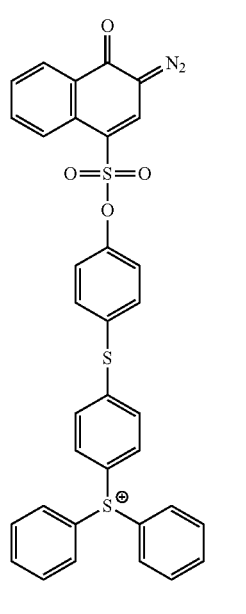 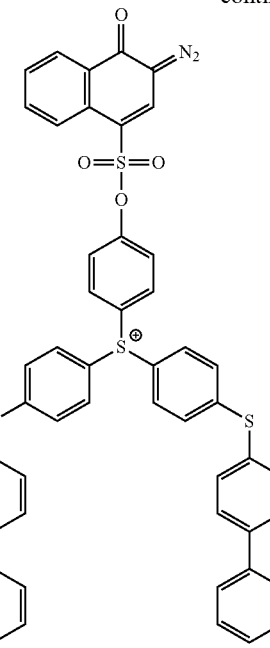 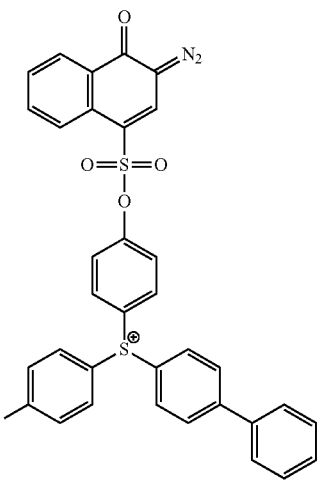
[Chemical Formula 9]
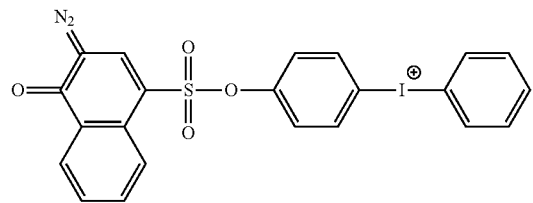
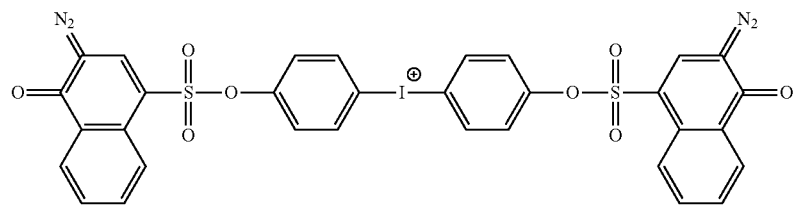
[Chemical Formula 10]
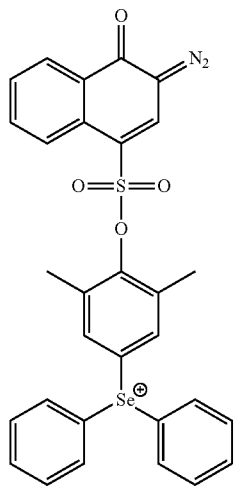 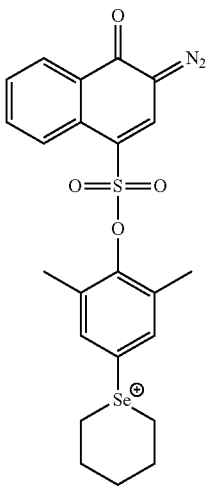 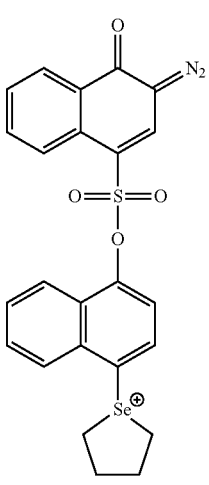

[Chemical Formula 11]
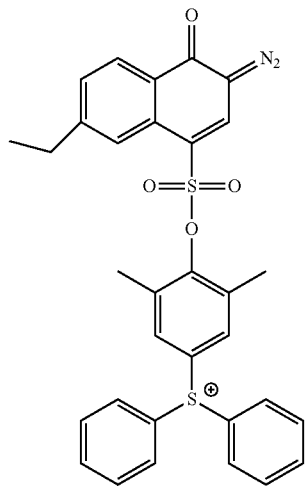 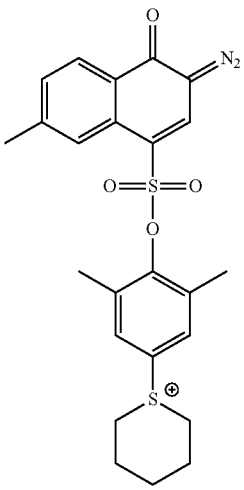 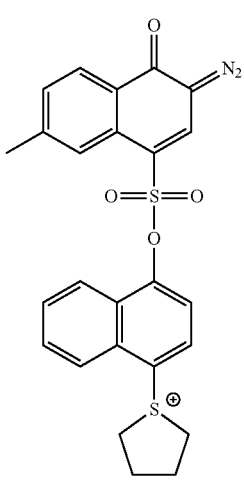 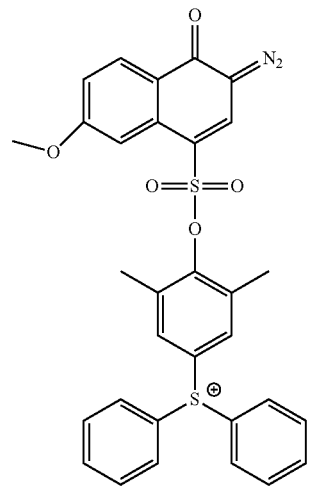
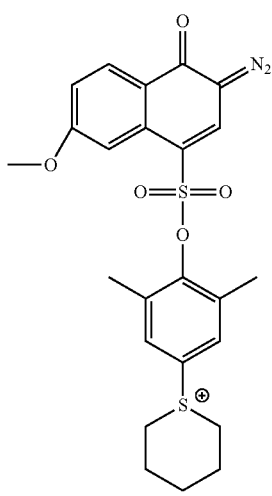 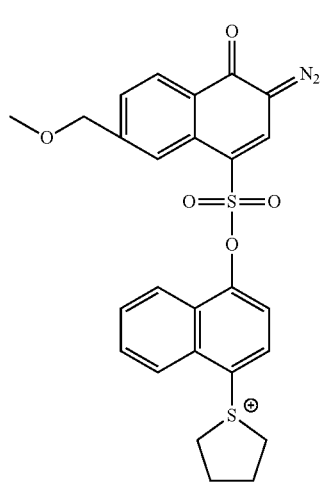

[Chemical Formula 11]

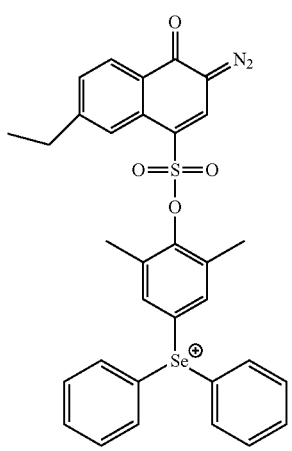 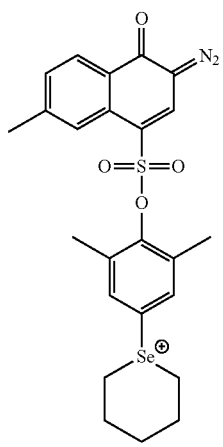 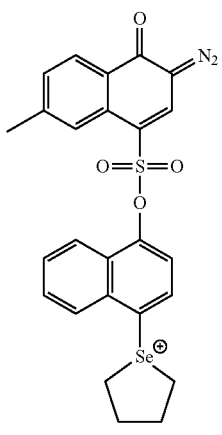 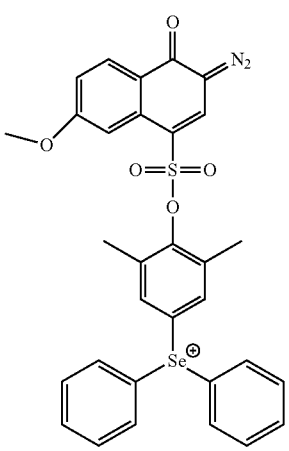

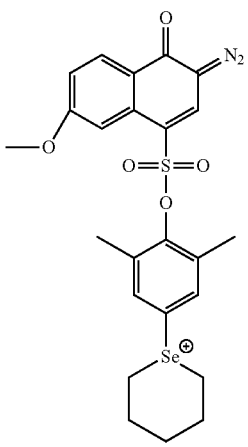 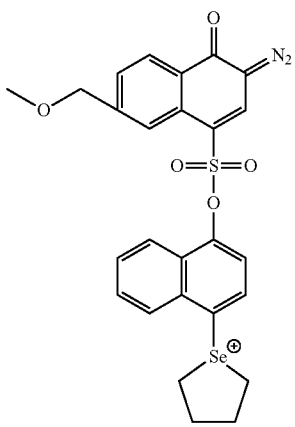

In general formula (hi), X⁻ represents a counteranion.

Examples of the counteranion for X⁻ include a sulfonate anion, a carboxylate anion, an imide anion, a methide anion, a carboanion, a borate anion, a halogen anion, a phosphate anion, an antimonate anion and an arsenate anion.

For example, the same anions as those defined for the anion in general formulae (b-1) to (b-3) and (d1-1) to (d1-3) described later can be mentioned. Alternatively, the counteranion for X⁻ may be an anion represented by general formula (b-an1) shown below.

[Chemical Formula 12]

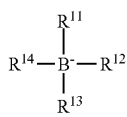
(b-an1)

In the formula, $R^{11}$ to $R^{14}$ each independently represents a fluorine atom, an alkyl group which may have a substituent, or an aryl group which may have a substituent.

In general formula (b-an1), the alkyl group for $R^{11}$ to $R^{14}$ is preferably an alkyl group of 1 to 20 carbon atoms, and the same chain-like or cyclic alkyl groups as those defined for $Ra^{13}$ in formula (a1-r-1) below can be mentioned.

The aryl group for $R^{11}$ to $R^{14}$ is preferably a phenyl group or a naphthyl group.

In the case where $R^{11}$ to $R^{14}$ represent an alkyl group or an aryl group, examples of the substituent include a halogen atom, a halogenated alkyl group, an alkyl group, an alkoxy group, an alkylthio group, a hydroxy group and a carbonyl group. The examples of the substituent are the same as defined for the structural unit (a2) described later. Examples of the alkylthio group include an alkylthio group of 1 to 4 carbon atoms. Among these examples, a halogenated alkyl group, an alkyl group, an alkoxy group and an alkylthio group is preferable.

In general formula (b-an1), $R^{11}$ to $R^{14}$ is preferably a fluorine atom, a fluorinated alkyl group or a group represented by general formula (b-an1') shown below.

[Chemical Formula 13]

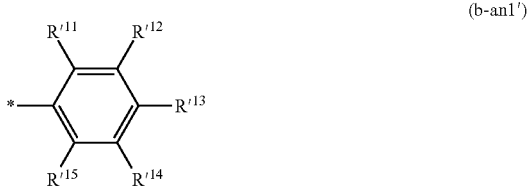

(b-an1′)

In the formula, $R'^{11}$ to $R'^{15}$ each independently represents a hydrogen atom, a fluorine atom, a trifluoromethyl group, an alkyl group of 1 to 4 carbon atoms, an alkoxy group of 1 to 4 carbon atoms or an alkylthio group of 1 to 4 carbon atoms; and * represents a valence bond.

In the general formula above, specific examples of the alkyl group of 1 to 4 carbon atoms include a methyl group, an ethyl group, an n-propyl group and an n-butyl group. Among these, a methyl group, an ethyl group or an n-butyl group is preferable, and a methyl group or an ethyl group is more preferable.

In the general formula above, specific examples of the alkoxy group of 1 to 4 carbon atoms include a methoxy group, an ethoxy group, an n-propoxy group, an iso-propoxy group, an n-butoxy group and a tert-butoxy group, and a methoxy group and an ethoxy group are more preferable.

In the general formula above, the alkylthio group of 1 to 4 carbon atoms is preferably a methylthio group, an ethylthio group, an n-propylthio group, an iso-propylthio group, an n-butylthio group or a tert-butylthio group, and more preferably a methylthio group or an ethylthio group.

Specific examples of preferable anion moiety represented by general formula (b-an1) include tetrakis(pentafluorophenyl)borate ($[B(C_6F_5)_4]^-$), tetrakis[(trifluoromethyl)phenyl]borate ($[B(C_6H_4CF_3)_4]^-$), difluorobis(pentafluorophenyl)borate ($[(C_6F_5)_2BF_2]^-$), trifluoro(pentafluorophenyl)borate ($[(C_6F_5)BF_3]^-$) and tetrakis(difluophenyl)borate ($[B(C_6H_3F_2)_4]^-$). Among these examples, tetrakis(pentafluorophenyl)borate ($[B(C_6F_5)_4]^-$) is most preferable.

The counteranion for $X^-$ may be a halogen anion, a phosphate anion, an antimonate anion ($SbF_6^-$) or an arsenate anion ($AsF_6^-$). Examples of the halogen atom include chlorine and bromine, and examples of the phosphate anion include $PF_6^-$ and an anion represented by general formula (b-an2) shown below.

[Chemical Formula 14]

(b-an2)

In the formula, $R^{15}$ represents a fluorinated alkyl group of 1 to 8 carbon atoms; and q represents an integer of 1 to 6.

In general formula (b-an2), specific examples of the fluorinated alkyl group of 1 to 8 carbon atoms include $CF_3$, $CF_3CF_2$, $(CF_3)_2CF$, $CF_3CF_2CF_2$, $CF_3CF_2CF_2CF_2$, $(CF_3)_2CFCF_2$, $CF_3CF_2(CF_3)CF$ and $C(CF_3)_3$.

<<Resist Composition>>

The resist composition of the present invention includes a base component (A) (hereafter, referred to as "component (A)") which exhibits changed solubility in a developing solution under action of acid, and an acid-generator component (B) (hereafter, referred to as "component (B)") which generates acid upon exposure.

By virtue of containing the components (A) and (B), the resist composition of the present invention has a characteristic of exhibiting changed solubility in a developing solution upon exposure. When a resist film is formed using the resist composition, and the resist film is subjected to a selective exposure, acid is generated from the component (B) at exposed portions, and the generated acid acts on the component (A) to change the solubility of the component (A) in a developing solution. As a result, the solubility of the exposed portions in a developing solution is changed, whereas the solubility of the unexposed portions in a developing solution remain unchanged. Therefore, by subjecting the resist film to development, the exposed portions are dissolved and removed to form a positive-tone resist pattern in the case of a positive resist, whereas the unexposed portions are dissolved and removed to form a negative-tone resist pattern in the case of a negative resist.

In the present specification, a resist composition which forms a positive resist pattern by dissolving and removing the exposed portions is called a positive resist composition, and a resist composition which forms a negative resist pattern by dissolving and removing the unexposed portions is called a negative resist composition.

The resist composition of the present invention may be either a positive resist composition or a negative resist composition. Further, in the formation of a resist pattern, the resist composition of the present invention can be applied to an alkali developing process using an alkali developing solution in the developing treatment, or a solvent developing process using a developing solution containing an organic solvent (organic developing solution) in the developing treatment. The resist composition of the present invention is preferably used for forming a positive-tone resist pattern by an alkali developing process, and for forming a negative-tone pattern in a solvent developing process. In such a resist composition, as the component (A), it is preferable to use a base component which exhibits increased solubility in an alkali developing solution and decreased solubility in an organic developing solution by the action of acid.

<Base Component: Component (A)>

In the present invention, the term "base component" refers to an organic compound capable of forming a film.

As the base component, an organic compound having a molecular weight of 500 or more is used. When the organic compound has a molecular weight of 500 or more, the organic compound exhibits a satisfactory film-forming ability, and a resist pattern of nano level can be easily formed.

The "organic compound having a molecular weight of 500 or more" is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

As a polymer, any of those which have a molecular weight of 1,000 or more is generally used. In the present description and claims, the term "polymeric compound" refers to a polymer having a molecular weight of 1,000 or more.

With respect to a polymeric compound, the "molecular weight" is the weight average molecular weight in terms of the polystyrene equivalent value determined by gel permeation chromatography (GPC).

In the case where the resist composition of the present invention is a resist composition which forms a positive pattern in an alkali developing process and a negative pattern in a solvent developing process, it is preferable to use a base component (A1) (hereafter, referred to as "component (A1)") which exhibits increased polarity by the action of acid. By using the component (A1), since the polarity of the base component is changed prior to and after exposure, an excellent development contrast can be achieved not only in an alkali developing process, but also in a solvent developing process.

More specifically, in the case of applying an alkali developing process, the component (A1) is substantially insoluble in an alkali developing solution prior to exposure, but when acid is generated from the component (B) upon exposure, the action of this acid causes an increase in the polarity of the base component, thereby increasing the solubility of the component (A1) in an alkali developing solution. Therefore, in the formation of a resist pattern, by conducting selective exposure of a resist film formed by applying the resist composition to a substrate, the exposed portions change from an insoluble state to a soluble state in an alkali developing solution, whereas the unexposed portions remain insoluble in an alkali developing solution, and hence, contrast can be obtained between the exposed portions and the unexposed portions, and a positive-tone pattern can be formed by alkali developing.

On the other hand, in the case of a solvent developing process, the component (A1) exhibits high solubility in an organic developing solution prior to exposure, and when acid is generated from the component (B) upon exposure, the polarity of the component (A1) is increased by the action of the generated acid, thereby decreasing the solubility of the component (A0) in an organic developing solution. Therefore, in the formation of a resist pattern, by conducting selective exposure of a resist film formed by applying the resist composition to a substrate, the exposed portions changes from an soluble state to an insoluble state in an organic developing solution, whereas the unexposed portions remain soluble in an organic developing solution. As a result, by conducting development using an organic developing solution, a contrast can be made between the exposed portions and unexposed portions, thereby enabling the formation of a negative resist pattern by developing with an organic developing solution.

When the resist composition of the present invention is a resist composition which forms a negative pattern in an alkali developing process, in general, as the component (A), a base component that is soluble in an alkali developing solution is used, and a cross-linking agent is blended in the negative resist composition.

A base component that is soluble in an alkali developing solution has an alkali-soluble group such as a hydroxy group, a carboxy group, a sulfoneamide group or the like, and the cross-linking agent has a reactive group which is capable of reacting with the alkali-soluble group. In such a resist composition, when acid is generated from the component (B) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the resist composition onto a substrate, the exposed portions become insoluble in an alkali developing solution, whereas the unexposed portions remain soluble in an alkali developing solution, and hence, a resist pattern can be formed by alkali developing.

Generally, as a base component that is soluble in an alkali developing solution, a resin that is soluble in an alkali developing solution (hereafter, referred to as "alkali-soluble resin") is used.

Examples of the alkali soluble resin include a resin having a structural unit derived from at least one of α-(hydroxyalkyl)acrylic acid and an alkyl ester of α-(hydroxyalkyl)acrylic acid (preferably an alkyl ester having 1 to 5 carbon atoms), as disclosed in Japanese Unexamined Patent Application, First Publication No. 2000-206694; an acrylic resin which has a sulfonamide group and may have an atom other than hydrogen or a substituent bonded to the carbon atom on the α-position or polycycloolefin resin having a sulfoneamide group, as disclosed in U.S. Pat. No. 6,949,325; an acrylic resin which may have an atom other than hydrogen or a substituent bonded to the carbon atom on the α-position and having a fluorinated alcohol, as disclosed in U.S. Pat. No. 6,949,325, Japanese Unexamined Patent Application, First Publication No. 2005-336452 or Japanese Unexamined Patent Application, First Publication No. 2006-317803; and a polycyclolefin resin having a fluorinated alcohol, as disclosed in Japanese Unexamined Patent Application, First Publication No. 2006-259582. These resins are preferable in that a resist pattern can be formed with minimal swelling.

Here, the term "α-(hydroxyalkyl)acrylic acid" refers to one or both of acrylic acid in which an atom other than hydrogen or a substituent is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group, or a melamine-based cross-linking agent is preferable, as it enables formation of a resist pattern with minimal swelling. The amount of the cross-linker added is preferably within a range from 1 to 50 parts by weight, relative to 100 parts by weight of the alkali-soluble resin.

[Resin Component (A1)]

In the resist composition of the present invention, the component (A) preferably includes a resin component (A1) (hereafter, referred to as "component (A1)") which has a structural unit (a1) containing an acid decomposable group that exhibits increased polarity by the action of acid.

As the component (A1), a resin component (base resin) typically used as a base component for a chemically amplified resist composition can be used alone, or two or more of such resin components can be mixed together.

It is preferable that the component (A1) further has, in addition to the structural unit (a1), a structural unit (a2) containing a lactone-containing cyclic group, a carbonate-containing cyclic group, or an $_2$-containing cyclic group.

It is preferable that the component (A1) further has, in addition to the constituent unit (a1), or in addition to the constituent units (a1) and (a2), a constituent unit (a3) containing a polar group.

(Structural Unit (a1))

The structural unit (a1)) is a structural unit containing an acid decomposable group that exhibits increased polarity by the action of acid.

The term "acid decomposable group" refers to a group in which at least a part of the bond within the structure thereof is cleaved by the action of an acid.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group ($-SO_3H$). Among these, a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

Here, the "acid dissociable group" includes:

(i) a group in which the bond between the acid dissociable group and the adjacent atom is cleaved by the action of acid; and (ii) a group in which one of the bonds is cleaved by the action of acid, and then a decarboxylation reaction occurs, thereby cleaving the bond between the acid dissociable group and the adjacent atom.

It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. By the increase in the polarity, the solubility in an alkali developing solution changes, and the solubility in an alkali developing solution is relatively increased, whereas the solubility in an organic developing solution is relatively decreased.

The acid dissociable group is not particularly limited, and any of the groups that have been conventionally proposed as acid dissociable groups for the base resins of chemically amplified resists can be used.

Examples of the acid dissociable group for protecting the carboxy group or hydroxy group as a polar group include the acid dissociable group represented by general formula (a1-r-1) shown below (hereafter, referred to as "acetal-type acid dissociable group").

[Chemical Formula 15]

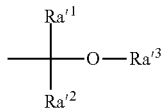

(a1-r-1)

In the formula, $Ra'^1$ and $Ra'^2$ represents a hydrogen atom or an alkyl group; and $Ra'^3$ represents a hydrocarbon group, provided that $Ra'^3$ may be bonded to $Ra'^1$ or $Ra'^2$.

In the formula (a1-r-1), it is preferable that at least one of $Ra'^1$ and $Ra'^2$ represents a hydrogen atom, and it is more preferable that both of $Ra'^1$ and $Ra'^2$ represent a hydrogen atom.

In the case where $Ra'^1$ or $Ra'^2$ is an alkyl group, as the alkyl group, the same alkyl groups as those described above the for the substituent which may be bonded to the carbon atom on the α-position of the aforementioned α-substituted acrylate ester can be mentioned, and an alkyl group of 1 to 5 carbon atoms is preferable. Specific examples of the alkyl group include linear or branched alkyl groups such as a methyl group, an ethyl group, a propyl group, an isopropyl group, an n-butyl group, an isobutyl group, a tert-butyl group, a pentyl group, an isopentyl group and a neopentyl group. Of these, a methyl group or an ethyl group is preferable, and a methyl group is particularly preferable.

In the formula (a1-r-1), examples of the hydrocarbon group for $Ra'^3$ include a linear, branched or cyclic alkyl group. The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5. Specific examples of such branched alkyl groups include an isopropyl group, an isobutyl group, a tert-butyl group, an isopentyl group and a neopentyl group, and an isopropyl group is particularly desirable.

The cyclic alkyl group preferably has 3 to 20 carbon atoms, and more preferably 4 to 12. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. In these cyclic alkyl groups, part of the carbon atoms constituting the ring may be replaced with an ethereal oxygen atom (—O—).

In the case where $Ra'^3$ is bonded to $Ra'^1$ or $Ra'^2$ to form a ring, the cyclic group is preferably a 4 to 7-membered ring, and more preferably a 4 to 6-membered ring. Specific examples of the cyclic group include tetrahydropyranyl group and tetrahydrofuranyl group.

Examples of the acid dissociable group for protecting the carboxy group as a polar group include the acid dissociable group represented by general formula (a1-r-2) shown below (hereafter, with respect to the acid dissociable group represented by the following formula (a1-r-2), the acid dissociable group constituted of alkyl groups is referred to as "tertiary ester-type acid dissociable group").

[Chemical Formula 16]

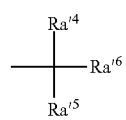

(a1-r-2)

In the formula, $Ra'^4$ to $Ra'^6$ each independently represents a hydrocarbon group, provided that $Ra'^5$ and $Ra'^6$ may be mutually bonded to form a ring.

As the hydrocarbon group for $Ra'^4$ to $Ra'^6$, the same groups as those described above for $Ra'^3$ can be mentioned.

$Ra'^4$ is preferably an alkyl group of 1 to 5 carbon atoms. In the case where $Ra'^5$ and $Ra'^6$ are mutually bonded to form a ring, a group represented by general formula (a1-r2-1) shown below can be mentioned. On the other hand, in the case where $Ra'^4$ to $Ra'^6$ are not mutually bonded and independently represent a hydrocarbon group, the group represented by general formula (a1-r2-2) shown below can be mentioned.

[Chemical Formula 17]

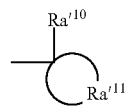

(a1-r2-1)

(a1-r2-2)

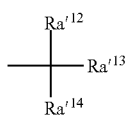

In the formulae, $Ra'^{10}$ represents an alkyl group of 1 to 10 carbon atoms; $Ra'^{11}$ is a group which forms an aliphatic cyclic group together with a carbon atom having $Ra'^{10}$ bonded thereto; and $Ra'^{12}$ to $Ra'^{14}$ each independently represents a hydrocarbon group.

In the formula (a1-r2-1), as the alkyl group of 1 to 10 carbon atoms for $Ra'^{10}$, the same groups as described above for the linear or branched alkyl group for $Ra'^3$ in the formula (a1-r-1) are preferable. In the formula (a1-r2-1), as the aliphatic cyclic group which is formed by $Ra'^{11}$, the same groups as those described above for the cyclic alkyl group for $Ra'^3$ in the formula (a1-r-1) are preferable.

In the formula (a1-r2-2), it is preferable that $Ra'^{12}$ and $Ra'^{14}$ each independently represents an alkyl group or 1 to 10 carbon atoms, and it is more preferable that the alkyl group is the same group as the described above for the linear or branched alkyl group for $Ra'^3$ in the formula (a1-r-1), it is still more preferable that the alkyl group is a linear alkyl group of 1 to 5 carbon atoms, and it is particularly preferable that the alkyl group is a methyl group or an ethyl group.

In the formula (a1-r2-2), it is preferable that $Ra'^{13}$ is the same group as described above for the linear, branched or cyclic alkyl group for $Ra'^3$ in the formula (a1-r-1).

Among these, the same cyclic alkyl group as those describe above for $Ra^{-3}$ is more preferable.

Specific examples of the formula (a1-r2-1) are shown below. In the formulae shown below, "*" represents a valence bond.

[Chemical Formula 18]

(r-pr-m1)

(r-pr-m2)

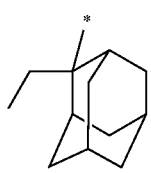

(r-pr-m3)

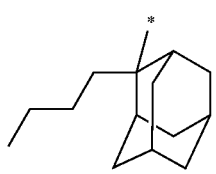

(r-pr-m4)

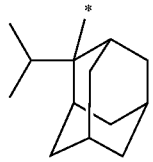

(r-pr-m5)

(r-pr-m6)

(r-pr-m7)

(r-pr-m8)

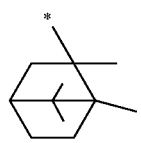

(r-pr-m9)

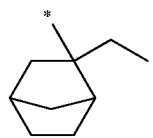

(r-pr-m10)

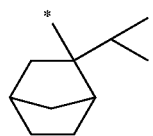

(r-pr-m11)

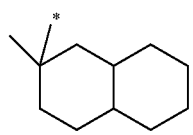

(r-pr-m12)

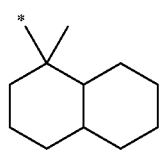

(r-pr-m13)

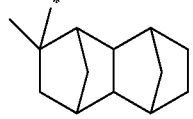

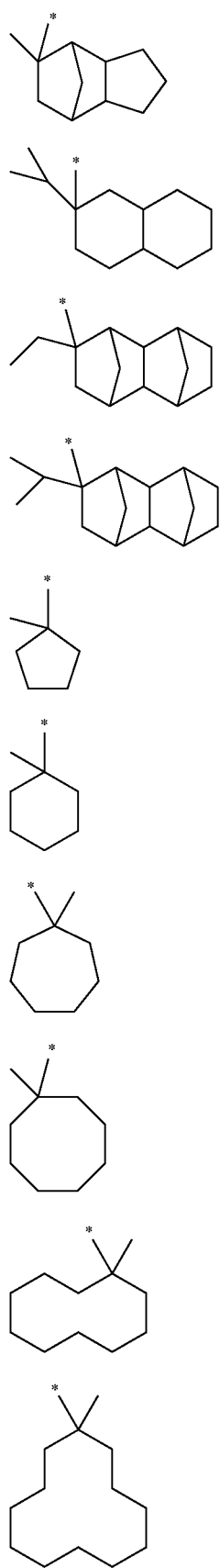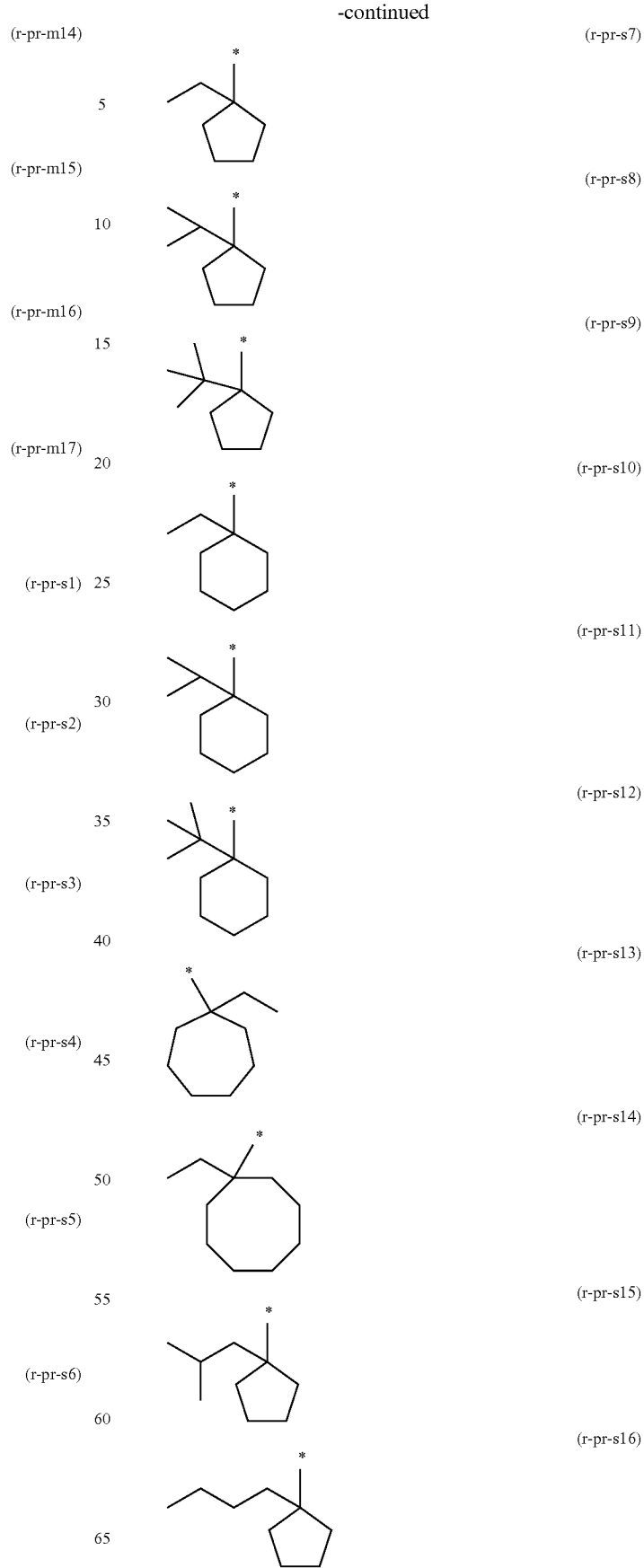

(r-pr-s17)
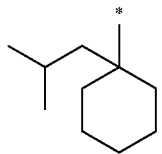
(r-pr-s18)
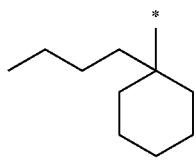
Specific examples of the formula (a1-r2-2) are shown below.
[Chemical Formula 19]
(r-pr-cm1)
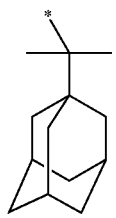
(r-pr-cm2)
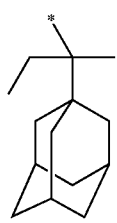
(r-pr-cm3)
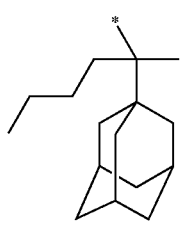
(r-pr-cm4)
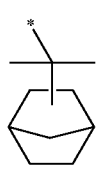
(r-pr-cm5)
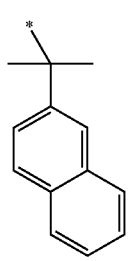
(r-pr-cm6)
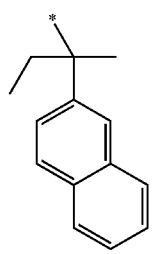
(r-pr-cm7)
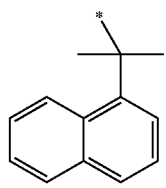
(r-pr-cm8)
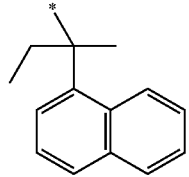
(r-pr-cs1)
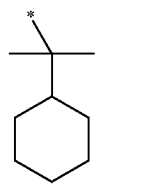
(r-pr-cs2)
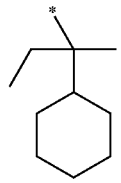
(r-pr-cs3)
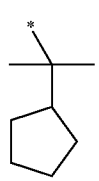
(r-pr-cs4)
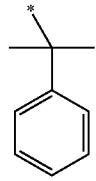
(r-pr-cs5)

(r-pr-c1)

(r-pr-c2)

(r-pr-c3)

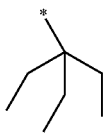

Examples of the acid dissociable group for protecting a hydroxy group as a polar group include the acid dissociable group represented by general formula (a1-r-3) shown below (hereafter, referred to as "tertiary alkyloxycarbonyl-type acid dissociable group").

[Chemical Formula 20]

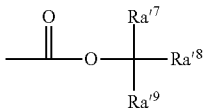

(a1-r-3)

In the formula, $Ra'^7$ to $Ra'^9$ each independently represents an alkyl group.

In the formula (a1-r-3), $Ra'^7$ to $Ra'^9$ is preferably an alkyl group of 1 to 5 carbon atoms, and more preferably an alkyl group of 1 to 3 carbon atoms.

Further, the total number of carbon atoms within the alkyl group is preferably 3 to 7, more preferably 3 to 5, and most preferably 3 or 4.

Examples of the structural unit (a1) include a structural unit derived from an acrylate ester which may have the hydrogen atom bonded to the carbon atom on the α-position substituted with a substituent and contains an acid decomposable group which exhibits increased polarity by the action of acid; a structural unit derived from hydroxystyrene or a hydroxystyrene derivative in which at least a part of the hydrogen atom of the hydroxy group is protected with a substituent containing an acid decomposable group; and a structural unit derived from vinylbenzoic acid or a vinylbenzoic acid derivative in which at least a part of the hydrogen atom within —C(=O)—OH is protected with a substituent containing an acid decomposable group.

As the structural unit (a1), a structural unit derived from an acrylate ester which may have the hydrogen atom bonded to the carbon atom on the α-position substituted with a substituent is preferable.

Specific examples of preferable structural units for the structural unit (a1) include structural units represented by general formulas (a1-1) and (a1-2) shown below.

[Chemical Formula 21]

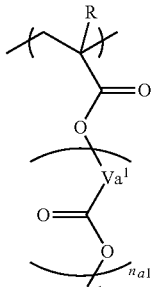

(a1-1)

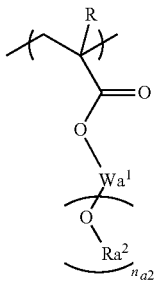

(a1-2)

In the formulae, R represents a hydrogen atom, an alkyl group of 1 to 5 carbon atoms or a halogenated alkyl group of 1 to 5 carbon atoms; $Va^1$ represents a divalent hydrocarbon group which may contain an ether bond, an urethane bond or an amide bond; $n_{a1}$ each independently represents an integer of 0 to 2; $Ra^1$ represents an acid dissociable group represented by the aforementioned formula (a1-r-1) or (a1-r-2); $Wa^1$ represents a hydrocarbon group having a valency of $n_{a2}+1$; $n_{a2}$ represents an integer of 1 to 3; and $Ra^2$ represents an acid dissociable group represented by the aforementioned formula (a1-r-1) or (a1-r-3).

In formula (a1-1) above, the alkyl group of 1 to 5 carbon atoms is preferably a linear or branched alkyl group, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which part or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

The divalent hydrocarbon group for $Va^1$ may be either an aliphatic hydrocarbon group or an aromatic hydrocarbon group. An "aliphatic hydrocarbon group" refers to a hydrocarbon group that has no aromaticity. The aliphatic hydrocarbon group as the divalent hydrocarbon group for $Va^1$ may be either saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

Further, as the group for $Va^1$, a group in which the aforementioned divalent hydrocarbon group has been bonded via an ether bond, urethane bond or amide bond can be mentioned.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. As the linear or branched aliphatic hydrocarbon group, the same groups as those described above can be used.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aromatic hydrocarbon group is a hydrocarbon group having an aromatic ring.

The aromatic hydrocarbon group as the divalent hydrocarbon group for $Va^1$ preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom.

Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); a group in which one hydrogen atom has been removed from the aforementioned aromatic hydrocarbon ring (aryl group) and one hydrogen atom thereof has been substituted with an alkylene group (for example, a group in which one hydrogen atom has been removed from an aryl group within an arylalkyl group such as a benzyl group, a phenethyl group, a 1-naphthylmethyl group, a 2-naphthylmethyl group, a 1-naphthylethyl group, or a 2-naphthylethyl group); and a group in which two hydrogen atoms have been removed from an aromatic compound containing 2 or more aromatic rings (e.g., biphenyl, fluorene or the like) The alkylene group (alkyl chain within the arylalkyl group) preferably has 1 to 4 carbon atom, more preferably 1 or 2, and most preferably 1.

In the aforementioned formula (a1-2), the hydrocarbon group for $Wa^1$ having a valency of $n_{a2}+1$ may be either an aliphatic hydrocarbon group or an aromatic hydrocarbon group. The aliphatic cyclic group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof. As the specific examples thereof, the same groups as those described above for $Va^1$ in the aforementioned formula (a1-1) can be mentioned.

The valency of $n_{a2}+1$ is preferably divalent, trivalent or tetravalent, and divalent or trivalent is more preferable.

As the structural unit (a1-2), a structural unit represented by general formula (a1-2-01) shown below is particularly desirable.

[Chemical Formula 22]

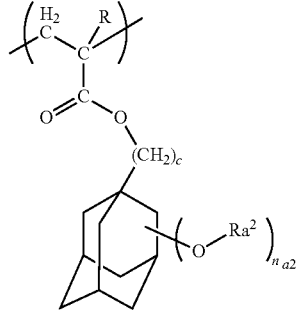

(a1-2-01)

In the formula (a1-2-01), $Ra^2$ represents an acid dissociable group represented by the aforementioned formula (a1-r-1) or (a1-r-3); $n_{a2}$ is an integer of 1 to 3, preferably 1 or 2, and more preferably 1; c is an integer of 0 to 3, preferably 0 or 1, and more preferably 1; and R is the same as defined above.

Specific examples of the structural unit (a1-1) are shown below.

[Chemical Formula 23]
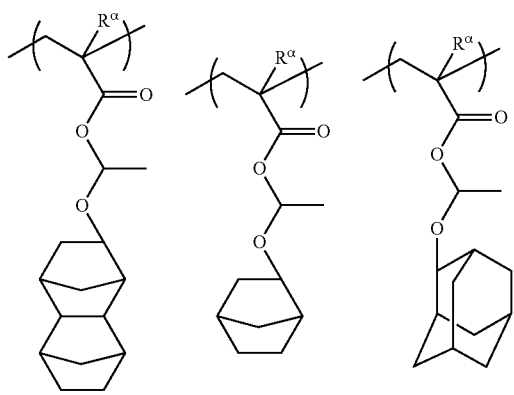
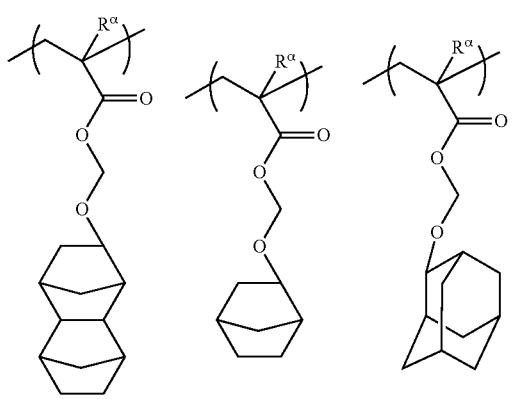
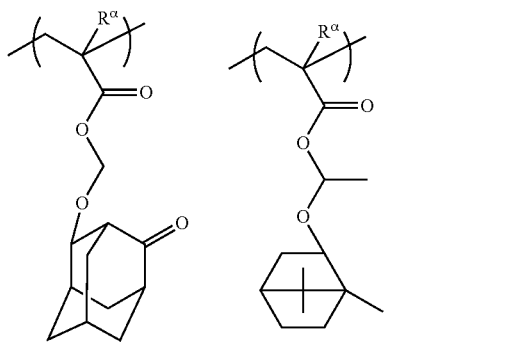
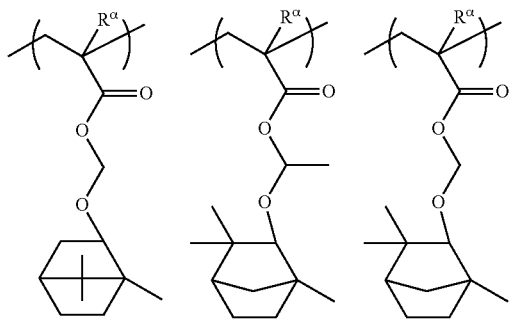
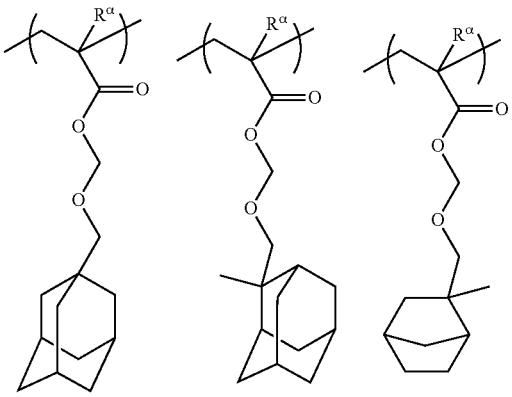
[Chemical Formula 24]
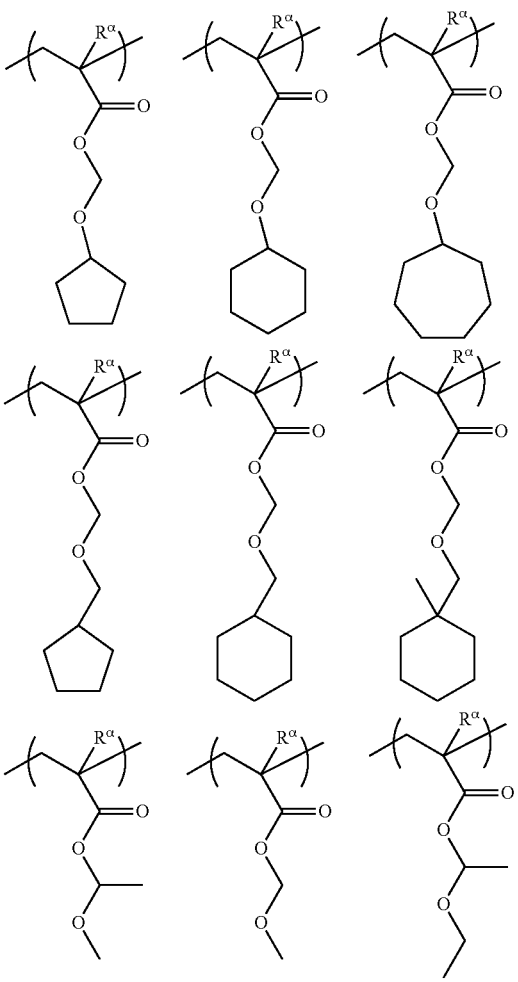
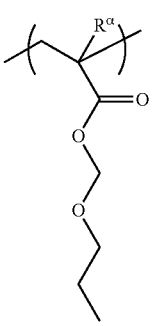

[Chemical Formula 25]
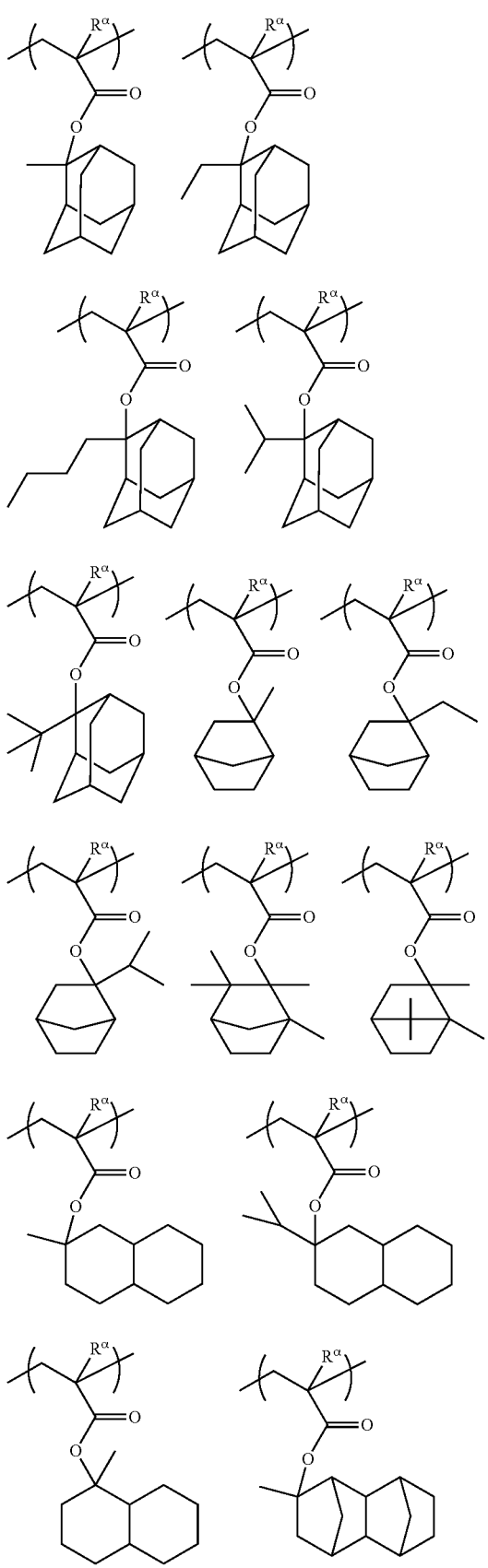
[Chemical Formula 26]
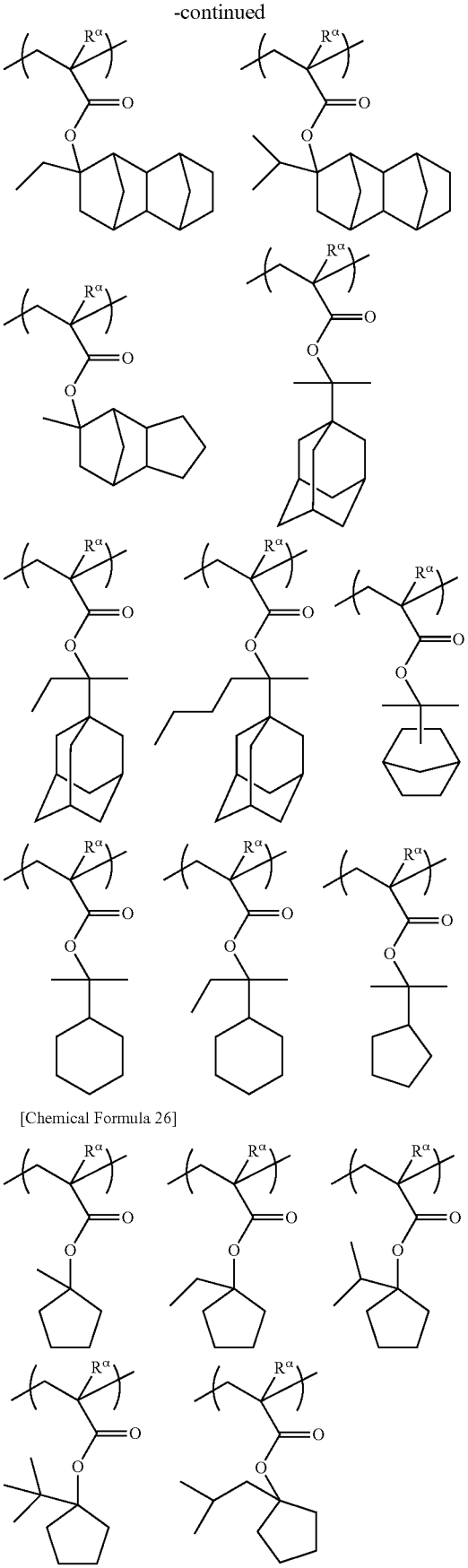

-continued
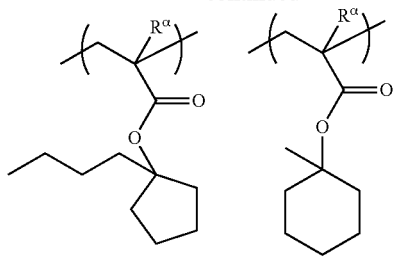
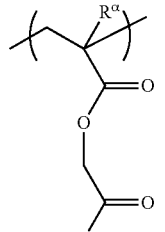
[Chemical Formula 27]
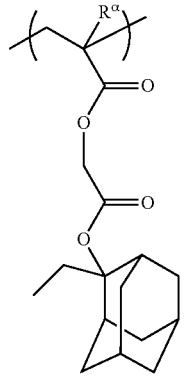
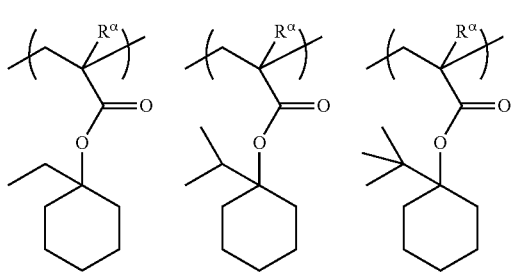
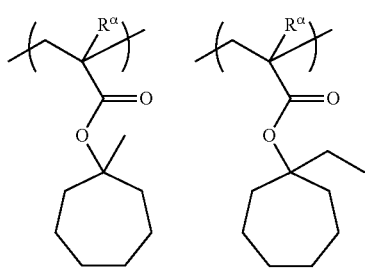
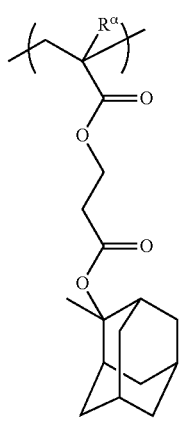
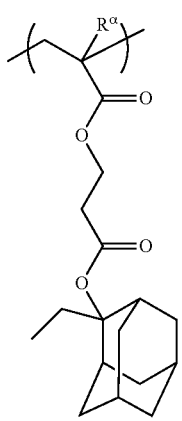
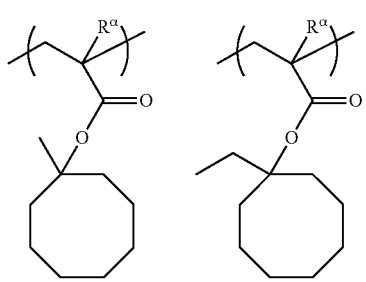
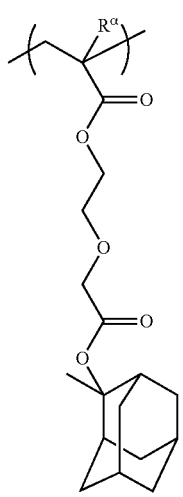
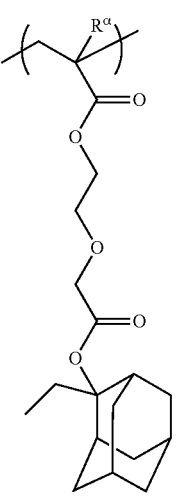

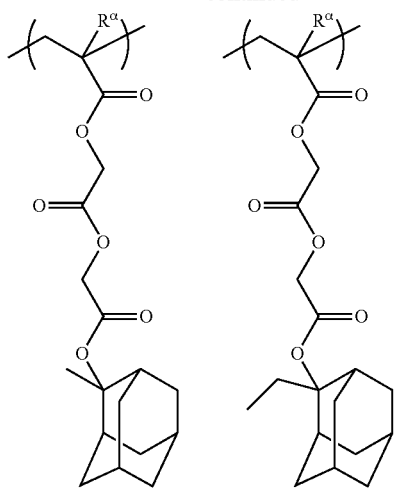
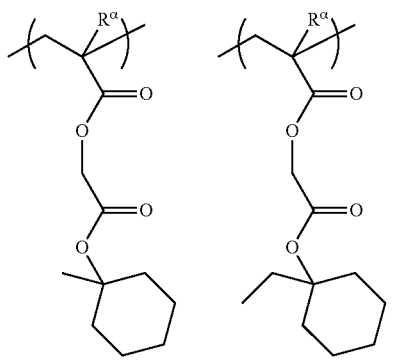
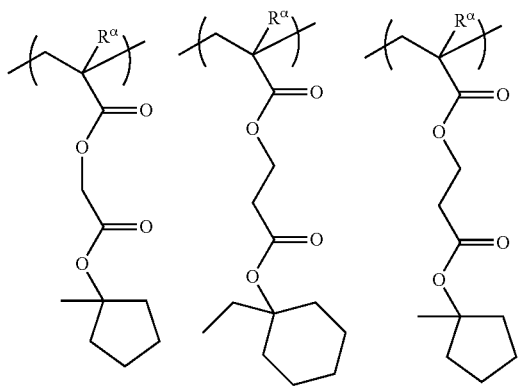
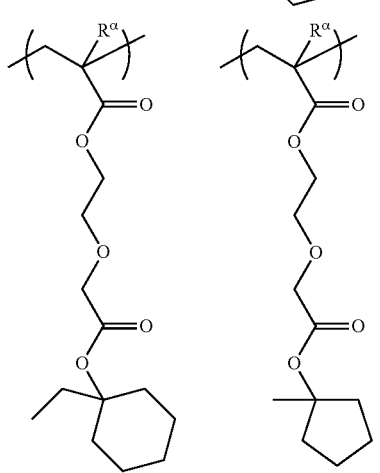
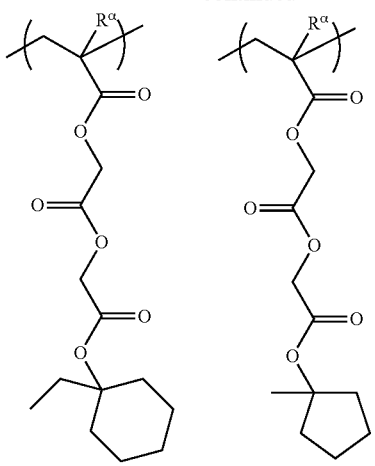
Specific examples of the structural unit (a1-2) are shown below.
[Chemical Formula 28]
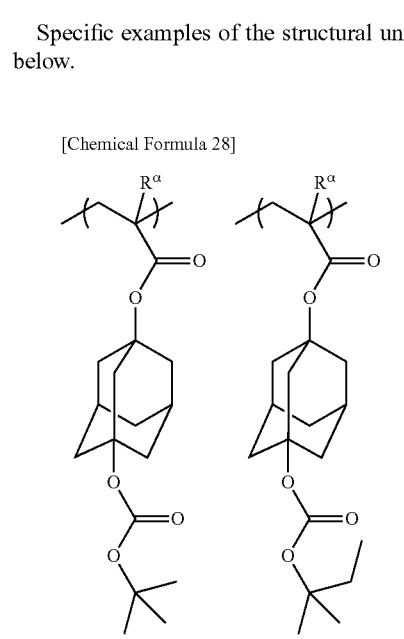
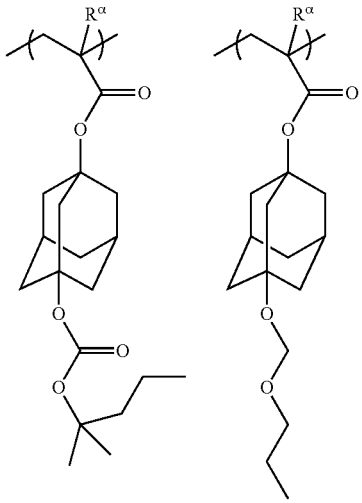

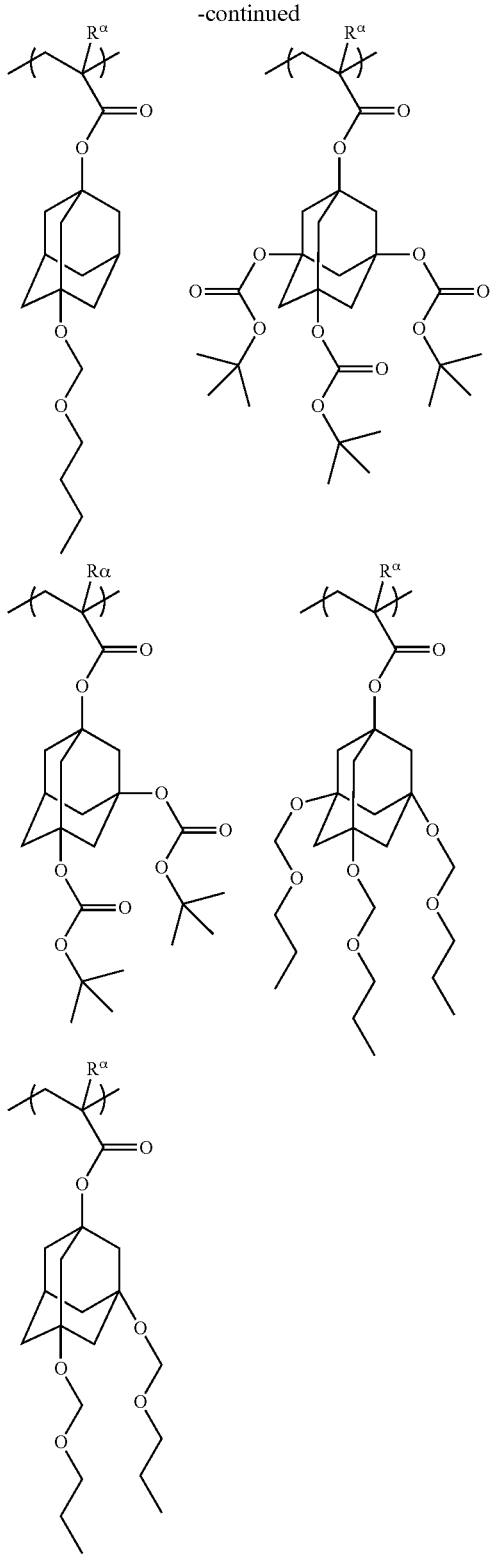

In the component (A1), the amount of the structural unit (a1) based on the combined total of all structural units constituting the component (A1) may be 100%, preferably 20 to 80 mol %, more preferably 20 to 75 mol %, and still more preferably 25 to 70 mol %. When the amount of the structural unit (a1) is at least as large as the lower limit of the above-mentioned range, a pattern can be easily formed using a resist composition prepared from the component (A1), and various lithography properties such as sensitivity, resolution, LWR and the like are improved. On the other hand, when the amount of the structural unit (a1) is no more than the upper limit of the above-mentioned range, a good balance can be achieved with the other structural units.

(Structural Unit (a2))

It is preferable that the component (A1) further has, in addition to the structural unit (a1), a structural unit (a2) containing a lactone-containing cyclic group, a carbonate-containing cyclic group, or an $_2$-containing cyclic group.

When the component (A1) is used for forming a resist film, the structural unit (a2) containing a lactone-containing cyclic group or a carbonate-containing cyclic group is effective in improving the adhesion between the resist film and the substrate.

The aforementioned structural unit (a1) which contains a lactone-containing cyclic group or a carbonate-containing cyclic group falls under the definition of the structural unit (a2); however, such a structural unit is regarded as a structural unit (a1), and does not fall under the definition of the structural unit (a2).

When the component (A1) is used for forming a resist film, the structural unit (a2) containing an —$SO_2$— containing cyclic group is effective in improving the adhesion between the resist film and the substrate.

The aforementioned structural unit (a1) which contains an —$SO_2$— containing cyclic group falls under the definition of the structural unit (a2); however, such a structural unit is regarded as a structural unit (a1), and does not fall under the definition of the structural unit (a2).

The structural unit (a2) is preferably a structural unit represented by general formula (a2-1) shown below.

[Chemical Formula 29]

(a2-1)

In the formula, R represents a hydrogen atom, an alkyl group of 1 to 5 carbon atoms, a halogenated alkyl group of 1 to 5 carbon atoms, a hydroxyalkyl group, an alkoxy group; $Ya^{21}$ represents a single bond or a divalent linking group; $La^{21}$ represents —O—, —COO—, —CON(R')—, —OCO—, —CONHCO— or —CONHCS—; and R' represents a hydrogen atom or a methyl group, provided that, when $La^{21}$ represents —O—, $Ya^{21}$ does not represents —CO—; and $Ra^{21}$ represents a lactone-containing cyclic group, a carbonate-containing cyclic group or an —$SO_2$— containing cyclic group.

The divalent linking group for $Ya^{21}$ is not particularly limited, and preferable examples thereof include a divalent hydrocarbon group which may have a substituent and a divalent linking group containing a hetero atom.

(Divalent Hydrocarbon Group which May have a Substituent)

The hydrocarbon group as a divalent linking group may be either an aliphatic hydrocarbon group or an aromatic hydrocarbon group.

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof. Specifically, groups exemplified above for $Va^1$ in the aforementioned formula (a1-1) can be mentioned.

The linear or branched aliphatic hydrocarbon group may or may not have a substituent. Examples of the substituent include a fluorine atom, a fluorinated alkyl group of 1 to 5 carbon atoms, and a carbonyl group.

As examples of the hydrocarbon group containing a ring in the structure thereof, a cyclic aliphatic hydrocarbon group containing a hetero atom in the ring structure thereof and may have a substituent (a group in which two hydrogen atoms have been removed from an aliphatic hydrocarbon ring), a group in which the cyclic aliphatic hydrocarbon group is bonded to the terminal of the aforementioned chain-like aliphatic hydrocarbon group, and a group in which the cyclic aliphatic group is interposed within the aforementioned linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

Specific examples of the cyclic aliphatic hydrocarbon group include the same group as exemplified above for $Va^1$ in the aforementioned formula (a1-1).

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

Specific examples of the aromatic hydrocarbon group as a divalent hydrocarbon group include the same group as exemplified above for $Va^1$ in the aforementioned formula (a1-1).

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group of 1 to 5 carbon atoms, and a methyl group, an ethyl group, a propyl group, an n-butyl group or a tert-butyl group is particularly desirable.

As the alkoxy group, the halogen atom and the halogenated alkyl group for the substituent, the same groups as the aforementioned substituent groups for substituting a hydrogen atom within the cyclic aliphatic hydrocarbon group can be used.

(Divalent Linking Group Containing a Hetero Atom)

With respect to a divalent linking group containing a hetero atom, a hetero atom is an atom other than carbon and hydrogen, and examples thereof include an oxygen atom, a nitrogen atom, a sulfur atom and a halogen atom.

In the case where $Ya^{21}$ represents a divalent linking group containing a hetero atom, preferable examples of the linking group include —O—, —C(=O)—O—, —C(=O)—, —O—C(=O)—O—, —C(=O)—NH—, —NH—, —NH—C(=NH)— (wherein H may be substituted with a substituent such as an alkyl group or an acyl group), —S—, —S(=O)$_2$—, —S(=O)$_2$—O—, and a group represented by general formula —$Y^{21}$—O—$Y^{22}$—, —$Y^{21}$—O—, —$Y^{21}$—C(=O)—O—, —[$Y^{21}$—C(=O)—O]$_{m'}$—$Y^{22}$— or —$Y^{21}$—O—C(=O)—$Y^{22}$— [in the formulae, $Y^{21}$ and $Y^{22}$ each independently represents a divalent hydrocarbon group which may have a substituent, O represents an oxygen atom, and m' represents an integer of 0 to 3].

The divalent linking group containing a hetero atom represents —C(=O)—NH—, —NH—, or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In formulae —$Y^{21}$—O—$Y^{22}$—, —$Y^{21}$—O—, —$Y^{21}$—C(=O)—O—, —[$Y^{21}$—C(=O)—O]$_{m'}$—$Y^{22}$— and —$Y^{21}$—O—C(=O)—$Y^{22}$—, $Y^{21}$ and $Y^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group.

As $Y^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula —[$Y^{21}$—C(=O)—O]$_{m'}$—$Y^{22}$—, m' represents an integer of 0 to 3, preferably an integer of 0 to 2, more preferably 0 or 1, and most preferably 1. Namely, it is particularly desirable that the group represented by the formula —[$Y^{21}$—C(=O)—O]$_{m'}$—$Y^{22}$— is a group represented by the formula —$Y^{21}$—C(=O)—O—$Y^{22}$—. Among these, a group represented by the formula —$(CH_2)_{a'}$—C(=O)—O—$(CH_2)_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

In the present invention, Ya$^{21}$ preferably represents an ester bond [—C(=O)—O—], an ether bond (—O—), a linear or branched alkylene group, a combination of these, or a single bond.

In formula (a2-1), Ra$^{21}$ represents a lactone-containing cyclic group, a carbonate-containing cyclic group or an —SO$_2$— containing cyclic group.

The term "lactone-containing cyclic group" refers to a cyclic group including a ring containing a —O—C(=O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group for Ra$^{21}$ is not particularly limited, and an arbitrary group may be used.

The lactone-containing cyclic group may have a substituent. Examples of the substituent include an alkyl group, an alkoxy group, a halogen atom, a halogenated alkyl group, a hydroxy group, —COOR", —OC(=O)R", a hydroxyalkyl group and a cyano group (wherein R" represents a hydrogen atom or an alkyl group).

The alkyl group for the substituent is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

As the alkoxy group for the substituent, an alkoxy group of 1 to 6 carbon atoms is preferable. Further, the alkoxy group is preferably a linear or branched alkoxy group. Specific examples of the alkoxy group include the aforementioned alkyl groups for the substituent having an oxygen atom (—O—) bonded thereto.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

As examples of the halogenated alkyl group for the substituent, groups in which part or all of the hydrogen atoms of the aforementioned alkyl groups for the substituent have been substituted with the aforementioned halogen atoms can be given. As the halogenated alkyl group, a fluorinated alkyl group is preferable, and a perfluoroalkyl group is particularly desirable.

In the —COOR" group and the —OC(=O)R" group, R" represents a hydrogen atom or a linear, branched or cyclic alkyl group of 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The hydroxyalkyl group for the substituent preferably has 1 to 6 carbon atoms, and specific examples thereof include the aforementioned alkyl groups for the substituent in which at least one hydrogen atom has been substituted with a hydroxy group.

Specific examples include groups represented by general formulas (a2-r-1) to (a2-r-7) shown below.

[Chemical Formula 30]

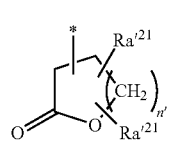
(a2-r-1)

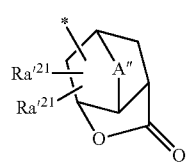
(a2-r-2)

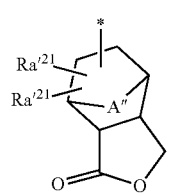
(a2-r-3)

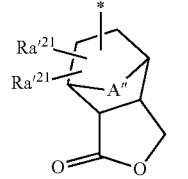
(a2-r-4)

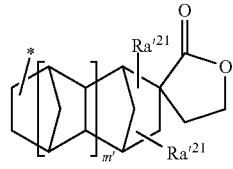
(a2-r-5)

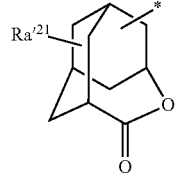
(a2-r-6)

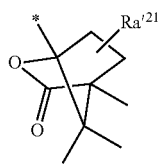
(a2-r-7)

In the formulae, each Ra'²¹ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom or an alkyl group; A" represents an oxygen atom, a sulfur atom or an alkylene group of 1 to 5 carbon atoms which may contain an oxygen atom or a sulfur atom; n' represents an integer of 0 to 2; and m' represents 0 or 1.

In general formulae (a2-r-1) to (a2-r-7) above, A" represents an oxygen atom (—O—), a sulfur atom (—S—) or an alkylene group of 1 to 5 carbon atoms which may contain an oxygen atom or a sulfur atom. As the alkylene group of 1 to 5 carbon atoms for A", a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH₂—, —CH₂—O—CH₂—, —S—CH₂— and —CH₂—S—CH₂—. As A", an alkylene group of 1 to 5 carbon atoms or —O— is preferable, more preferably an alkylene group of 1 to 5 carbon atoms, and most preferably a methylene group. As the alkyl group, alkoxy group, halogenated alkyl group, —COOR", —OC(=O)R" and hydroxyalkyl group for Ra'²¹, the same alkyl groups, alkoxy groups, halogenated alkyl groups, —COOR", —OC(=O)R" and hydroxyalkyl groups as those described above as the substituent for the —SO₂— containing cyclic group can be mentioned.

Specific examples of the groups represented by the aforementioned general formulae (a2-r-1) to (a2-r-7) are shown below.

[Chemical Formula 31]

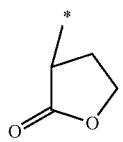
(r-lc-1-1)

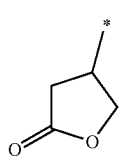
(r-lc-1-2)

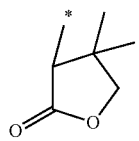
(r-lc-1-3)

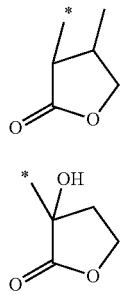
(r-lc-1-4)

(r-lc-1-5)

(r-lc-1-6)

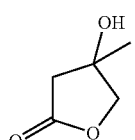
(r-lc-1-7)

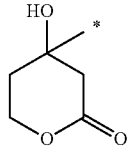
(r-lc-3-1)

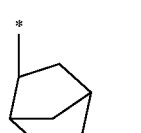
(r-lc-3-2)

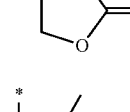
(r-lc-3-3)

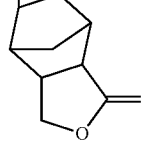
(r-lc-3-4)

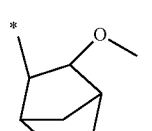

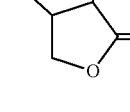

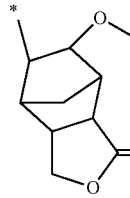

(r-lc-3-5)
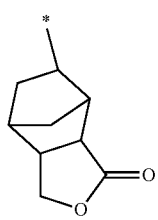
(r-lc-2-1)
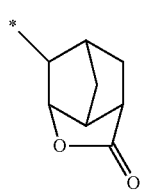
(r-lc-2-2)
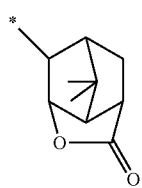
(r-lc-2-3)
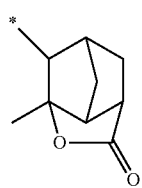
(r-lc-2-4)
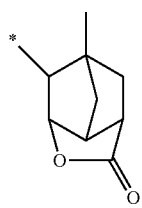
(r-lc-2-5)
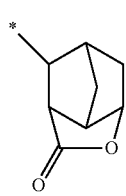
(r-lc-2-6)
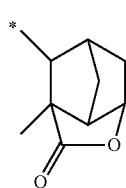
(r-lc-2-7)
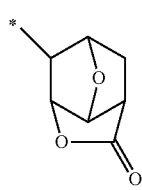
(r-lc-2-8)
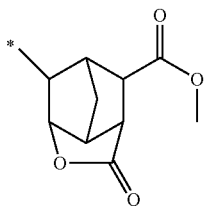
(r-lc-2-9)
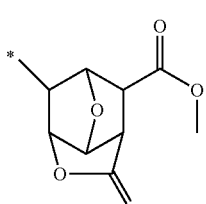
(r-lc-2-10)
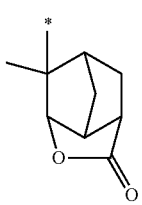
(r-lc-2-11)
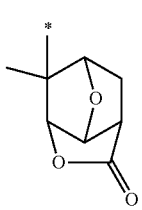
(r-lc-2-12)
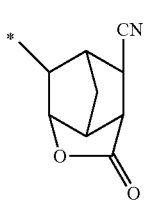
(r-lc-2-13)
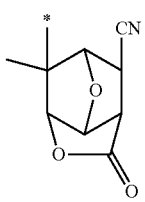
(r-lc-4-1)
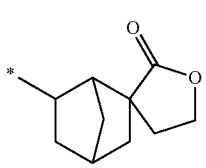
(r-lc-4-2)
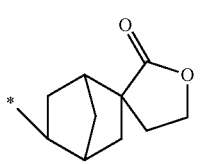

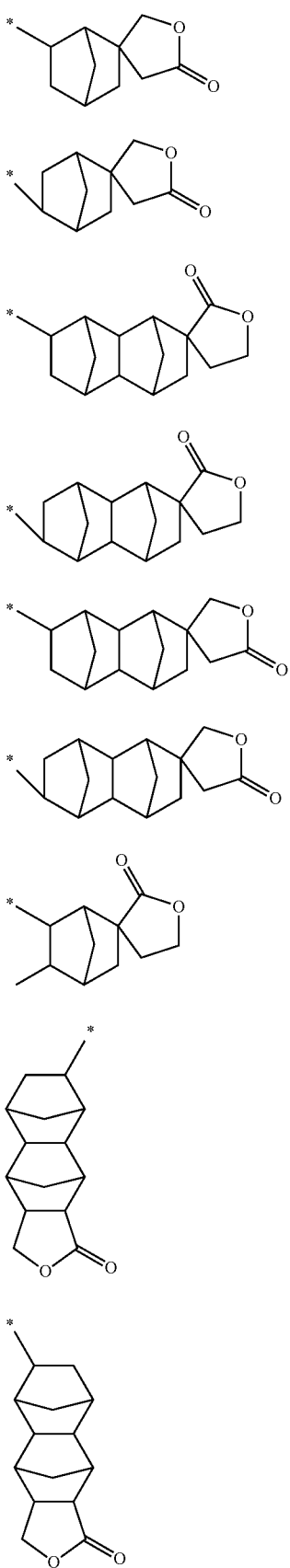
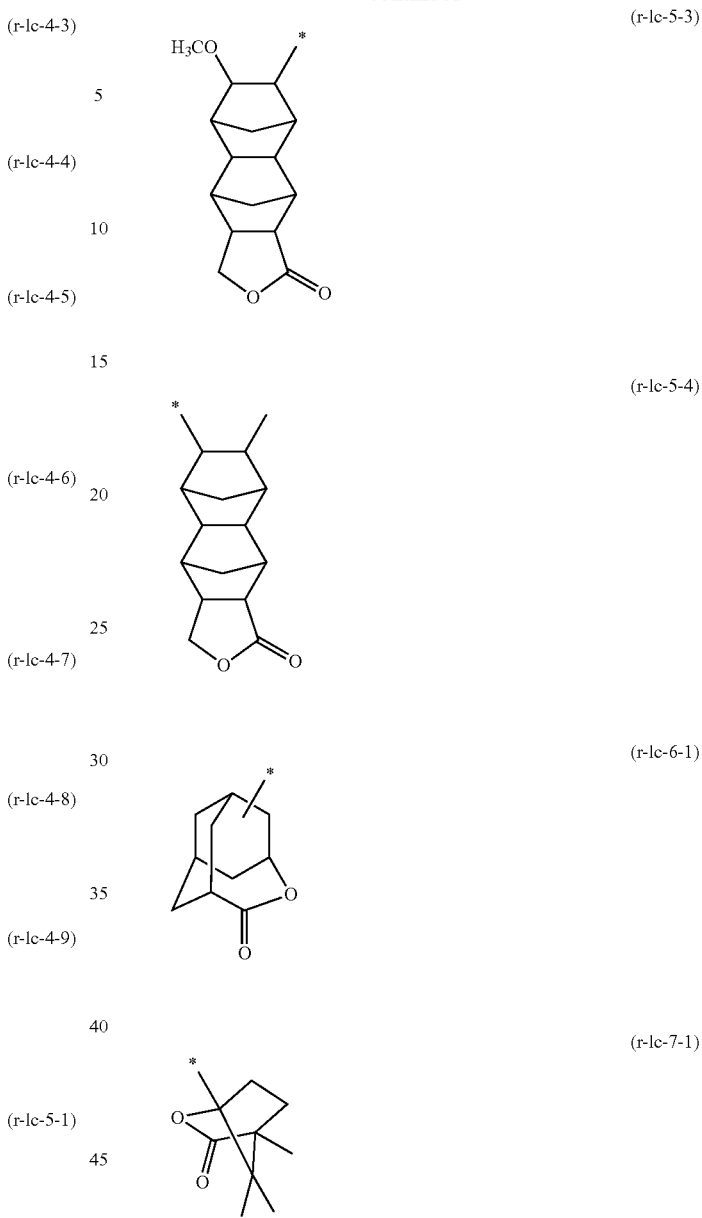

Among the above examples, as the lactone-containing cyclic group, a group represented by the aforementioned general formula (a2-r-1) is preferable, a group represented by any one of the aforementioned chemical formula (r-lc-1-1) to (r-lc-1-7) is more preferable, and a group represented by the aforementioned formula (r-lc-1-1) is still more preferable.

The term "carbonate-containing cyclic group" refers to a cyclic group including a ring containing a —O—C(=O)—O— structure (carbonate ring). The term "carbonate ring" refers to a single ring containing a —O—C(=O)—O— structure, and this ring is counted as the first ring. A carbonate-containing cyclic group in which the only ring structure is the carbonate ring is referred to as a monocyclic group, and groups containing other ring structures are described as polycyclic groups regardless of the structure of the other rings. The carbonate-containing cyclic group may be either a monocyclic group or a polycyclic group.

The carbonate-containing cyclic group for $Ra^{21}$ is not particularly limited, and an arbitrary group may be used. Specific examples include groups represented by general formulas (ax3-r-1) to (ax3-r-3) shown below.

[Chemical Formula 32]

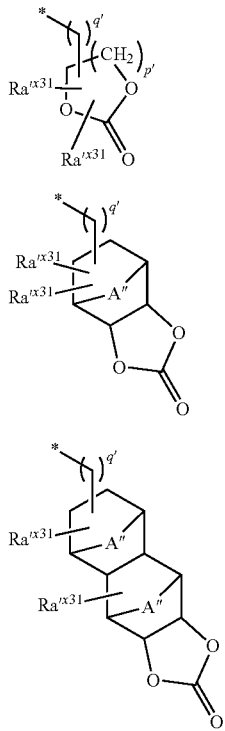

(ax3-r-1)

(ax3-r-2)

(ax3-r-3)

In the formulae, each Ra'$^{\prime x31}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom or an alkyl group; A" represents an oxygen atom, a sulfur atom or an alkylene group of 1 to 5 carbon atoms which may contain an oxygen atom or a sulfur atom; q' represents 0 or 1; and * represents a valence bond.

In general formulae (ax3-r-1) to (ax3-r-3), A" is the same as defined for A" in general formulae (a2-r-1) to (a2-r-7). The alkyl group, alkoxy group, halogen atom, halogenated alkyl group, —COOR", —OC(=O)R" and hydroxyalkyl group for Ra'$^{\prime x31}$ in the aforementioned formulae (ax3-r-1) to (ax3-r-3) are the same as defined for Ra'$^{21}$ in the aforementioned general formulae (a2-r-1) to (a2-r-7).

Specific examples of the groups represented by the aforementioned general formulae (ax3-r-1) to (ax3-r-3) are shown below.

[Chemical Formula 33]

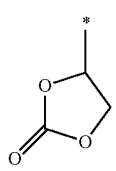

(r-cr-1-1)

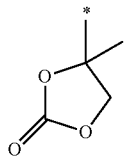

(r-cr-1-2)

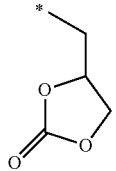

(r-cr-1-3)

(r-cr-1-4)

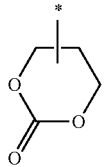

(r-cr-1-5)

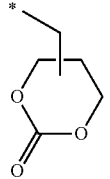

(r-cr-1-6)

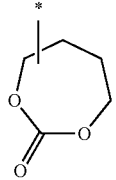

(r-cr-1-6)

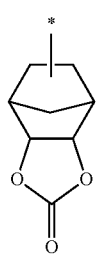

(r-cr-2-1)

(r-cr-2-2)

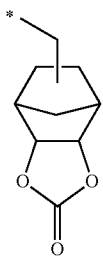

(r-cr-2-3)

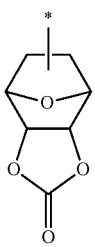

(r-cr-2-4)

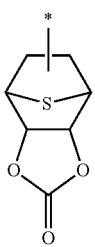

(r-cr-3-1)

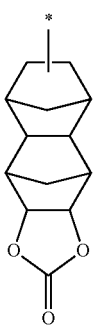

(r-cr-3-2)

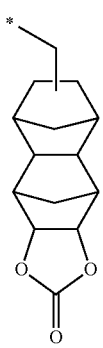

(r-cr-3-3)

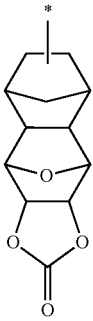

(r-cr-3-4)

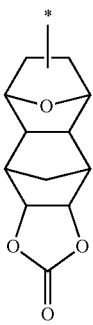

(r-cr-3-5)

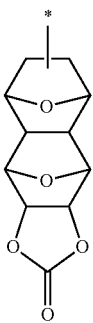

Here, an "—$SO_2$— containing cyclic group" for $Ra^{21}$ refers to a cyclic group having a ring containing —$SO_2$— within the ring structure thereof, i.e., a cyclic group in which the sulfur atom (S) within —$SO_2$— forms part of the ring skeleton of the cyclic group. The ring containing —$SO_2$— within the ring skeleton thereof is counted as the first ring. A cyclic group in which the only ring structure is the ring that contains —$SO_2$— in the ring skeleton thereof is referred to as a monocyclic group, and a group containing other ring structures is described as a polycyclic group regardless of the structure of the other rings. The —$SO_2$— containing cyclic group may be either a monocyclic group or a polycyclic group.

As the —$SO_2$— containing cyclic group, a cyclic group containing —O—$SO_2$— within the ring skeleton thereof, i.e., a cyclic group containing a sultone ring in which —O—S— within the —O—$SO_2$— group forms part of the ring skeleton thereof is particularly desirable.

The —$SO_2$— containing cyclic group may have a substituent. Examples of the substituent include an alkyl group, an alkoxy group, a halogen atom, a halogenated alkyl group, a hydroxy group, —COOR″, —OC(=O)R″, a hydroxyalkyl group and a cyano group (wherein R″ represents a hydrogen atom or an alkyl group).

The alkyl group for the substituent is preferably an alkyl group of 1 to 6 carbon atoms. Further, the alkyl group is preferably a linear alkyl group or a branched alkyl group.

Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

As the alkoxy group for the substituent, an alkoxy group of 1 to 6 carbon atoms is preferable. Further, the alkoxy group is preferably a linear or branched alkoxy group. Specific examples of the alkoxy group include the aforementioned alkyl groups for the substituent having an oxygen atom (—O—) bonded thereto.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

As examples of the halogenated alkyl group for the substituent, groups in which part or all of the hydrogen atoms of the aforementioned alkyl groups for the substituent have been substituted with the aforementioned halogen atoms can be given. As the halogenated alkyl group, a fluorinated alkyl group is preferable, and a perfluoroalkyl group is particularly desirable.

In the —COOR" group and the —OC(=O)R" group, R" represents a hydrogen atom or a linear, branched or cyclic alkyl group of 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The hydroxyalkyl group for the substituent preferably has 1 to 6 carbon atoms, and specific examples thereof include the aforementioned alkyl groups for the substituent in which at least one hydrogen atom has been substituted with a hydroxy group.

More specific examples of the —SO$_2$— containing cyclic group include groups represented by general formulas (a5-r-1) to (a5-r-4) shown below.

[Chemical Formula 34]

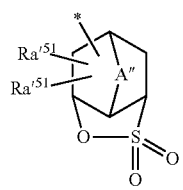

(a5-r-1)

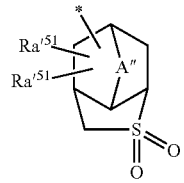

(a5-r-2)

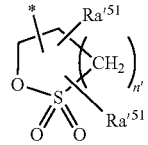

(a5-r-3)

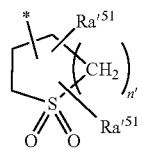

(a5-r-4)

In the formulae, each Ra'$^{51}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom or an alkyl group; A" represents an oxygen atom, a sulfur atom or an alkylene group of 1 to 5 carbon atoms which may contain an oxygen atom or a sulfur atom; and n' represents an integer of 0 to 2.

In general formulae (a5-r-1) to (a5-r-4), A" is the same as defined for A" in general formulae (a2-r-1) to (a2-r-7). The alkyl group, alkoxy group, halogen atom, halogenated alkyl group, —COOR", —OC(=O)R" and hydroxyalkyl group for Ra'$^{51}$ are the same as defined for Ra'$^{21}$ in the aforementioned general formulae (a2-r-1) to (a2-r-7).

Specific examples of the groups represented by the aforementioned general formulas (a5-r-1) to (a5-r-4) are shown below. In the formulae shown below, "Ac" represents an acetyl group.

[Chemical Formula 35]

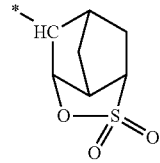

(r-sl-1-1)

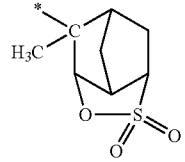

(r-sl-1-2)

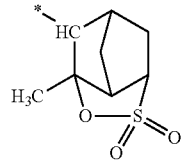

(r-sl-1-3)

-continued
(r-sl-1-4)
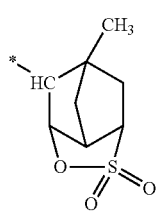
(r-sl-1-5)
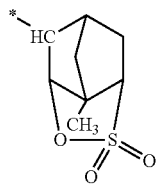
(r-sl-1-6)
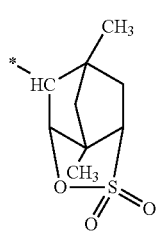
(r-sl-1-7)
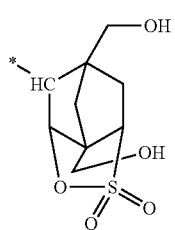
(r-sl-1-8)
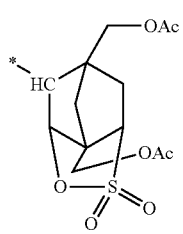
(r-sl-1-9)
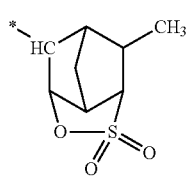
(r-sl-1-10)
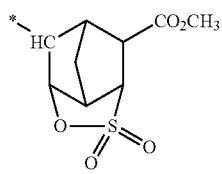
(r-sl-1-11)
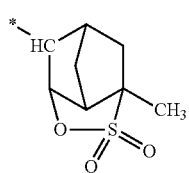
-continued
(r-sl-1-12)
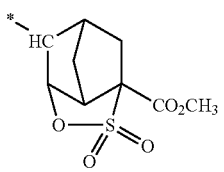
(r-sl-1-13)
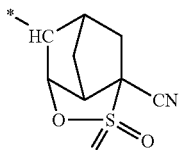
(r-sl-1-14)
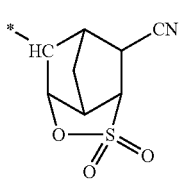
(r-sl-1-15)
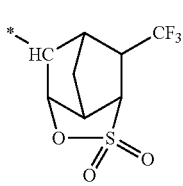
(r-sl-1-16)
(r-sl-1-17)
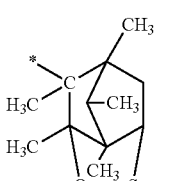
(r-sl-1-18)
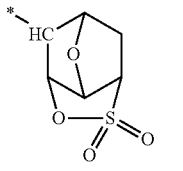
(r-sl-1-19)
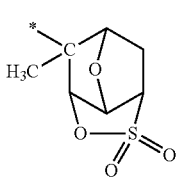
(r-sl-1-20)

-continued
(r-sl-1-21)
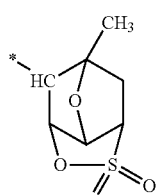
[Chemical Formula 36]
(r-sl-1-22)
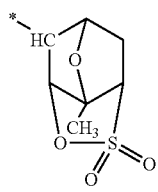
(r-sl-1-23)
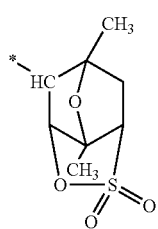
(r-sl-1-24)
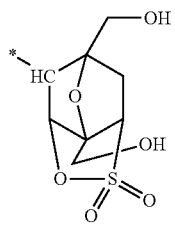
(r-sl-1-25)
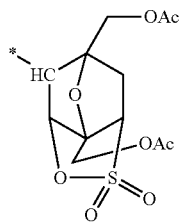
(r-sl-1-26)
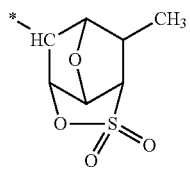
(r-sl-1-27)
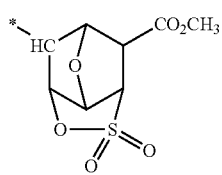
-continued
(r-sl-1-28)
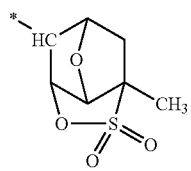
(r-sl-1-29)
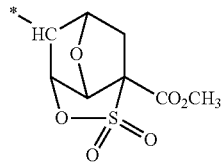
(r-sl-1-30)
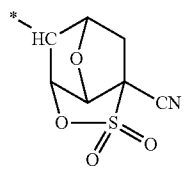
(r-sl-1-31)
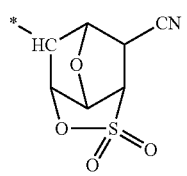
(r-sl-1-32)
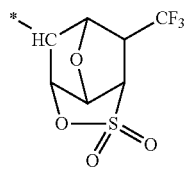
(r-sl-1-33)
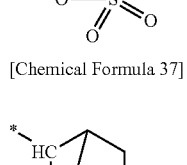
[Chemical Formula 37]
(r-sl-2-1)
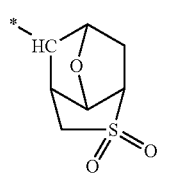
(r-sl-2-2)
(r-sl-3-1)
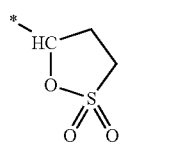

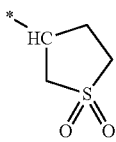

(r-sl-4-1)

Among the above examples, as the —SO$_2$— containing cyclic group, a group represented by the aforementioned general formula (a5-r-1) is preferable, and a group represented by the aforementioned chemical formula (r-sl-1-1) or (r-sl-1-18) is more preferable.

As the structural unit (a2) contained in the component (A1), 1 type of structural unit may be used, or 2 or more types may be used.

When the component (A1) contains the structural unit (a2), the amount of the structural unit (a2) based on the combined total of all structural units constituting the component (A1) is preferably 1 to 80 mol %, more preferably 10 to 70 mol %, still more preferably 10 to 65 mol %, and most preferably 10 to 60 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units, and various lithography properties such as DOF and CDU and pattern shape can be improved.

(Structural Unit (a3))

The component (A1) may contain a structural unit (a3). The structural unit (a3) is a structural unit containing a polar group-containing aliphatic hydrocarbon group (provided that the structural units that fall under the definition of structural units (a1), (a0) and (a2) are excluded).

When the component (A1) includes the structural unit (a3), it is presumed that the hydrophilicity of the component (A1) is enhanced, thereby contributing to improvement in resolution.

Examples of the polar group include a hydroxyl group, cyano group, carboxyl group, or hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups can be selected appropriately from the multitude of groups that have been proposed for the resins of resist compositions designed for use with ArF excimer lasers. The cyclic group is preferably a polycyclic group, more preferably a polycyclic group of 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylate ester which may have the hydrogen atom bonded to the carbon atom on the α-position substituted with a substituent and contains a polar group-containing aliphatic hydrocarbon group.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 38]

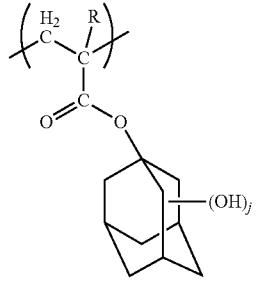

(a3-1)

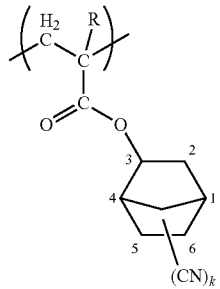

(a3-2)

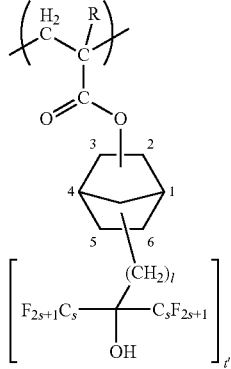

(a3-3)

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1.1 is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3) contained in the component (A1), 1 type of structural unit may be used, or 2 or more types may be used.

In the component (A1), the amount of the structural unit (a3) based on the combined total of all structural units constituting the component (A1) is preferably 5 to 50 mol %, more preferably 5 to 40 mol %, and still more preferably 5 to 25 mol %.

When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

(Structural Unit (a4))

If desired, the component (A1) may further include a structural unit (a4) containing an acid non-dissociable cyclic group. When the component (A1) includes the structural unit (a4), dry etching resistance of the resist pattern to be formed is improved. Further, the hydrophobicity of the component (A1) is further improved. Increase in the hydrophobicity contributes to improvement in terms of resolution, shape of the resist pattern and the like, particularly in an organic solvent developing process.

An "acid non-dissociable, aliphatic cyclic group" in the structural unit (a4) refers to a cyclic group which is not dissociated by the action of acid generated from the component (B) described later upon exposure, and remains in the structural unit.

As the structural unit (a4), a structural unit which contains a non-acid-dissociable aliphatic cyclic group, and is also derived from an acrylate ester is preferable. Examples of this cyclic group include the same groups as those described above in relation to the aforementioned structural unit (a1), and any of the multitude of conventional groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecyl group, adamantyl group, tetracyclododecyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-6) shown below.

[Chemical Formula 39]

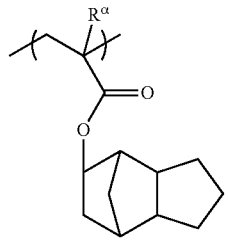

(a4-1)

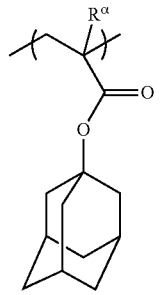

(a4-2)

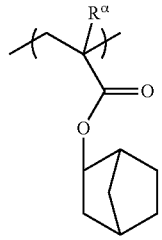

(a4-3)

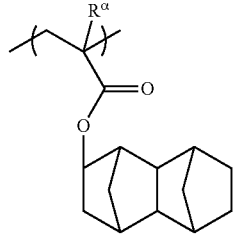

(a4-4)

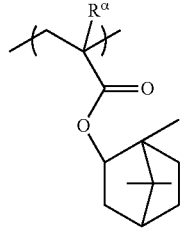

(a4-5)

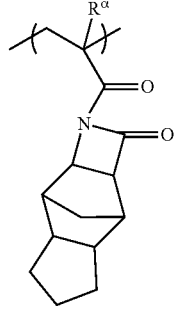

(a4-6)

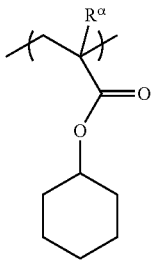

(a4-7)

In the formulae, $R^\alpha$ is the same as defined above.

As the structural unit (a4) contained in the component (A1), 1 type of structural unit may be used, or 2 or more types may be used.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

As the component (A1), a copolymer having at least the structural unit (a1) is preferable, a copolymer having a structural unit (a2) or (a3) in addition to the structural unit (a1)) is more preferable, and a copolymer having the structural units (a1), (a2) and (a3) is still more preferable.

The component (A1) can be obtained, for example, by a conventional radical polymerization or the like of the monomers corresponding with each of the structural units, using a radical polymerization initiator such as azobisisobutyronitrile (AIBN) or dimethyl 2,2'-azobis(isobutyrate).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (A1) is not particularly limited, but is preferably 1,000 to 50,000, more preferably 1,500 to 30,000, and most preferably 2,500 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (A1) is not particularly limited, but is preferably 1.0 to 5.0, more preferably 1.0 to 3.0, and most preferably 1.2 to 2.5.

Here, Mn is the number average molecular weight.

As the component (A1), one type may be used alone, or two or more types may be used in combination.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, various lithography properties are improved, such as improvement in MEF and circularity, and reduction of roughness.

[Component (A2)]

In the resist composition of the present invention, the component (A) may contain "a base component which exhibits increased polarity under action of acid" other than the component (A1) (hereafter, referred to as "component (A2)").

The component (A2) is not particularly limited, and any of the multitude of conventional base components used within chemically amplified resist compositions (e.g., base resins used within chemically amplified resist compositions for ArF excimer lasers or KrF excimer lasers, preferably ArF excimer lasers) can be used. For example, as a base resin for ArF excimer laser, a base resin having the aforementioned structural unit (a1) as an essential component, and optionally the aforementioned structural units (a2) to (a4) can be used.

As the component (A2), one type of resin may be used, or two or more types of resins may be used in combination.

In the resist composition of the present invention, as the component (A), one type may be used, or two or more types of compounds may be used in combination.

In the resist composition of the present invention, the amount of the component (A) can be appropriately adjusted depending on the thickness of the resist film to be formed, and the like.

<Acid Generator Component; Component (B)>

The resist composition of the present invention preferably contains an acid generator component (B) (hereafter, referred to as "component (B)") which generates acid upon exposure. The acid generator component (B) preferably contains an acid generator (B1) represented by general formula (b1-1) shown below.

[Chemical Formula 40]

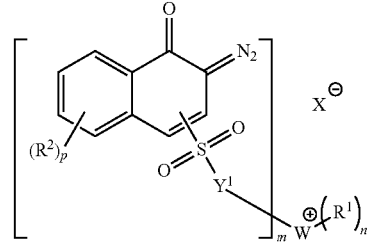

(b1-1)

In the formula, $Y^1$ represents a divalent linking group; W represents S, Se or I; $R^1$ represents a hydrocarbon group which may have a substituent; $R^2$ represents an alkyl group of 1 to 5 carbon atoms or an alkoxy group of 1 to 5 carbon atoms; when W represents I, m+n=2, and when W represents S or Se, m+n=3, provided that m≥1 and n≥0; p represents an integer of 0 to 5; and $X^-$ represents a counteranion.

In general formula (b1-1), the divalent linking group for $Y^1$, the hydrocarbon group for $R^1$ which may have a substituent, the alkyl group of 1 to 5 carbon atoms or alkoxy group of 1 to 5 carbon atoms for $R^2$ and the counteranion for $X^-$ are the same as defined in general formula (b1).

In the component (B), as the component (B1), one kind of the aforementioned compound may be used, or two or more kinds of compounds may be used in combination.

In the resist composition, the amount of the component (B1) relative to 100 parts by weight of the component (A) is preferably within a range from 0.5 to 60 parts by weight, more preferably from 1 to 50 parts by weight, still more preferably from 1 to 40 parts by weight, and most preferably from 1 to 30 parts by weight. When the amount is within the above-mentioned range, further improved lithography properties can be obtained. Further, by virtue of the above-mentioned range, when each of the components are dissolved in an organic solvent, a uniform solution can be obtained and the storage stability becomes satisfactory.

<Optional Components>

[Component (B2)]

The resist composition of the present invention preferably contains, in addition to the component (B1), a component (B2) described below as the component (B). As the component (B2), there is no particular limitation, and any of the known acid generators used in conventional chemically amplified resist compositions can be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators. Among these, it is preferable to use an onium salt acid generator.

As the onium salt acid generator, a compound represented by general formula (b-1) below (hereafter, sometimes referred to as "component (b-1)"), a compound represented by general formula (b-2) below (hereafter, sometimes referred to as "component (b-2)") or a compound represented by general formula (b-3) below (hereafter, sometimes referred to as "component (b-3)") may be used.

[Chemical Formula 41]

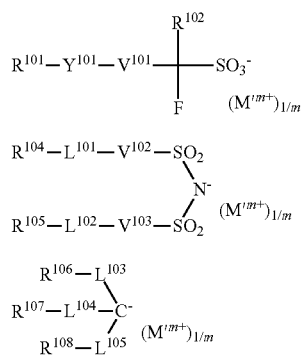

In the formulae, $R^{101}$ and $R^{104}$ to $R^{108}$ each independently represents a cyclic group which may have a substituent, a chain-like alkyl group which may have a substituent or a chain-like alkenyl group which may have a substituent, provided that $R^{104}$ and $R^{105}$ may be mutually bonded to form a ring, and $R^{106}$ and $R^{107}$ may be mutually bonded to form a ring; $R^{102}$ represents a fluorine atom or a fluorinated alkyl group of 1 to 5 carbon atoms; $Y^{101}$ represents a single bond or a divalent linking group containing an oxygen atom; $V^{101}$ to $V^{103}$ each independently represents a single bond, an alkylene group or a fluorinated alkylene group; $L^{101}$ and $L^{102}$ each independently represents a single bond or an oxygen atom; $L^{103}$ to $L^{105}$ each independently represents a single bond, —CO— or —SO$_2$—; and $M^{'m+}$ represents an organic cation having a valency of m (provided that the cation of a compound represented by the aforementioned formula (b1-1) is excluded).

{Anion Moiety}

Anion Moiety of Component (b-1)

In the formula (b-1), $R^{101}$ represents a cyclic group which may have a substituent, a chain-like alkyl group which may have a substituent or a chain-like alkenyl group which may have a substituent.

(Cyclic Group which May have a Substituent)

The cyclic group is preferably a cyclic hydrocarbon group, and the cyclic hydrocarbon group may be either an aromatic hydrocarbon group or an aliphatic hydrocarbon group.

As the aromatic hydrocarbon group for $R^{101}$, groups in which one hydrogen atom has been removed from an aromatic hydrocarbon ring described above in relation to the divalent aromatic hydrocarbon group for Va$^1$ in the formula (a1-1) or an aromatic compound containing two or more aromatic ring can be mentioned, and a phenyl group or a naphthyl group is preferable.

As the cyclic aliphatic hydrocarbon group for $R^{101}$, groups in which one hydrogen atom has been removed from a monocycloalkane or a polycycloalkane exemplified above in the explanation of the divalent aliphatic hydrocarbon group for Va$^1$ in the formula (a1-1) can be mentioned, and an adamantyl group or a norbornyl group is preferable.

Further, the cyclic hydrocarbon group for $R^{101}$ may contain a hetero atom like as a heterocycle, and specific examples thereof include lactone-containing cyclic groups represented by the aforementioned general formulas (a2-r-1) to (a2-r-7), —SO$_2$— containing cyclic groups represented by the aforementioned formulas (a5-r-1) to (a5-r-4) and heterocycles shown below.

[Chemical Formula 42]

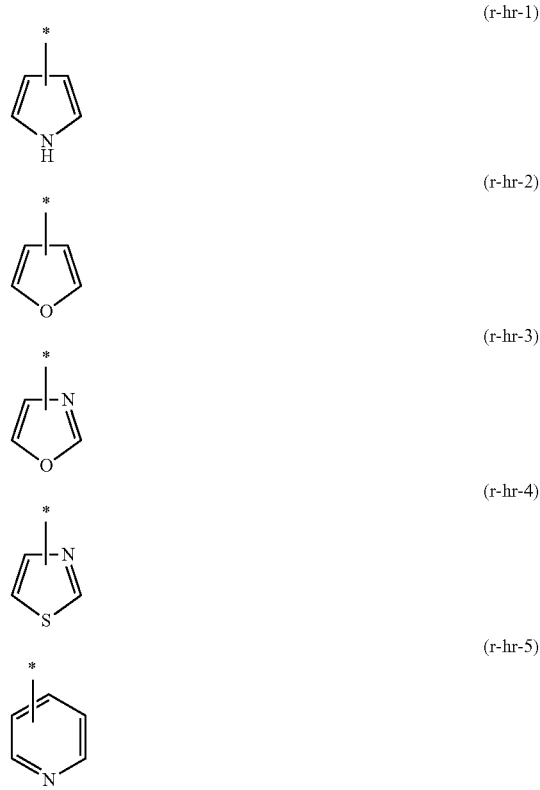

-continued (r-hr-6) 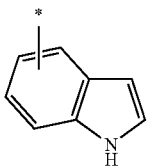
(r-hr-7) 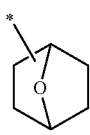
(r-hr-8) 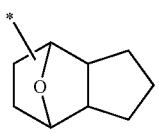
(r-hr-9) 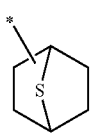
(r-hr-10) 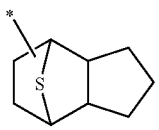
(r-hr-11) 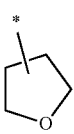
(r-hr-12) 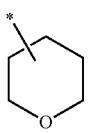
(r-hr-13) 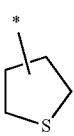
(r-hr-14) 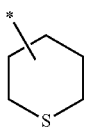
(r-hr-15) 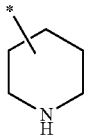

-continued (r-hr-16) 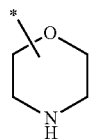

As the substituent for the cyclic hydrocarbon group for $R^{101}$, an alkyl group, an alkoxy group, a halogen atom, a halogenated alkyl group, a hydroxyl group, a carbonyl group, a nitro group or the like can be used.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

(Chain-Like Alkyl Group which May have a Substituent)

The chain-like alkyl group for $R^{101}$ may be linear or branched.

The linear alkyl group preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

(Chain-Like Alkenyl Group which May have a Substituent)

The chain-like alkenyl group for $R^{101}$ may be linear or branched, and preferably has 2 to 10 carbon atoms, more preferably 2 to 5 carbon atoms, still more preferably 2 to 4 carbon atoms, and most preferably 3 carbon atoms. Examples of linear alkenyl groups include a vinyl group, a propenyl group (an allyl group) and a butynyl group. Examples of branched alkenyl groups include a 1-methylpropenyl group and a 2-methylpropenyl group.

Among the above-mentioned examples, as the chain-like alkenyl group, a propenyl group is particularly desirable.

As the substituent for the chain-like alkyl group or alkenyl group for $R^{101}$, an alkoxy group, a halogen atom, a halogenated alkyl group, a hydroxyl group, a carbonyl group, a nitro group, an amino group, a cyclic group for $R^{101}$ or the like can be used.

Among these examples, as $R^{101}$, a cyclic group which may have a substituent is preferable, and a cyclic hydrocarbon group which may have a substituent is more preferable. Specifically, a phenyl group, a naphthyl group, a group in which one or more hydrogen atoms have been removed from a polycycloalkane, a lactone-containing cyclic group represented by any one of the aforementioned formula (a2-r-1) to (a2-r-7), and an —$SO_2$— containing cyclic group represented by any one of the aforementioned formula (a5-r-1) to (a5-r-4).

In formula (b-1), $Y^{101}$ represents a single bond or a divalent linking group containing an oxygen atom.

In the case where $Y^{101}$ is a divalent linking group containing an oxygen atom, $Y^{101}$ may contain an atom other than an oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an oxycarbonyl group (—O—C(=O)—), an amido bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group. Furthermore, the combinations may have a sulfonyl group (—$SO_2$—) bonded thereto. As the combination, the linking group represented by formulas (y-al-1) to (y-al-7) shown below can be mentioned.

[Chemical Formula 43]

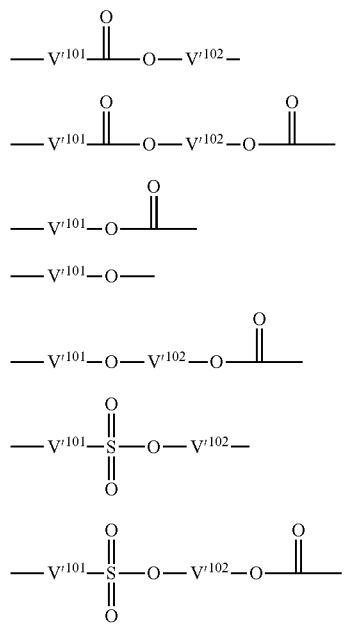

In the formulae, $V'^{101}$ represents a single bond or an alkylene group of 1 to 5 carbon atoms; $V'^{102}$ represents a divalent saturated hydrocarbon group of 1 to 30 carbon atoms.

The divalent saturated hydrocarbon group for $V'^{102}$ is preferably an alkylene group of 1 to 30 carbon atoms.

The alkylene group for $V'^{101}$ and $V'^{102}$ may be a linear alkylene group or a branched alkylene group, and a linear alkylene group is preferable.

Specific examples of the alkylene group for $V'^{101}$ and $V'^{102}$ include a methylene group [—$CH_2$—]; an alkylmethylene group, such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; an ethylene group [—$CH_2CH_2$—]; an alkylethylene group, such as —CH($CH_3$)$CH_2$—, —CH($CH_3$)CH($CH_3$)—, —C($CH_3$)$_2CH_2$— and —CH($CH_2CH_3$)$CH_2$—; a trimethylene group (n-propylene group) [—$CH_2CH_2CH_2$—]; an alkyltrimethylene group, such as —CH($CH_3$)$CH_2CH_2$— and —$CH_2$CH($CH_3$)$CH_2$—; a tetramethylene group [—$CH_2CH_2CH_2CH_2$—]; an alkyltetramethylene group, such as —CH($CH_3$)$CH_2CH_2CH_2$—, —$CH_2$CH($CH_3$)$CH_2CH_2$—; and a pentamethylene group [—$CH_2CH_2CH_2CH_2CH_2$—].

Further, part of methylene group within the alkylene group for $V'^{101}$ and $V'^{102}$ may be substituted with a divalent aliphatic cyclic group of 5 to 10 carbon atoms. The aliphatic cyclic group is preferably a divalent group in which one hydrogen atom has been removed from the cyclic aliphatic hydrocarbon group for $Ra^{3}$ in the aforementioned formula (a1-r-1), and a cyclohexylene group, 1,5-adamantylene group or 2,6-adamantylene group is preferable.

$Y^{101}$ is preferably a divalent linking group containing an ether bond or an ester bond, and groups represented by the aforementioned formulas (y-al-1) to (y-al-5) are preferable.

In formula (b-1), $V^{101}$ represents a single bond, an alkylene group or a fluorinated alkylene group. The alkylene group and the fluorinated alkylene group for $V^{101}$ preferably has 1 to 4 carbon atoms. Examples of the fluorinated alkylene group for $V^{101}$ include a group in which part or all of the hydrogen atoms within the alkylene group for $V^{101}$ have been substituted with fluorine. Among these examples, as $V^{101}$, a single bond or a fluorinated alkylene group of 1 to 4 carbon atoms is preferable.

In formula (b-1), $R^{102}$ represents a fluorine atom or a fluorinated alkyl group of 1 to 5 carbon atoms. $R^{102}$ is preferably a fluorine atom or a perfluoroalkyl group of 1 to 5 carbon atoms, and more preferably a fluorine atom.

As specific examples of anion moieties of the formula (b-1), in the case where $Y^{101}$ a single bond, a fluorinated alkylsulfonate anion such as a trifluoromethanesulfonate anion or a perfluorobutanesulfonate anion can be mentioned; and in the case where $Y^{101}$ represents a divalent linking group containing an oxygen atom, anions represented by formulae (an-1) to (an-3) shown below can be mentioned.

[Chemical Formula 44]

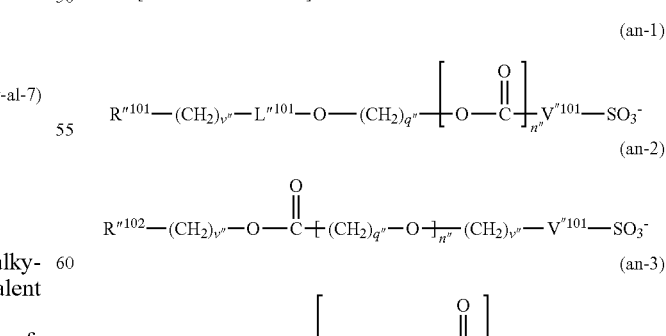

In the formulae, $R'''^{101}$ represents an aliphatic cyclic group which may have a substituent, a group represented by any one of the aforementioned formulae (r-hr-1) to (r-hr-6) or a chain-like alkyl group which may have a substituent; R″¹⁰² represents an aliphatic cyclic group which may have a substituent, a lactone-containing cyclic group represented by any one of the aforementioned formulae (a2-r-1) to (a2-r-7) or an —SO₂— containing cyclic group represented by any one of the aforementioned formulae (a5-r-1) to (a5-r-4); R″¹⁰³ represents an aromatic cyclic group which may have a substituent, an aliphatic cyclic group which may have a substituent or a chain-like alkenyl group which may have a substituent; V″¹⁰¹ represents a fluorinated alkylene group; L″¹⁰¹ represents —C(=O)— or —SO₂—; v″ represents an integer of 0 to 3; q″ represents an integer of 1 to 20; and n″ represents 0 or 1.

As the aliphatic cyclic group for R″¹⁰¹, R″¹⁰² and R″¹⁰³ which may have a substituent, the same groups as the cyclic aliphatic hydrocarbon group for R¹⁰¹ described above are preferable. As the substituent, the same groups as those described above for substituting the cyclic aliphatic hydrocarbon group for R¹⁰¹ can be mentioned.

As the aromatic cyclic group for R″¹⁰³ which may have a substituent, the same groups as the aromatic hydrocarbon group for the cyclic hydrocarbon group represented by R¹⁰¹ described above are preferable. The substituent is the same as defined for the substituent for the aromatic hydrocarbon group represented by R¹⁰¹.

As the chain-like alkyl group for R″¹⁰¹ which may have a substituent, the same groups as those described above for R¹⁰¹ are preferable. As the chain-like alkenyl group for R″¹⁰³ which may have a substituent, the same groups as those described above for R¹⁰¹ are preferable.

V″¹⁰¹ is preferably a fluorinated alkylene group of 1 to 3 carbon atoms, and most preferably —CF₂—, —CF₂CF₂—, —CHFCF₂—, —CF(CF₃)CF₂— or —CH(CF₃)CF₂—.

Specific examples of the anion represented by general formula (an-1) are shown below. However, the present invention is not limited to these examples.

[Chemical Formula 45]

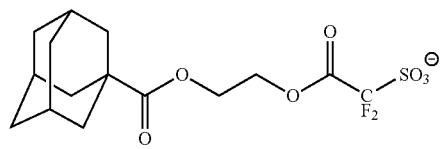
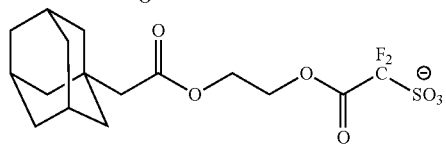
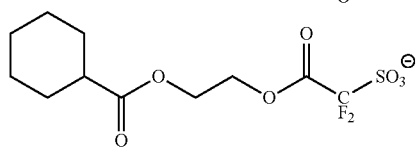
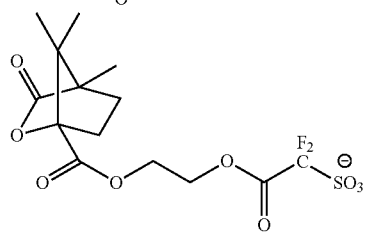
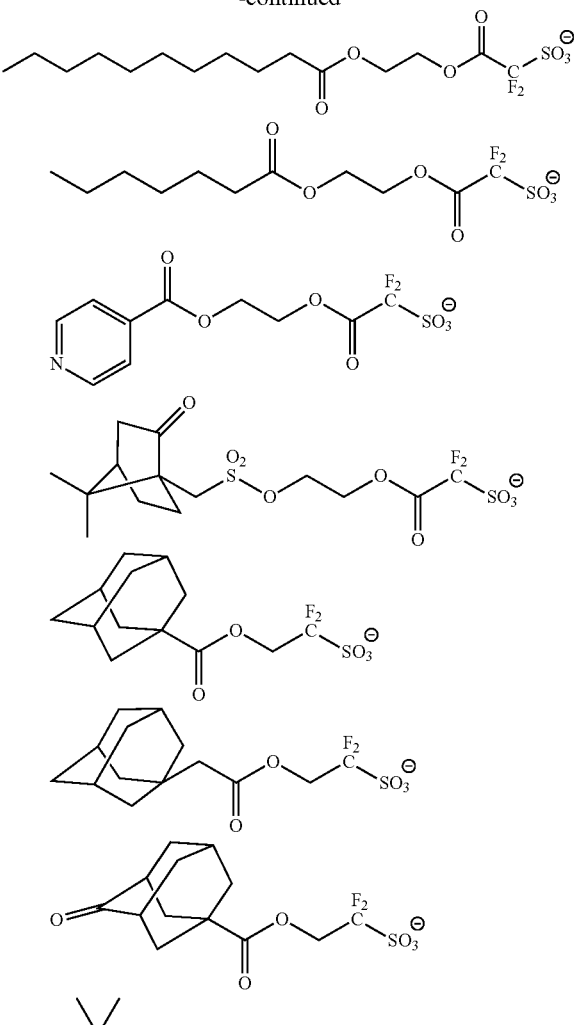

Specific examples of the anion represented by general formula (an-2) are shown below. However, the present invention is not limited to these examples.

[Chemical Formula 46]

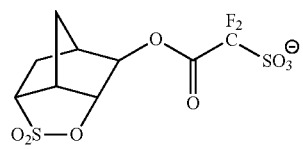

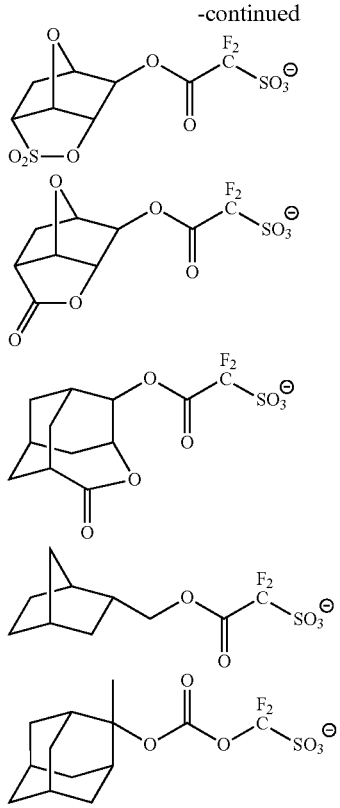

Specific examples of the anion represented by general formula (an-3) are shown below. However, the present invention is not limited to these examples.

[Chemical Formula 47]

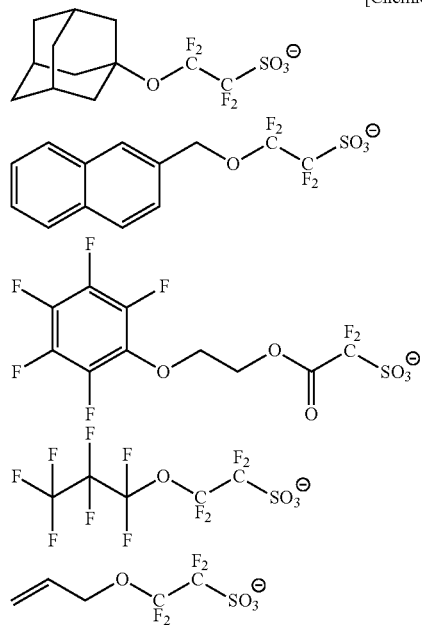

Anion Moiety of Component (b-2)

In formula (b-2), $R^{104}$ and $R^{105}$ each independently represents a cyclic group which may have a substituent, a chain-like alkyl group which may have a substituent or a chain-like alkenyl group which may have a substituent, and is the same as defined for $R^{101}$ in formula (b-1). $R^{104}$ and $R^{105}$ may be mutually bonded to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, more preferably 1 to 7 carbon atoms, and still more preferably 1 to 3 carbon atoms. The smaller the number of carbon atoms of the chain-like alkyl group for $R^{104}$ and $R^{105}$, the more the solubility in a resist solvent is improved. Further, in the chain-like alkyl group for $R^{104}$ and $R^{105}$, it is preferable that the number of hydrogen atoms substituted with fluorine atoms is as large as possible because the acid strength increases and the transparency to high energy radiation of 200 nm or less or electron beam is improved. The fluorination ratio of the chain-like alkyl group is preferably from 70 to 100%, more preferably from 90 to 100%, and it is particularly desirable that the chain-like alkyl group be a perfluoroalkyl group in which all hydrogen atoms are substituted with fluorine atoms.

In formula (b-2), $V^{102}$ and $V^{103}$ each independently represents a single bond, an alkylene group or a fluorinated alkylene group, and is the same as defined for $V^{101}$ in formula (b-1).

In formula (b-2), $L^{101}$ and $L^{102}$ each independently represents a single bond or an oxygen atom.

Specific examples of the anion represented by general formula (b-2) are shown below. However, the present invention is not limited to these examples.

[Chemical Formula 48]

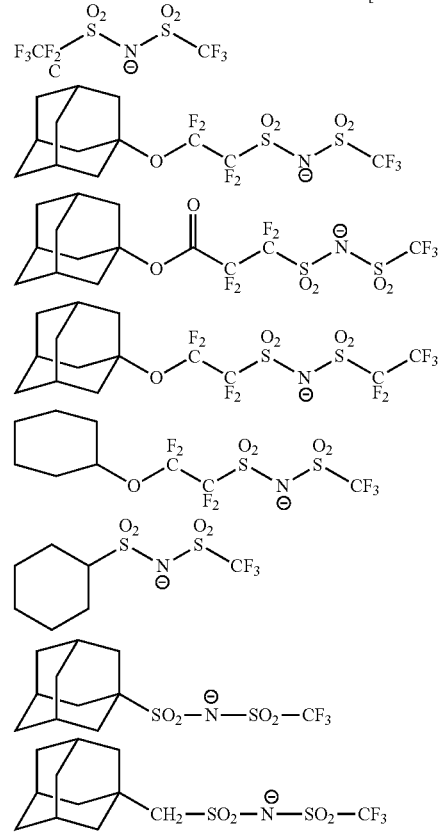

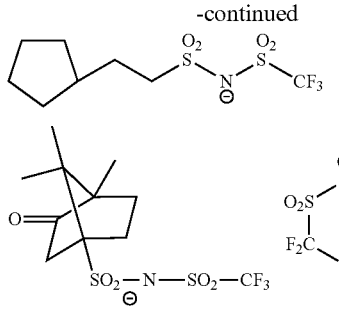

Anion Moiety of Component (b-3)

In formula (b-3), $R^{106}$ to $R^{108}$ each independently represents a cyclic group which may have a substituent, a chain-like alkyl group which may have a substituent or a chain-like alkenyl group which may have a substituent, and is the same as defined for $R^{101}$ in formula (b-1).

$L^{103}$ to $L^{105}$ each independently represents a single bond, —CO— or —SO$_2$—.

Specific examples of the anion represented by general formula (b-3) are shown below. However, the present invention is not limited to these examples.

[Chemical Formula 49]

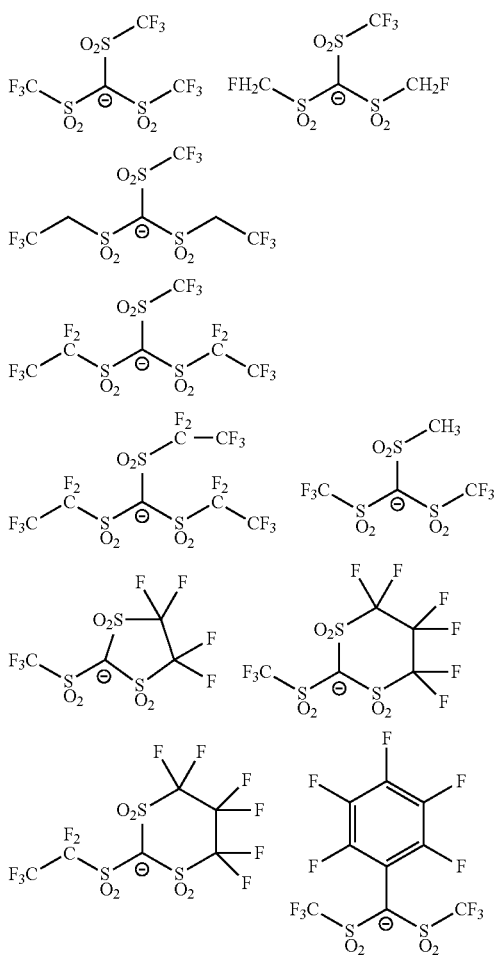

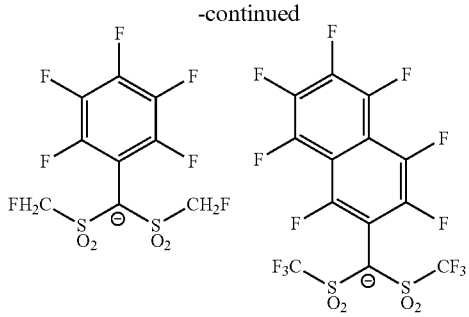

{Cation Moiety}

In formulae (b-1), (b-2) and (b-3), $M'^{m+}$ represents an organic cation having a valency of m other than the cation moiety of the compound represented by the aforementioned formula (b1-1), preferably a sulfonium cation or an iodonium cation, and most preferably a cation represented by any one of formulae (ca-1) to (ca-4) shown below.

[Chemical Formula 50]

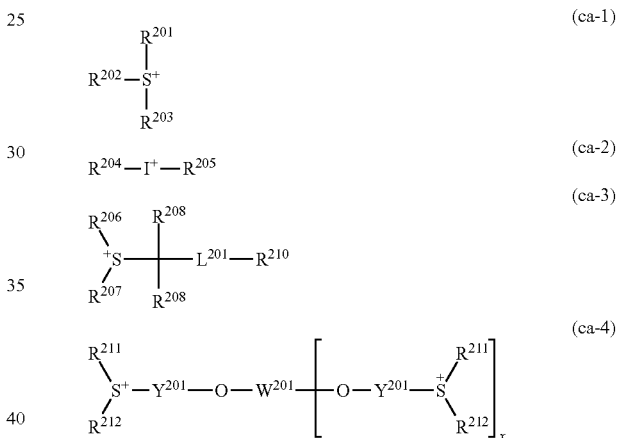

In the formulae, $R^{201}$ to $R^{207}$, $R^{211}$ and $R^{212}$ independently represents an aryl group, an alkyl group or an alkenyl group, provided that two of $R^{201}$ to $R^{203}$, $R^{206}$ and $R^{207}$, or $R^{211}$ and $R^{212}$ may be mutually bonded to form a ring with the sulfur atom; $R^{208}$ and $R^{209}$ each independently represents a hydrogen atom or an alkyl group of 1 to 5 carbon atoms; $R^{210}$ represents an aryl group which may have a substituent, an alkyl group which may have a substituent, an alkenyl group which may have a substituent or an —SO$_2$— containing cyclic group which may have a substituent; $L^{201}$ represents —C(=O)— or —C(=O)—O—; $Y^{201}$ each independently represents an arylene group, an alkylene group or an alkenylene group; x represents 1 or 2; and $W^{201}$ represents a linking group having a valency of (x+1).

As the aryl group for $R^{201}$ to $R^{207}$, $R^{211}$ and $R^{212}$, an unsubstituted aryl group of 6 to 20 carbon atoms can be mentioned, and a phenyl group or a naphthyl group is preferable.

The alkyl group for $R^{201}$ to $R^{207}$, $R^{211}$ and $R^{212}$ is preferably a chain-like or cyclic alkyl group having 1 to 30 carbon atoms.

The alkenyl group for $R^{201}$ to $R^{207}$, $R^{211}$ and $R^{212}$ preferably has 2 to 10 carbon atoms.

Specific examples of the substituent which $R^{201}$ to $R^{207}$ and $R^{210}$ to $R^{212}$ may have include an alkyl group, a halogen atom, a halogenated alkyl group, a carbonyl group, a cyano group, an amino group, an aryl group, an arylthio group and groups represented by formulae (ca-r-1) to (ca-r-7) shown below.

The aryl group within the arylthio group as the substituent is the same as defined for $R^{101}$, and specific examples include a phenylthio group and a biphenylthio group.

[Chemical Formula 51]

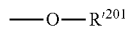
[ca-r-1]

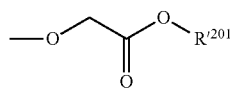
[ca-r-2]

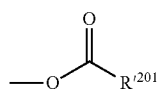
[ca-r-3]

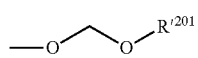
[ca-r-4]

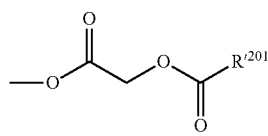
[ca-r-5]

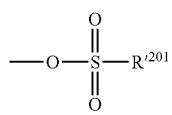
[ca-r-6]

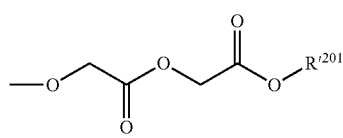
[ca-r-7]

In the formulae, $R'^{201}$ each independently represents a hydrogen atom, a cyclic group which may have a substituent, a chain-like alkyl group which may have a substituent or a chain-like alkenyl group which may have a substituent.

As the cyclic group which may have a substituent, the chain-like alkyl group which may have a substituent and the chain-like alkenyl group which may have a substituent for $R'^{201}$, the same groups as those described above for $R^{101}$ can be mentioned. As the cyclic group which may have a substituent and chain-like alkyl group which may have a substituent, the same groups as those described above for the acid dissociable group represented by the aforementioned formula (a1-r-2) can be also mentioned.

When $R^{201}$ to $R^{203}$, $R^{206}$, $R^{207}$, $R^{211}$ and $R^{212}$ are mutually bonded to form a ring with the sulfur atom, these groups may be mutually bonded via a hetero atom such as a sulfur atom, an oxygen atom or a nitrogen atom, or a functional group such as a carbonyl group, —SO—, —SO$_2$—, —SO$_3$—, —COO—, —CONH— or —N($R_N$)— (wherein $R_N$ represents an alkyl group of 1 to 5 carbon atoms). The ring containing the sulfur atom in the skeleton thereof is preferably a 3 to 10-membered ring, and most preferably a 5 to 7-membered ring. Specific examples of the ring formed include a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring, and a tetrahydrothiopyranium ring.

$R^{208}$ and $R^{209}$ each independently represents a hydrogen atom or an alkyl group of 1 to 5 carbon atoms, and preferably a hydrogen atom or an alkyl group of 1 to 3 carbon atoms, provided that, in the case of an alkyl group, the groups may be mutually bond to form a ring.

$R^{210}$ represents an aryl group which may have a substituent, an alkyl group which may have a substituent, an alkenyl group which may have a substituent, or an —SO$_2$— containing cyclic group which may have a substituent.

Examples of the aryl group for $R^{210}$ include an unsubstituted aryl group of 6 to 20 carbon atoms, and a phenyl group or a naphthyl group is preferable.

As the alkyl group for $R^{210}$, a chain-like or cyclic alkyl group having 1 to 30 carbon atoms is preferable.

The alkenyl group for $R^{210}$ preferably has 2 to 10 carbon atoms.

As the —SO$_2$— containing cyclic group for $R^{210}$ which may have a substituent, the same "—SO$_2$—containing cyclic groups" as those described above for $Ra^{21}$ in the aforementioned general formula (a2-1) can be mentioned, and the group represented by the aforementioned general formula (a5-r-1) is preferable.

Each $Y^{201}$ independently represents an arylene group, an alkylene group or an alkenylene group.

Examples of the arylene group for $Y^{201}$ include groups in which one hydrogen atom has been removed from an aryl group given as an example of the aromatic hydrocarbon group for $R^{101}$ in the aforementioned formula (b-1).

The alkylene group and the alkenylene group for $Y^{201}$ is the same as defined for the aliphatic hydrocarbon group as the divalent linking group represented by $Va^1$ in the aforementioned general formula (a1-1).

In the formula (ca-4), x represents 1 or 2.

$W^{201}$ represents a linking group having a valency of (x+1), i.e., a divalent or trivalent linking group.

As the divalent linking group for $W^{201}$, a divalent hydrocarbon group which may have a substituent is preferable, and as examples thereof, the same hydrocarbon groups as those described above for $Ya^{21}$ in the general formula (a2-1) can be mentioned. The divalent linking group for $W^{201}$ may be linear, branched or cyclic, and cyclic is more preferable. Among these, an arylene group having two carbonyl groups, each bonded to the terminal thereof is preferable. Examples of the arylene group include a phenylene group and a naphthylene group, and a phenylene group is particularly desirable.

As the trivalent linking group for $W^{201}$, a group in which one hydrogen atom has been removed from the aforementioned divalent linking group for $W^{201}$ and a group in which the divalent linking group has been bonded to another divalent linking group can be mentioned. The trivalent linking group for $W^{201}$ is preferably a group in which 2 carbonyl groups are bonded to an arylene group.

Specific examples of preferable cations represented by formula (ca-1) include cations represented by formulae (ca-1-1) to (ca-1-63) shown below.

[Chemical Formula 52]
(ca-1-1)
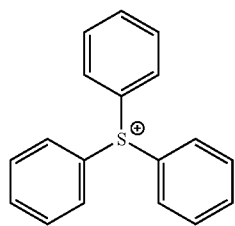
(ca-1-2)
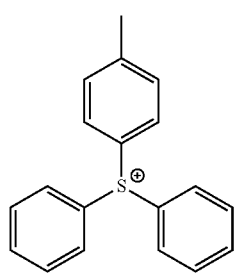
(ca-1-3)
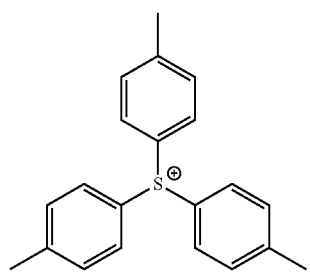
(ca-1-4)
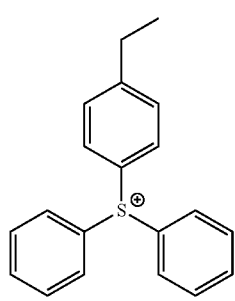
(ca-1-5)
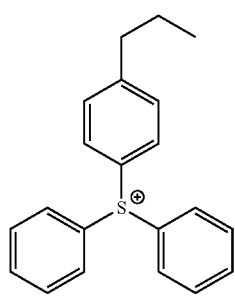
(ca-1-6)
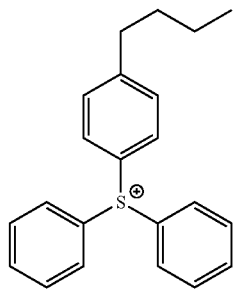
(ca-1-7)
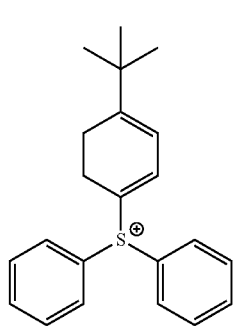
(ca-1-8)
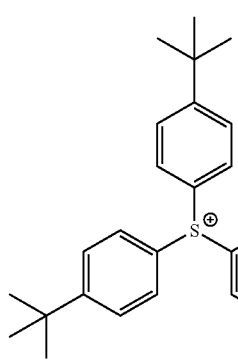
(ca-1-9)
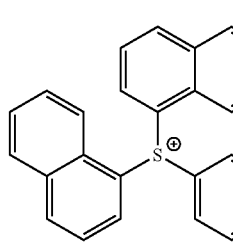
(ca-1-10)
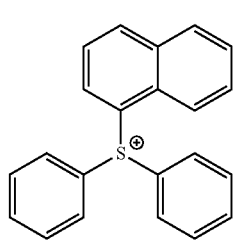

(ca-1-11) 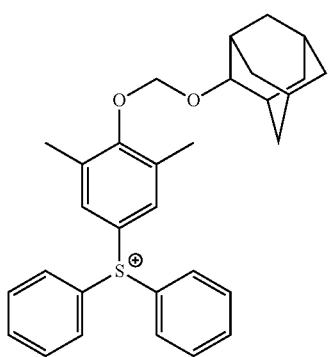
(ca-1-15) 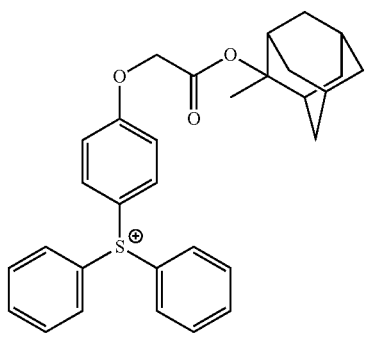
(ca-1-12) 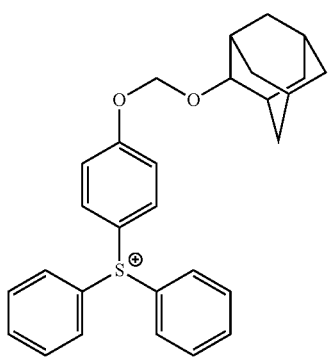
(ca-1-16) 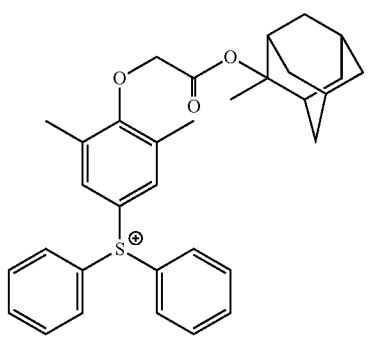
(ca-1-13) 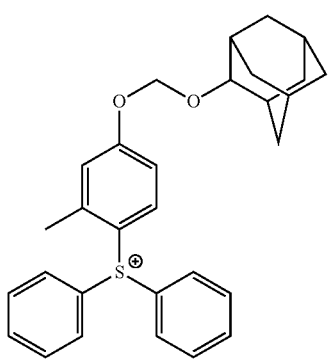
[Chemical Formula 53]
(ca-1-17) 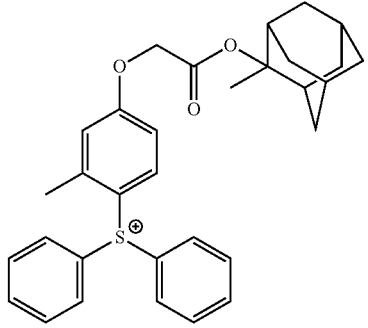
(ca-1-14) 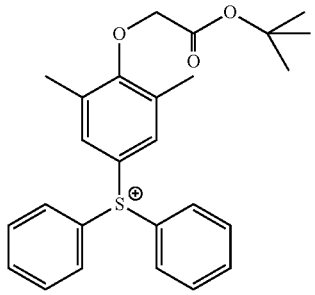
(ca-1-18) 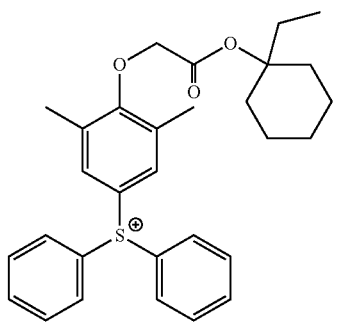

(ca-1-19)
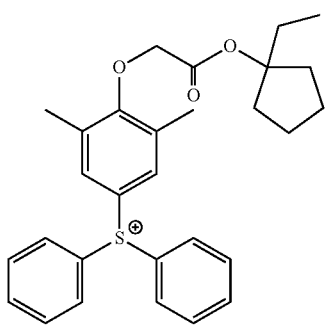
(ca-1-20)
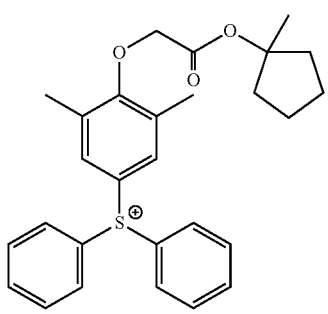
(ca-1-21)
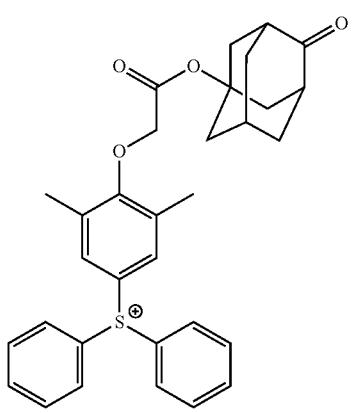
(ca-1-22)
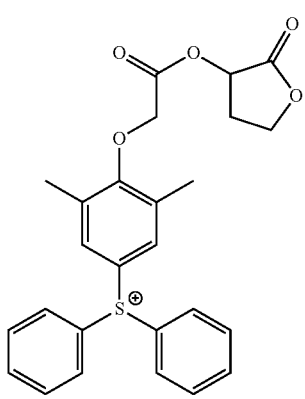
(ca-1-23)
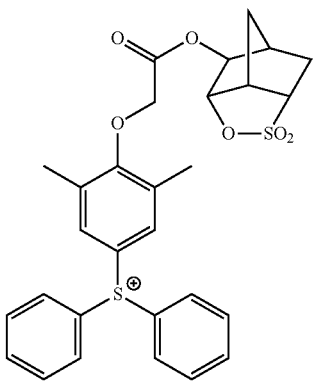
(ca-1-24)
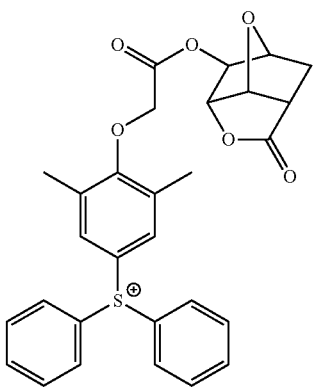
(ca-1-25)
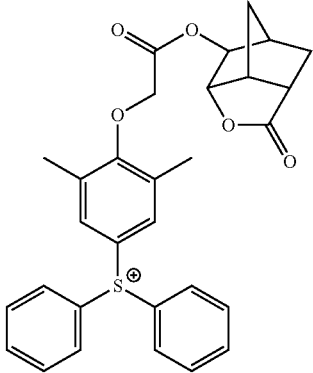
(ca-1-26)
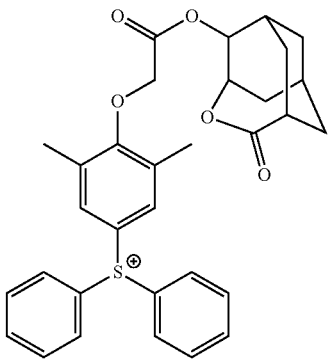

(ca-1-27)
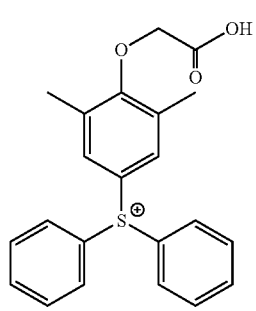
(ca-1-28)
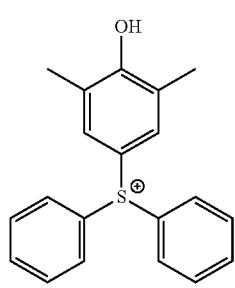
(ca-1-29)
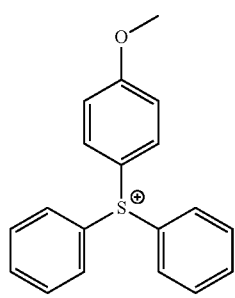
(ca-1-30)
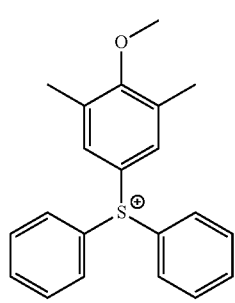
(ca-1-31)
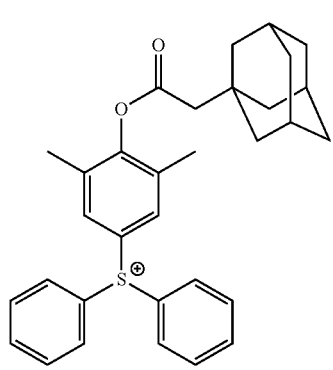
(ca-1-32)
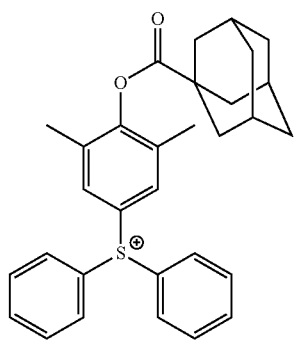
(ca-1-33)
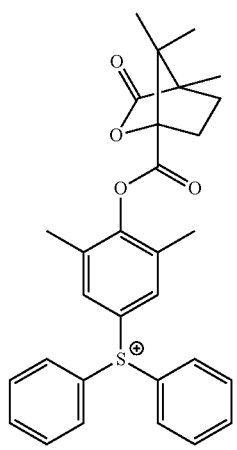
[Chemical Formula 54]
(ca-1-34)
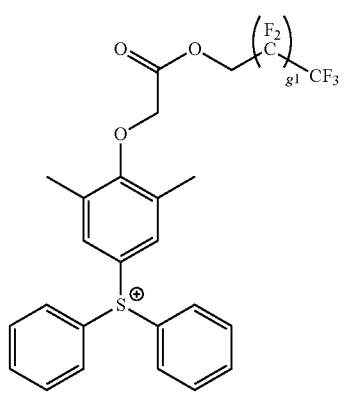
(ca-1-35)
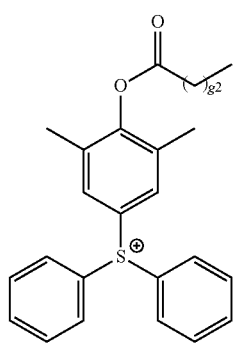

(ca-1-36)
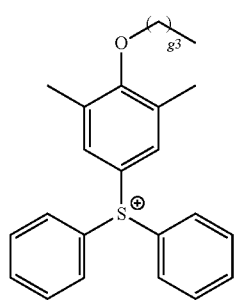
(ca-1-37)
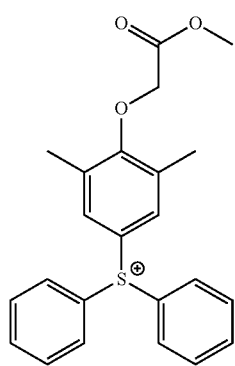
(ca-1-38)
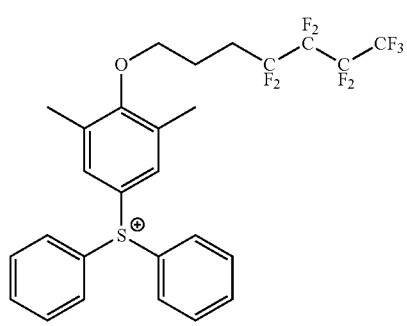
(ca-1-39)
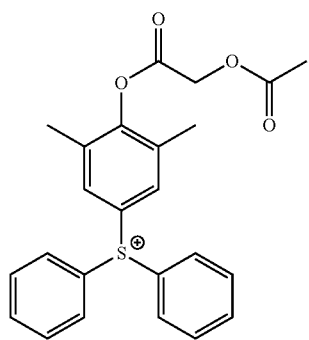
(ca-1-40)
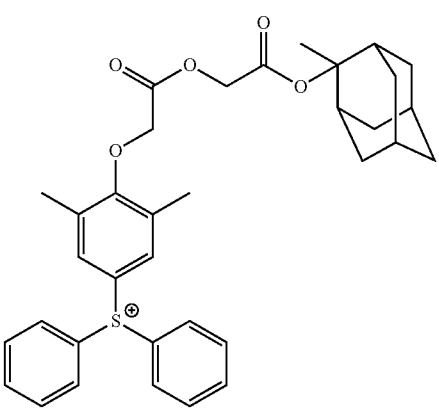
(ca-1-41)
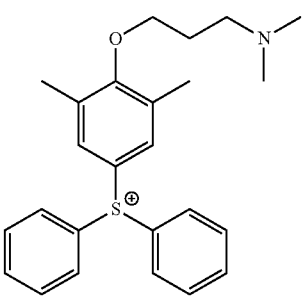
(ca-1-42)
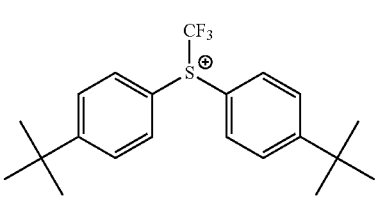
(ca-1-43)
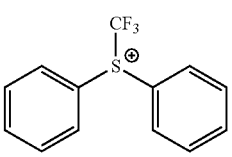
(ca-1-44)
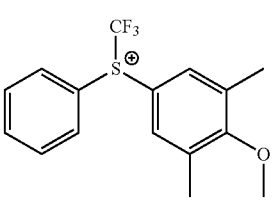
(ca-1-45)
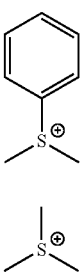
(ca-1-46)

(ca-1-47)
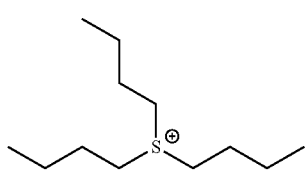
(ca-1-48)
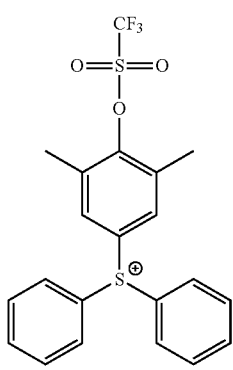
In the formulae, g1, g2 and g3 represent recurring numbers, wherein g1 is an integer of 1 to 5, g2 is an integer of 0 to 20, and g3 is an integer of 0 to 20.
[Chemical Formula 55]
(ca-1-49)
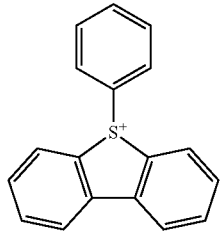
(ca-1-50)
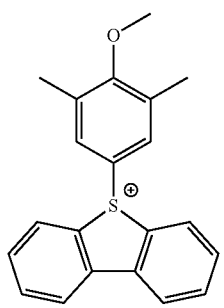
(ca-1-51)
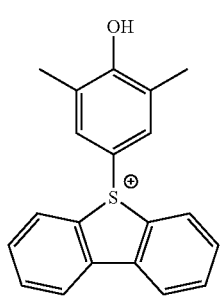
(ca-1-52)
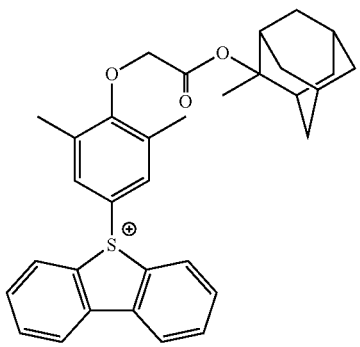
(ca-1-53)
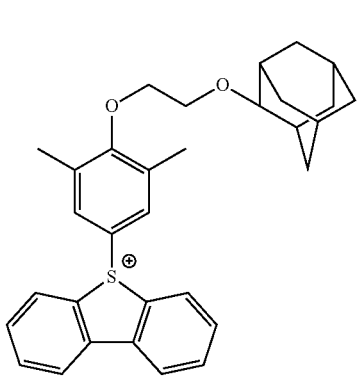
(ca-1-54)
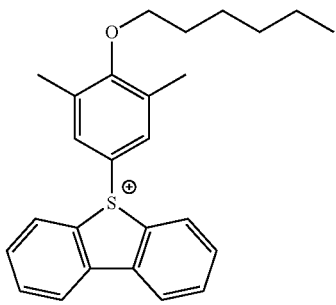
(ca-1-55)
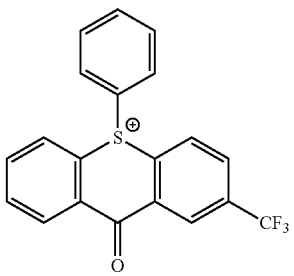
(ca-1-56)
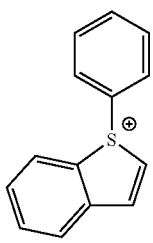

(ca-1-57) 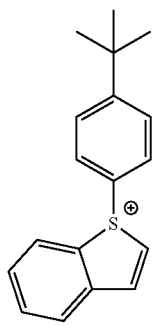

(ca-1-58) 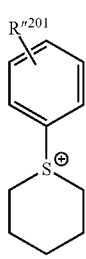

(ca-1-59) 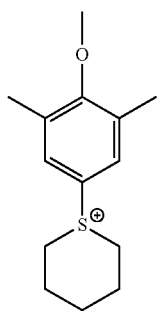

(ca-1-60) 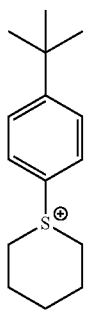

(ca-1-61) 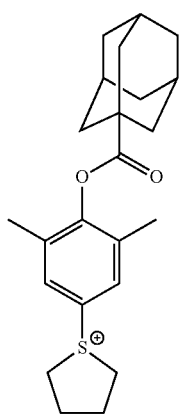

(ca-1-62) 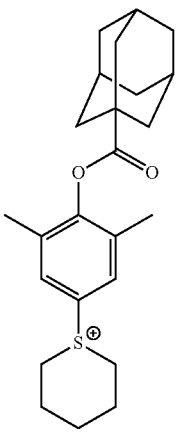

(ca-1-63) 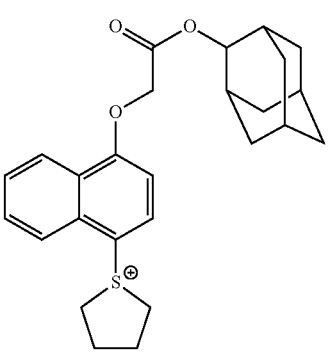

In the formulae, $R''^{201}$ represents a hydrogen atom or a substituent, and as the substituent, the same groups as those described above for substituting $R^{201}$ to $R^{207}$ and $R^{210}$ to $R^{212}$ can be mentioned.

Specific examples of preferable cations represented by formula (ca-3) include cations represented by formulae (ca-3-1) to (ca-3-6) shown below.

[Chemical Formula 56]

(ca-3-1) 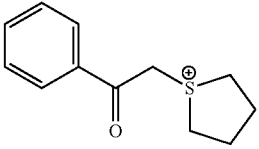

(ca-3-2) 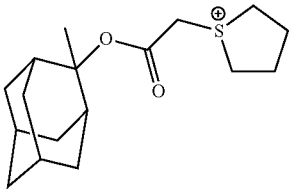

(ca-3-3) 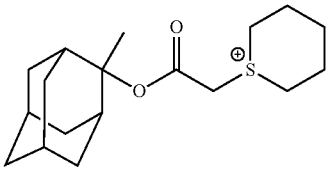

-continued (ca-3-4)
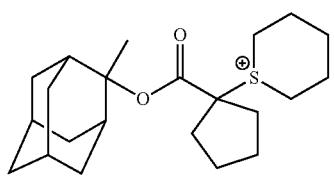

(ca-3-5)
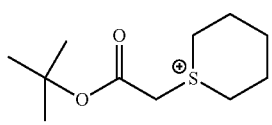

(ca-3-6)
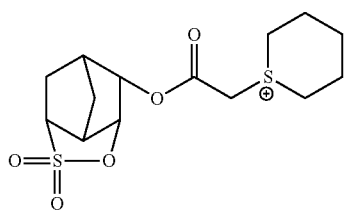

Specific examples of preferable cations represented by formula (ca-4) include cations represented by formulae (ca-4-1) and (ca-4-2) shown below.

[Chemical Formula 57]

(ca-4-1)
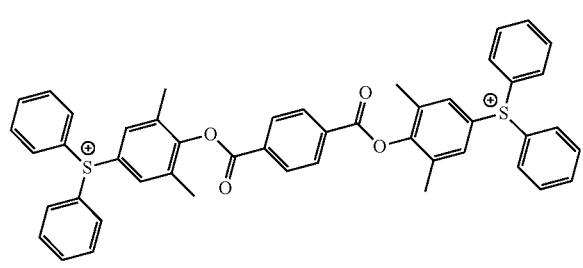

(ca-4-2)
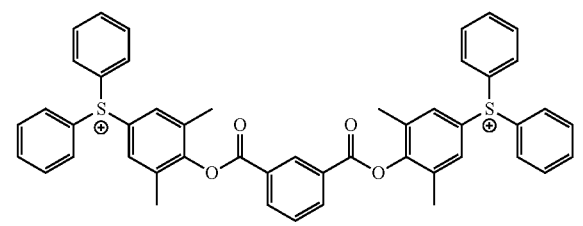

As the component (B), one type of these acid generators may be used alone, or two or more types may be used in combination.

When the resist composition of the present invention contains the component (B), the amount of the component (B) relative to 100 parts by weight of the component (A) is preferably within a range from 0.5 to 60 parts by weight, more preferably from 1 to 50 parts by weight, and still more preferably from 1 to 40 parts by weight. When the amount of the component (B) is within the above-mentioned range, formation of a resist pattern can be satisfactorily performed. Further, by virtue of the above-mentioned range, when each of the components are dissolved in an organic solvent, a uniform solution can be obtained and the storage stability becomes satisfactory.

<Optional Components>
[Basic Compound Component; Component (D)]

The resist composition of the present invention may include, in addition to the component (A), a basic compound component (hereafter, sometimes referred to as "component (D)").

The component (D) functions as an acid diffusion control agent, i.e., a quencher which traps the acid generated from the component (B) and the like upon exposure. In the present invention, a "basic compound" refers to a compound which is basic relative to the component (B).

In the present invention, the component (D) may be a basic compound (D1) (hereafter, referred to as "component (D1)") which has a cation moiety and an anion moiety, or a basic compound (D2) (hereafter, referred to as "component (D2)") which does not fall under the definition of component (D1).

(Component (D1))

In the case where the resist composition contains the component (B) in addition to the component (A), when a resist pattern is formed using a resist composition containing the component (D1), the contrast between exposed portions and unexposed portions is improved.

The component (D1) is not particularly limited, as long as it is basic in relation to the component (B). As the component (D1), at least one compound selected from the group consisting of a compound represented by general formula (d1-1) shown below (hereafter, referred to as "component (d1-1)"), a compound represented by general formula (d1-2) shown below (hereafter, referred to as "component (d1-2)") and a compound represented by general formula (d1-3) shown below (hereafter, referred to as "component (d1-3)") is preferably used.

At exposed portions, the components (d1-1) to (d1-3) do not function as a quencher, whereas at unexposed portions, the components (d1-1) to (d1-3) function as a quencher.

[Chemical Formula 58]

(d1-1)

(d1-2)

(d1-3)
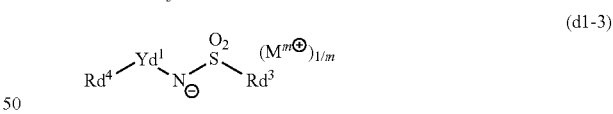

In the formulae, $Rd^1$ to $Rd^4$ each independently represents a hydrocarbon group which may have a substituent, provided that, the carbon atom adjacent to the sulfur atom within the $Rd^2$ in the formula (d1-2) has no fluorine atom bonded thereto; $Yd^1$ represents a single bond, an alkylene group or an arylene group; and $M^{m+}$ each independently represents a cation having a valency of m.

{Component (d1-1)}
Anion Moiety
In formula (d1-1), $Rd^1$ represents a hydrocarbon group which may have a substituent.

As an example of the hydrocarbon group for $Rd^1$ which may have a substituent, a monovalent group in which a hydrogen atom is bonded to one of the valence bonds of the hydrocarbon group for $Ya^{21}$ which may have a substituent in the aforementioned formula (a2-1). Among these examples, as Rd¹, an aromatic hydrocarbon group which may have a substituent or an aliphatic cyclic group which may have a substituent is preferable, and a phenyl group or a naphthyl group which may have a substituent, or a group in which one or more hydrogen atoms have been removed from a polycycloalkane such as adamantane, norbornane, isobornane, tricyclodecane or tetracyclododecane is more preferable. As the substituent, a hydroxy group is preferable.

As the hydrocarbon group for Rd¹ which may have a substituent, a linear, branched or alicyclic alkyl group or a fluorinated alkyl group is also preferable.

The linear, branched or alicyclic alkyl group for Rd¹ preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl or a decyl group, a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group, and an alicyclic alkyl group such as a norbornyl group or an adamantyl group.

The fluorinated alkyl group for Rd¹ may be either chain-like or cyclic, but is preferably linear or branched.

The fluorinated alkyl group preferably has 1 to 11 carbon atoms, more preferably 1 to 8, and still more preferably 1 to 4. Specific examples include a group in which part or all of the hydrogen atoms constituting a linear alkyl group (such as a methyl group, an ethyl group, a propyl group, a butyl group, a pentyl group, a hexyl group, a heptyl group, an octyl group, a nonyl group or a decyl group) have been substituted with fluorine atom(s), and a group in which part or all of the hydrogen atoms constituting a branched alkyl group (such as a 1-methylethyl group, a 1-methylpropyl group, a 2-methylpropyl group, a 1-methylbutyl group, a 2-methylbutyl group or a 3-methylbutyl group) have been substituted with fluorine atom(s).

The fluorinated alkyl group for Rd¹ may contain an atom other than fluorine. Examples of the atom other than fluorine include an oxygen atom, a carbon atom, a hydrogen atom, a sulfur atom and a nitrogen atom.

Among these, as the fluorinated alkyl group for Rd¹, a group in which part or all of the hydrogen atoms constituting a linear alkyl group have been substituted with fluorine atom(s) is preferable, and a group in which all of the hydrogen atoms constituting a linear alkyl group have been substituted with fluorine atoms (i.e., a perfluoroalkyl group) is more preferable.

Specific examples of preferable anion moieties for the component (d1-1) are shown below.

[Chemical Formula 59]

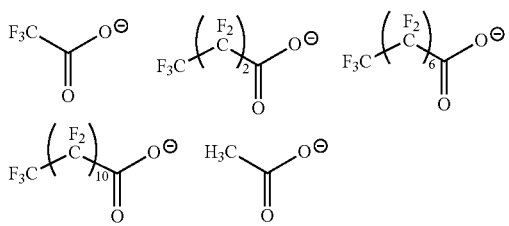

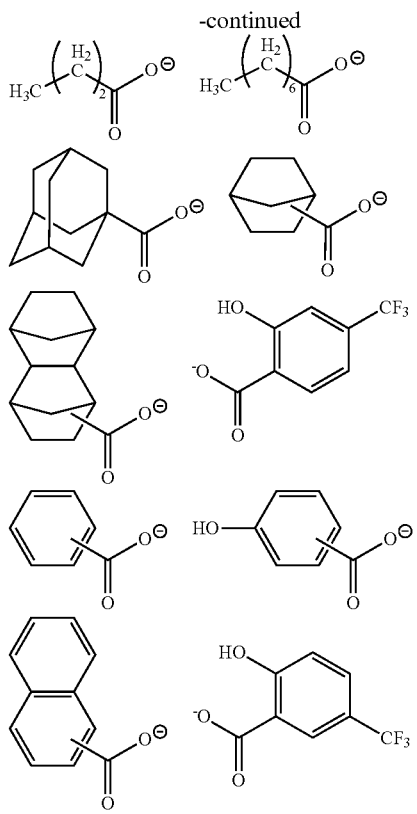

Cation Moiety

In formula (d1-1), $M^{m+}$ represents an organic cation having a valency of m.

The organic cation for $M^{m+}$ is not particularly limited, and examples thereof include the same cation moieties as those represented by the aforementioned formulas (ca-1) to (ca-4), and cation moieties represented by the aforementioned formulas (ca-1-1) to (ca-1-63) are preferable.

As the component (d1-1), one type of compound may be used, or two or more types of compounds may be used in combination.

{Component (d1-2)}

Anion Moiety

In formula (d1-2), Rd² represents a hydrocarbon group which may have a substituent.

The hydrocarbon group for Rd² is the same as defined for the hydrocarbon group represented by Rd¹ (which may have a substituent) in the formula (d1-1). However, the carbon atom adjacent to the sulfur atom within Rd² group has no fluorine atom bonded thereto (i.e., the carbon atom adjacent to the sulfur atom within Rd² group is not substituted with fluorine). As a result, the anion of the component (d1-2) becomes an appropriately weak acid anion, thereby improving the quenching ability of the component (D).

As Rd², an aliphatic cyclic group which may have a substituent is preferable, and a group in which one or more hydrogen atoms have been removed from adamantane, norbornane, isobornane, tricyclodecane, tetracyclododecane or camphor (which may have a substituent) is more preferable.

The hydrocarbon group for Rd² may have a substituent. As the substituent, the same groups as those described above for substituting the hydrocarbon group (e.g., aromatic hydrocarbon group, aliphatic hydrocarbon group) for Rd¹ in the formula (d1-1) can be mentioned.

Specific examples of preferable anion moieties for the component (d1-2) are shown below.

[Chemical Formula 60]

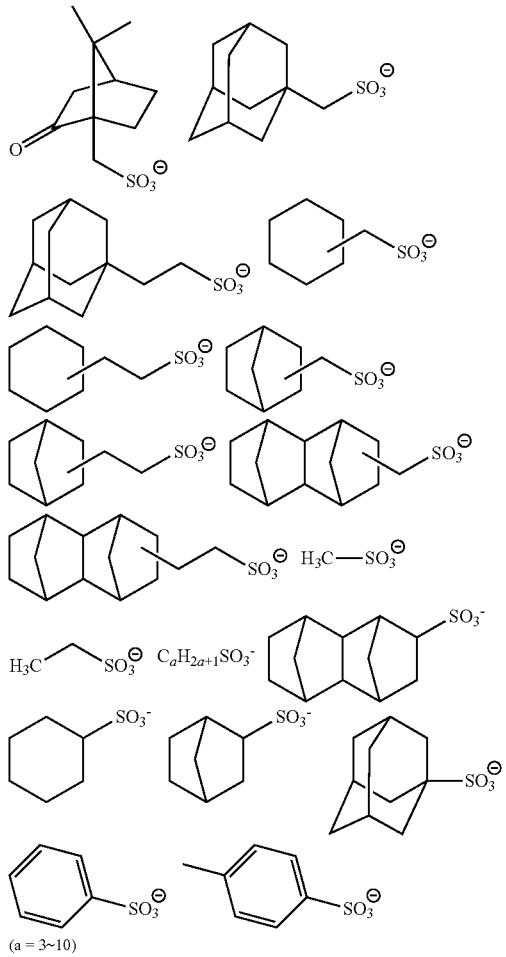

(a = 3~10)

Cation Moiety

In formula (d1-2), $M^{m+}$ is an organic cation having a valency of m, and is the same as defined for $M^{m+}$ in the aforementioned formula (d1-1).

As the component (d1-2), one type of compound may be used, or two or more types of compounds may be used in combination.

{Component (d1-3)}
Anion Moiety

In formula (d1-3), $Rd^3$ represents a hydrocarbon group which may have a substituent. The hydrocarbon group for $Rd^3$ which may have a substituent is the same as defined for the hydrocarbon group represented by $Rd^1$ (which may have a substituent) in the aforementioned formula (d1-1), and is preferably a hydrocarbon group containing a fluorine atom.

The hydrocarbon group for $Rd^3$ containing a fluorine atom is preferably a fluorinated alkyl group, and more preferably the same fluorinated alkyl group as defined for $Rd^1$.

In formula (d1-3), $Rd^4$ represents a hydrocarbon group which may have a substituent. The hydrocarbon group for $Rd^4$ which may have a substituent is the same as defined for the hydrocarbon group represented by $Rd^1$ (which may have a substituent) in the aforementioned formula (d1-1), and preferably an alkyl group, an alkoxy group, —O—C(=O)—C($Rd^{42}$)=CH$_2$ (wherein $Rd^{42}$ represents a hydrogen atom, an alkyl group of 1 to 5 carbon atoms or a halogenated alkyl group of 1 to 5 carbon atoms), —C(=O)—$Rd^{43}$ or —O—C(=O)—$Rd^{43}$ (wherein $Rd^{43}$ represents a hydrocarbon group).

The alkyl group for $Rd^4$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $Rd^4$ may be substituted with a hydroxy group, a cyano group or the like.

The alkoxy group for $Rd^4$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are preferable.

When $Rd^4$ is —O—C(=O)—C($Rd^{42}$)=CH$_2$, $Rd^{42}$ represents a hydrogen atom, an alkyl group of 1 to 5 carbon atoms or a halogenated alkyl group of 1 to 5 carbon atoms.

As the alkyl group of 1 to 5 carbon atoms for $Rd^{42}$, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group.

The halogenated alkyl group for $Rd^{42}$ is a group in which part or all of the hydrogen atoms of the aforementioned alkyl group of 1 to 5 carbon atoms has been substituted with halogen atoms. Examples of the halogen atom include a fluorine atom, a chlorine atom, a bromine atom and an iodine atom, and a fluorine atom is particularly desirable.

As $Rd^{42}$, a hydrogen atom, an alkyl group of 1 to 3 carbon atoms or a fluorinated alkyl group of 1 to 3 carbon atoms is preferable, and a hydrogen atom or a methyl group is particularly desirable in terms of industrial availability.

When $Rd^4$ is —C(=O)—$Rd^{43}$ or —O—C(=O)—$Rd^{43}$, $Rd^{43}$ represents a hydrocarbon group.

The hydrocarbon group for $Rd^{43}$ may be either an aromatic hydrocarbon group or an aliphatic hydrocarbon group. Specific examples of the hydrocarbon group for $Rd^{43}$ include the same hydrocarbon groups (which may have a substituent) as those defined for $Rd^1$ in the aforementioned formula (d1-1).

As the hydrocarbon group for $Rd^{43}$, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $Rd^{43}$ is an alicyclic group, the resist composition can be satisfactorily dissolved in an organic solvent, thereby improving the lithography properties. Alternatively, when $Rd^{43}$ is an aromatic group, the resist composition exhibits an excellent photoabsorption efficiency in a lithography process using EUV or the like as the exposure source, thereby resulting in the improvement of the sensitivity and the lithography properties.

Among these, as $Rd^{42}$, —O—C(=O)—C($Rd^{42'}$)=CH$_2$ ($Rd^{42'}$ represents a hydrogen atom or a methyl group) or —O—C(=O)—$Rd^{43'}$ ($Rd^{43'}$ represents an aliphatic cyclic group) is preferable.

In formula (d1-3), $Yd^1$ represents a single bond, an alkylene group or an arylene group.

The alkylene group or the arylene group for $Yd^1$ is the same as defined for the divalent linking group (aliphatic hydrocarbon group and aromatic hydrocarbon group) represented by Ya$^{21}$ (which may have a substituent) in the aforementioned formula (a2-1).

As Yd$^1$, an alkylene group is preferable, a linear or branched alkylene group is more preferable, and a methylene group or an ethylene group is still more preferable.

Specific examples of preferable anion moieties for the component (d1-3) are shown below.

[Chemical Formula 61]

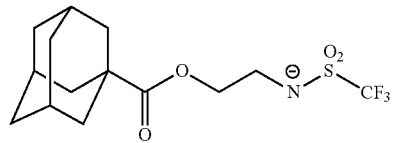
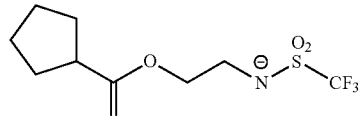
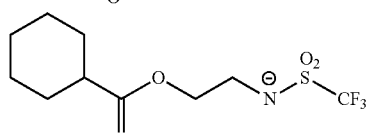
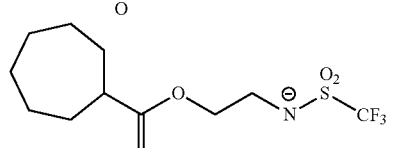
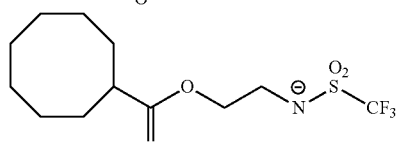
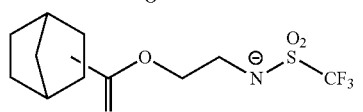
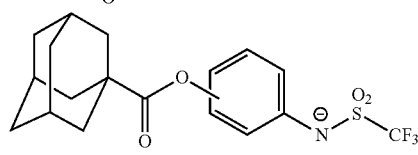

-continued

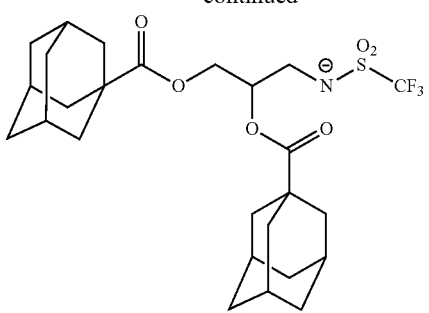

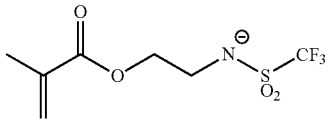
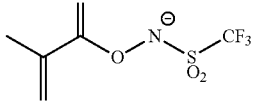
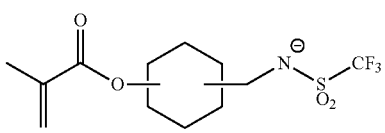

[Chemical Formula 62]

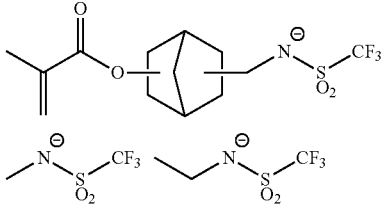

-continued

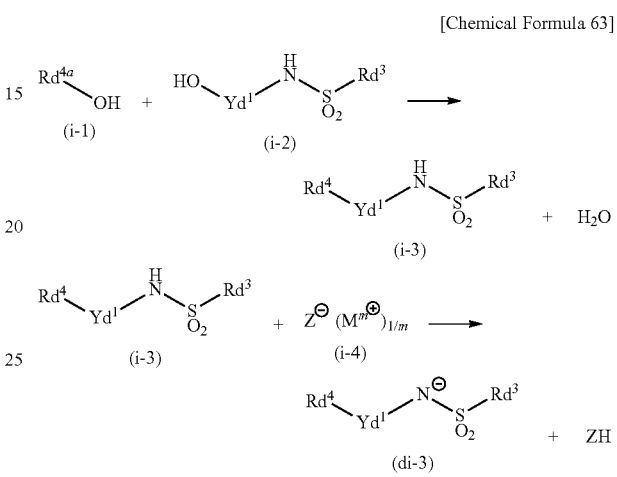

Cation Moiety

In formula (d1-3), $M^{m+}$ is an organic cation having a valency of m, and is the same as defined for $M^{m+}$ in the aforementioned formula (d1-1).

As the component (d1-3), one type of compound may be used, or two or more types of compounds may be used in combination.

As the component (D1), one type of the aforementioned components (d1-1) to (d1-3), or at least two types of the aforementioned components (d1-1) to (d1-3) can be used in combination.

The amount of the component (D1) relative to 100 parts by weight of the component (A) is preferably within a range from 0.5 to 10 parts by weight, more preferably from 0.5 to 8 parts by weight, and still more preferably from 1 to 8 parts by weight.

When the amount of the component (D1) is at least as large as the lower limit of the above-mentioned range, excellent lithography properties and excellent resist pattern shape can be obtained. On the other hand, when the amount of the component (D1) is no more than the upper limit of the above-mentioned range, sensitivity can be maintained at a satisfactory level, and through-put becomes excellent.

{Production Method of Component (D1)}

The production methods of the components (d1-1) and (d1-2) are not particularly limited, and the components (d1-1) and (d1-2) can be produced by conventional methods.

The production method of the component (d1-3) is not particularly limited. For example, in the case where $Rd^4$ in formula (d1-3) is a group having an oxygen atom on the terminal thereof which is bonded to $Yd^1$, the compound (d1-3) represented by general formula (d1-3) can be produced by reacting a compound (i-1) represented by general formula (i-1) shown below with a compound (i-2) represented by general formula (i-2) shown below to obtain a compound (i-3) represented by general formula (i-3), and reacting the compound (i-3) with a compound $Z^-(M^{m+})_{l/m}$(i-4) having the desired cation $M^{m+}$, thereby obtaining the compound (d1-3).

[Chemical Formula 63]

In the formulae, $Rd^4$, $Yd^1$, $Rd^3$ and $M^{m+}$ are respectively the same as defined for $Rd^4$, $Yd^1$, $Rd^3$ and $M^{m+}$ in the aforementioned general formula (d1-3); $Rd^{4a}$ represents a group in which the terminal oxygen atom has been removed from $Rd^4$; and $Z^-$ represents a counteranion.

Firstly, the compound (i-1) is reacted with the compound (i-2), to thereby obtain the compound (i-3).

In formula (i-1), $Rd^{4a}$ represents a group in which the terminal oxygen atom has been removed from $Rd^4$. In formula (i-2), $Yd^1$ and $Rd^3$ are the same as defined above.

As the compound (i-1) and the compound (i-2), commercially available compounds may be used, or the compounds may be synthesized.

The method for reacting the compound (i-1) with the compound (i-2) to obtain the compound (i-3) is not particularly limited, but can be performed, for example, by reacting the compound (i-1) with the compound (i-2) in an organic solvent in the presence of an appropriate acidic catalyst, followed by washing and recovering the reaction mixture.

The acidic catalyst used in the above reaction is not particularly limited, and examples thereof include toluenesulfonic acid and the like. The amount of the acidic catalyst is preferably 0.05 to 5 moles, per 1 mole of the compound (i-2).

As the organic solvent used in the above reaction, any organic solvent which is capable of dissolving the raw materials, i.e., the compound (i-1) and the compound (i-2) can be used, and specific examples thereof include toluene and the like. The amount of the organic solvent is preferably 0.5 to 100 parts by weight, more preferably 0.5 to 20 parts by weight, relative to the amount of the compound (i-1). As the solvent, one type may be used alone, or two or more types may be used in combination.

In general, the amount of the compound (i-2) used in the above reaction is preferably 0.5 to 5 moles per 1 mole of the compound (i-1), and more preferably 0.8 to 4 moles per 1 mole of the compound (i-1).

The reaction time depends on the reactivity of the compounds (i-1) and (i-2), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

Next, the obtained compound (i-3) is reacted with the compound (i-4), thereby obtaining the compound (d1-3).

In formula (i-4), $M^{m+}$ is the same as defined above, and $Z^-$ represents a counteranion. $Z^-$ is not particularly limited, and a conventional counteranion can be used.

The method for reacting the compound (i-3) with the compound (i-4) to obtain the compound (d1-3) is not particularly limited, but can be performed, for example, by dissolving the compound (i-3) in an organic solvent and water in the presence of an appropriate alkali metal hydroxide, followed by addition of the compound (i-4) and stirring.

The alkali metal hydroxide used in the above reaction is not particularly limited, and examples thereof include sodium hydroxide, potassium hydroxide and the like. The amount of the alkali metal hydroxide is preferably 0.3 to 3 moles, per 1 mole of the compound (i-3).

Examples of the organic solvent used in the above reaction include dichloromethane, chloroform, ethyl acetate and the like. The amount of the organic solvent is preferably 0.5 to 100 parts by weight, and more preferably 0.5 to 20 parts by weight, relative to the weight of the compound (i-3). As the solvent, one type may be used alone, or two or more types may be used in combination.

In general, the amount of the compound (i-4) used in the above reaction is preferably 0.5 to 5 moles per 1 mole of the compound (i-3), and more preferably 0.8 to 4 moles per 1 mole of the compound (i-3).

The reaction time depends on the reactivity of the compounds (i-3) and (i-4), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

After the reaction, the compound (d1-3) contained in the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

The structure of the compound (d1-3) obtained in the manner described above can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

The amount of the component (D1) relative to 100 parts by weight of the component (A) is preferably within a range from 0.5 to 10.0 parts by weight, more preferably from 0.5 to 8.0 parts by weight, and still more preferably from 1.0 to 8.0 parts by weight. When the amount of at least as large as the lower limit of the above-mentioned range, excellent lithography properties and excellent resist pattern shape can be obtained. On the other hand, when the amount of the component (D) is no more than the upper limit of the above-mentioned range, sensitivity can be maintained at a satisfactory level, and through-put becomes excellent.

(Component (D2))

The component (D) may contain a basic compound component (D2) (hereafter, referred to as component (D2)) which does not fall under the definition of component (D1).

The component (D2) is not particularly limited, as long as it is a compound which is basic relative to the component (B), so as to functions as an acid diffusion inhibitor, and does not fall under the definition of the component (D1). As the component (D2), any of the conventionally known compounds may be selected for use. Among these, an aliphatic amine, particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris {2-(2-methoxyethoxy)ethyl}amine, tris{2-(2-methoxyethoxymethoxy)ethyl}amine, tris {2-(1-methoxyethoxy)ethyl}amine, tris{2-(1-ethoxyethoxy)ethyl}amine, tris {2-(1-ethoxypropoxy)ethyl}amine, tris[2-{2-(2-hydroxyethoxy)ethoxy}ethyl]amine and triethanolamine triacetate, and triethanolamine triacetate is preferable.

Further, as the component (D2), an aromatic amine may be used.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonylpyrrolidine.

As the component (D2), one type of compound may be used alone, or two or more types may be used in combination.

The component (D2) is typically used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

As the component (D), one type of compound may be used, or two or more types of compounds may be used in combination.

When the resist composition of the present invention contains the component (D), the amount of the component (D) relative to 100 parts by weight of the component (A) is preferably within a range from 0.1 to 15 parts by weight, more preferably from 0.3 to 12 parts by weight, and still more preferably from 0.5 to 12 parts by weight. When the amount of the component (D) is at least as large as the lower limit of the above-mentioned range, various lithography properties (such as roughness) of the resist composition are improved. Further, a resist pattern having an excellent shape can be obtained. On the other hand, when the amount of the component (D) is no more than the upper limit of the above-mentioned range, sensitivity can be maintained at a satisfactory level, and through-put becomes excellent.

<Optional Components>

[Component (E)]

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters and phenylphosphinic acid.

As the component (E), one type may be used alone, or two or more types may be used in combination.

The component (E) is typically used in an amount within a range from 0.01 to 5.0 parts by weight, relative to 100 parts by weight of the component (A).

<Optional Components>

[Component (F)]

In the present invention, the resist composition may further include a fluorine additive (hereafter, referred to as "component (F)") for imparting water repellency to the resist film.

As the component (F), for example, a fluorine-containing polymeric compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be used.

Specific examples of the component (F) include polymers having a structural unit (f1) represented by general formula (f1-1) shown below. As the polymer, a polymer (homopolymer) consisting of a structural unit (f1) represented by formula (f1-1) shown below; a copolymer of a structural unit (f1) represented by formula (f1-1) shown below and the aforementioned structural unit (a1); and a copolymer of a structural unit (f1) represented by formula (f1-1) shown below, a structural unit derived from acrylic acid or methacrylic acid and the aforementioned structural unit (a1) are preferable. As the structural unit (a1) to be copolymerized with a structural unit (f1) represented by formula (f1-1) shown below, a structural unit derived from 1-ethyl-1-cyclooctyl(meth)acrylate or a structural unit represented by the aforementioned formula (a1-2-01) is preferable.

[Chemical Formula 64]

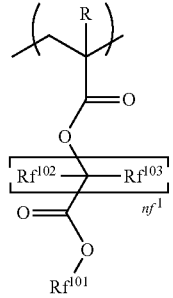

(f1-1)

In the formula, R is the same as defined above; $Rf^{102}$ and $R^{103}$ each independently represents a hydrogen atom, a halogen atom, an alkyl group of 1 to 5 carbon atoms, or a halogenated alkyl group of 1 to 5 carbon atoms, provided that $Rf^{102}$ and $Rf^{103}$ may be the same or different; $nf^1$ represents an integer of 1 to 5; and $Rf^{101}$ represents an organic group containing a fluorine atom.

In formula (f1-1), R bonded to the carbon atom on the α-position is the same as defined above. As R, a hydrogen atom or a methyl group is preferable.

In formula (f1-1), examples of the halogen atom for $Rf^{102}$ and $Rf^{103}$ include a fluorine atom, a chlorine atom, a bromine atom and an iodine atom, and a fluorine atom is particularly desirable. Examples of the alkyl group of 1 to 5 carbon atoms for $Rf^{102}$ and $Rf^{103}$ include the same alkyl group of 1 to 5 carbon atoms as those described above for R, and a methyl group or an ethyl group is preferable. Specific examples of the halogenated alkyl group of 1 to 5 carbon atoms represented by $Rf^{102}$ or $Rf^{103}$ include groups in which part or all of the hydrogen atoms of the aforementioned alkyl groups of 1 to 5 carbon atoms have been substituted with halogen atoms. Examples of the halogen atom include a fluorine atom, a chlorine atom, a bromine atom and an iodine atom, and a fluorine atom is particularly desirable. Among these, as $Rf^{102}$ and $Rf^{103}$, a hydrogen atom, a fluorine atom or an alkyl group of 1 to 5 carbon atoms is preferable, and a hydrogen atom, a fluorine atom, a methyl group or an ethyl group is more preferable.

In formula (f1-1), $nf^1$ represents an integer of 1 to 5, preferably an integer of 1 to 3, and more preferably 1 or 2.

In formula (f1-1), $Rf^{101}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and most preferably 1 to 10 carbon atoms.

It is preferable that the hydrocarbon group having a fluorine atom has 25% or more of the hydrogen atoms within the hydrocarbon group fluorinated, more preferably 50% or more, and most preferably 60% or more, as the hydrophobicity of the resist film during immersion exposure is enhanced.

Among these, as $Rf^{101}$, a fluorinated hydrocarbon group of 1 to 5 carbon atoms is preferable, and a trifluoromethyl group, $-CH_2-CF_3$, $-CH_2-CF_2-CF_3$, $-CH(CF_3)_2$, $-CH_2-CH_2-CF_3$, and $-CH_2-CH_2-CF_2-CF_2-CF_2-CF_3$ are most preferable.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (F) is preferably 1.0 to 5.0, more preferably 1.0 to 3.0, and most preferably 1.2 to 2.5.

As the component (F), one type may be used alone, or two or more types may be used in combination.

The component (F) is typically used in an amount within a range from 0.5 to 10 parts by weight, relative to 100 parts by weight of the component (A).

[Other Additives]

If desired, other miscible additives can also be added to the resist composition of the present invention. Examples of such miscible additives include additive resins for improving the performance of the resist film, dissolution inhibitors, plasticizers, stabilizers, colorants, halation prevention agents, and dyes.

[Component (S)]

The resist composition for immersion exposure according to the present invention can be prepared by dissolving the materials for the resist composition in an organic solvent (hereafter, frequently referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone; ketones such as acetone, methyl ethyl ketone (MEK), cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

These solvents can be used individually, or in combination as a mixed solvent.

Among these, PGMEA, PGME, γ-butyrolactone and EL are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL or cyclohexanone is mixed as the polar solvent, the PGMEA:EL or cyclohexanone weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate In general, the organic solvent is used in an amount such that the solid content of the resist composition becomes within the range from 1 to 20% by weight, and preferably from 2 to 15% by weight.

<<Method of Forming a Resist Pattern>>

The method of forming a resist pattern according to the present invention includes: forming a resist film on a substrate using a resist composition of the present invention; conducting exposure of the resist film; and developing the resist film to form a resist pattern.

The method for forming a resist pattern according to the present invention can be performed, for example, as follows:

Firstly, a resist composition of the present invention is applied to a substrate using a spinner or the like, and a bake treatment (post applied bake (PAB)) is conducted at a temperature of 80 to 150° C. for 40 to 120 seconds, preferably 60 to 90 seconds, to form a resist film.

Following selective exposure of the thus formed resist film, either by exposure through a mask having a predetermined pattern formed thereon (mask pattern) using an exposure apparatus such as an ArF exposure apparatus, an electron beam lithography apparatus or an EUV exposure apparatus, or by patterning via direct irradiation with an electron beam without using a mask pattern, baking treatment (post exposure baking (PEB)) is conducted under temperature conditions of 80 to 150° C. for 40 to 120 seconds, and preferably 60 to 90 seconds.

Next, the resist film is subjected to a developing treatment.

The developing treatment is conducted using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, bake treatment (post bake) can be conducted following the developing. In this manner, a resist pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention is effective to KrF excimer laser, ArF excimer laser, EB and EUV.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents can be used which are capable of dissolving the component (A) (prior to exposure). Specific examples of the organic solvent include polar solvents such as ketone solvents, ester solvents, alcohol solvents, amide solvents and ether solvents, and hydrocarbon solvents.

If desired, the organic developing solution may have a conventional additive blended. Examples of the additive include surfactants. The surfactant is not particularly limited, and for example, an ionic or non-ionic fluorine and/or silicon surfactant can be used.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in the case of a solvent developing process, any of the aforementioned organic solvents contained in the organic developing solution can be used which hardly dissolves the resist pattern. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, more preferably at least one solvent selected from the group consisting of alcohol solvents and ester solvents, and an alcohol solvent is particularly desirable.

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

By virtue of the resist composition of the present invention containing the component (B1), in the formation of a pattern on a resist film using the resist composition, excellent lithography properties such as LWR, EL margin and MEF can be obtained. The reason for this has not been elucidated yet, but is presumed as follows.

The naphthoquinonediazide structure contained in the component (B1) is decomposed upon exposure to generate a carboxylic acid, thereby changing the component (B1) from being hydrophobic to being hydrophilic. By changing to be hydrophilic, it is presumed that the difference between unexposed portions and exposed portions in terms of solubility in a developing solution (i.e., dissolution contrast) is enhanced, and lithography properties are improved.

Further, a naphthoquinonediazide structure has a wide absorption band. Therefore, it is considered that an acid generator having a naphthoquinonediazide structure can be used not only for conventional ArF (193 nm) and KrF (248 nm), but also for i-line (365 nm), h-line (405 nm) and g-line (436 nm).

EXAMPLES

The present invention will be described more specifically with reference to the following examples, although the scope of the present invention is by no way limited by these examples.

Synthesis Example of Compound 1

4.0 g of PAG-A, 3.2 g of 1,2-naphthoquinonediazide-4-sulfonylchloride and 29 g of dichloromethane were added and stirred at room temperature. 1.3 g of triethylamine (TEA) was gradually added thereto in a dropwise manner, followed by stirring at room temperature for 4 hours. Thereafter, the dichloromethane phase was washed with a diluted hydrochloric acid and 3 times with pure water, and the solvent was distilled off under reduced pressure, thereby obtaining 3.6 g of a compound 1.

The obtained compound 1 was analyzed by NMR, and the structure thereof was identified by the following results.

$^1$H-NMR (400 MHz, DMSO-d6): δ(ppm)=8.57 (1H, ArH), 8.34 (2H, ArH), 7.71-7.99 (14H, ArH), 2.21 (6H, CH$_3$).

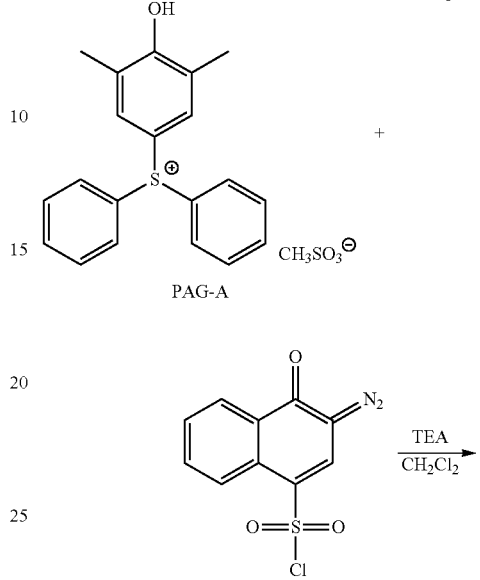

[Chemical Formula 65]

PAG-A

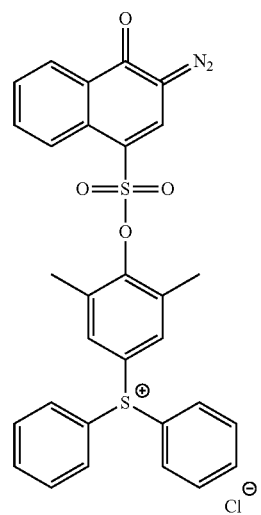

Compound 1

Compounds 2 to 4 were synthesized in the same manner as the compound 1. The obtained compound was analyzed by NMR, and the structure thereof was identified by the following results.

Compound 2: $^1$H-NMR (400 MHz, DMSO-d6): δ(ppm)= 8.57 (1H, ArF), 8.34 (2H, Ar H), 7.71-7.75 (4H, ArH), 3.73-3.91 (4H, SCH$_2$), 1.56-2.41, (12H, CH$_3$+CH$_2$CH$_2$CH$_2$).

Compound 3: $^1$H-NMR (400 MHz, DMSO-d6): δ(ppm) = 8.57, (1H, ArF), 8.42 (2H, ArH), 8.34 (2H, ArH), 8.17 (1H, ArH), 7.71-7.91 (4H, ArH), 7.23, (1H, ArH), 3.75-4.19 (4H, SCH2), 2.29-2.60 (4H, SCH$_2$CH$_2$).

Compound 4: $^1$H-NMR (400 MHz, DMSO-d6): δ(ppm)= 8.56, (1H, ArH), 8.46 (1H, ArH), 8.10 (1H, ArH), 7.86 (1H, ArH), 7.71-7.89 (11H, ArH), 7.59 (2H, ArH), 2.30 (6H, CH$_3$).

[Chemical Formula 66]
Compound 2
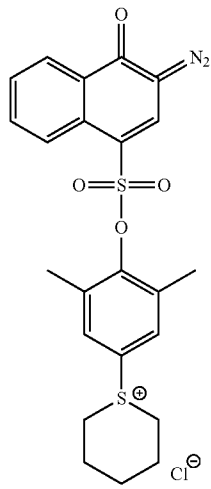
Compound 3
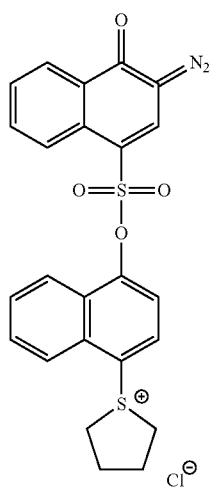
Compound 4
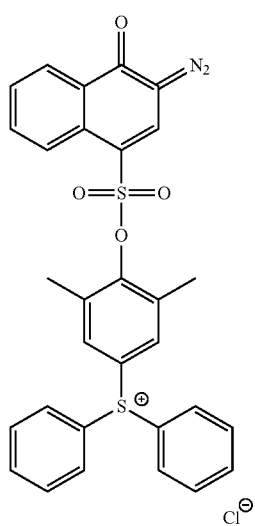
The compounds 1 to 4 were subjected to a salt exchange with a predetermined anion, thereby deriving compounds BQ-1 to BQ-7 shown below.
[Chemical Formula 67]
BQ-1
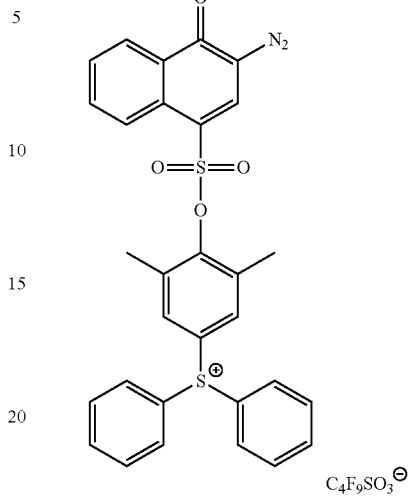
BQ-2
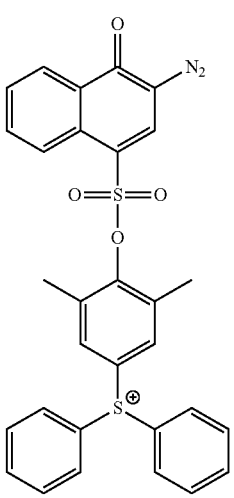
BQ-3
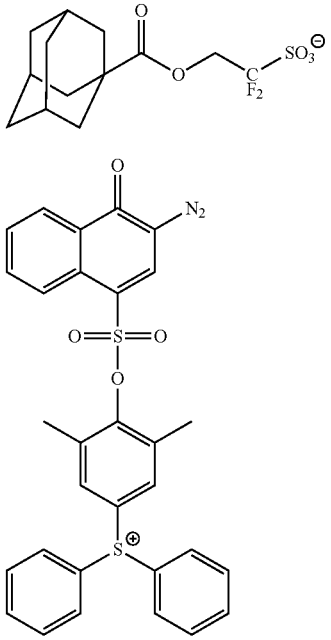

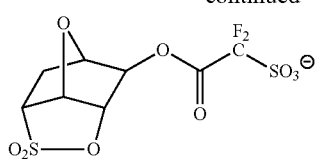
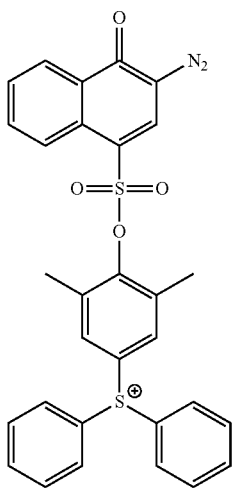
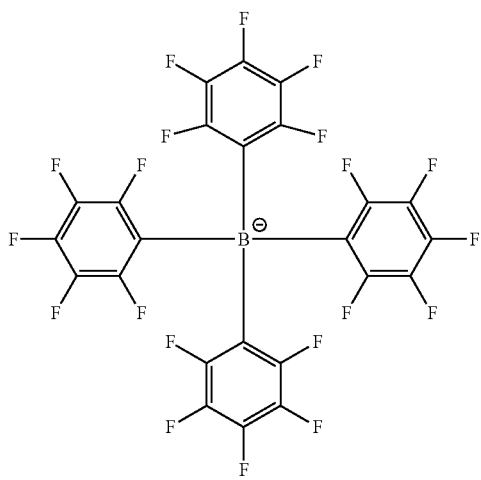
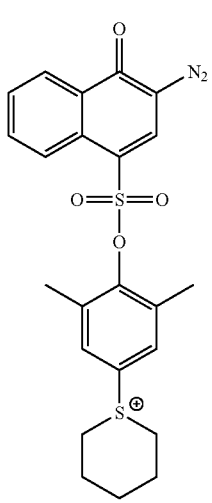

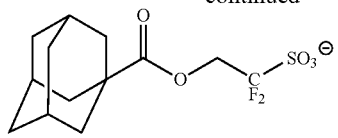
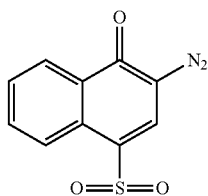

BQ-4

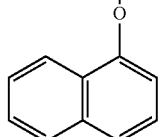

BQ-6

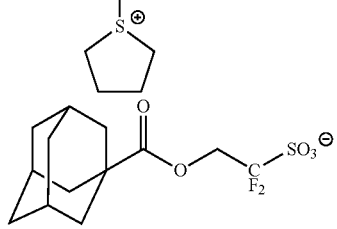
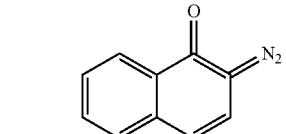

BQ-7

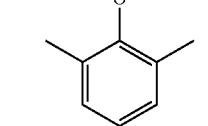
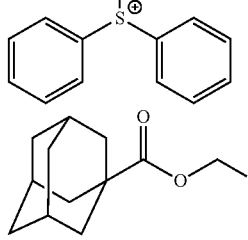

BQ-5

Polymer Synthesis Example

Polymeric compounds 1 to 4 were synthesized using the following monomers (1) to (9) which derived the structural units constituting each polymeric compound by a conventional method. With respect to the obtained compounds, the compositional ratio (the molar ratio of the respective structural units indicated in the structural formula shown below) as determined by carbon 13 nuclear magnetic resonance spectroscopy (600 MHz_13C-NMR; internal standard: tetramethylsilane), and the weight average molecular weight (Mw)

and the molecular weight dispersity (Mw/Mn) determined by the polystyrene equivalent value as measured by GPC are shown in Table 1.

[Chemical Formula 68]

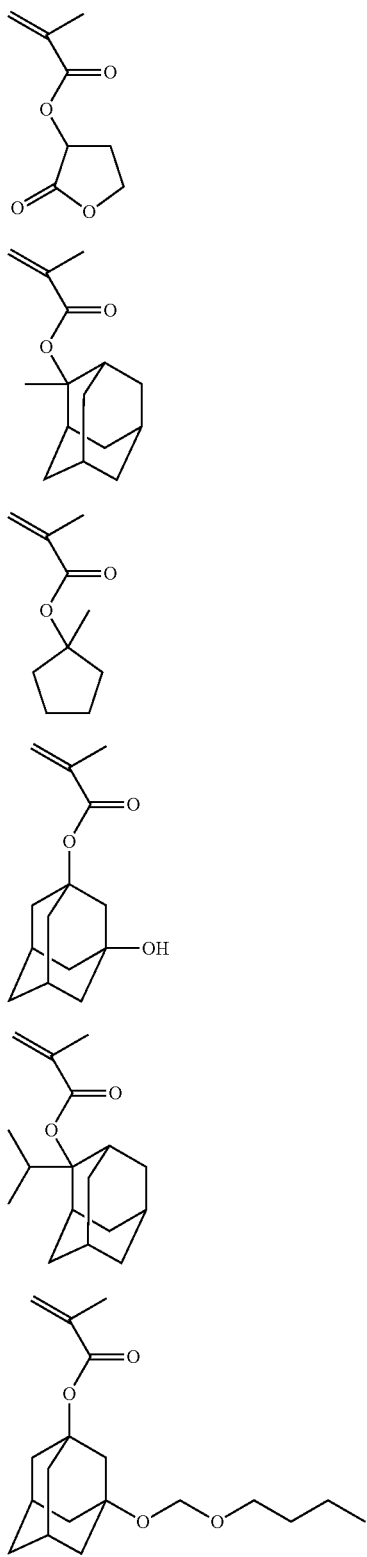

(1)
(2)
(3)
(4)
(5)
(6)

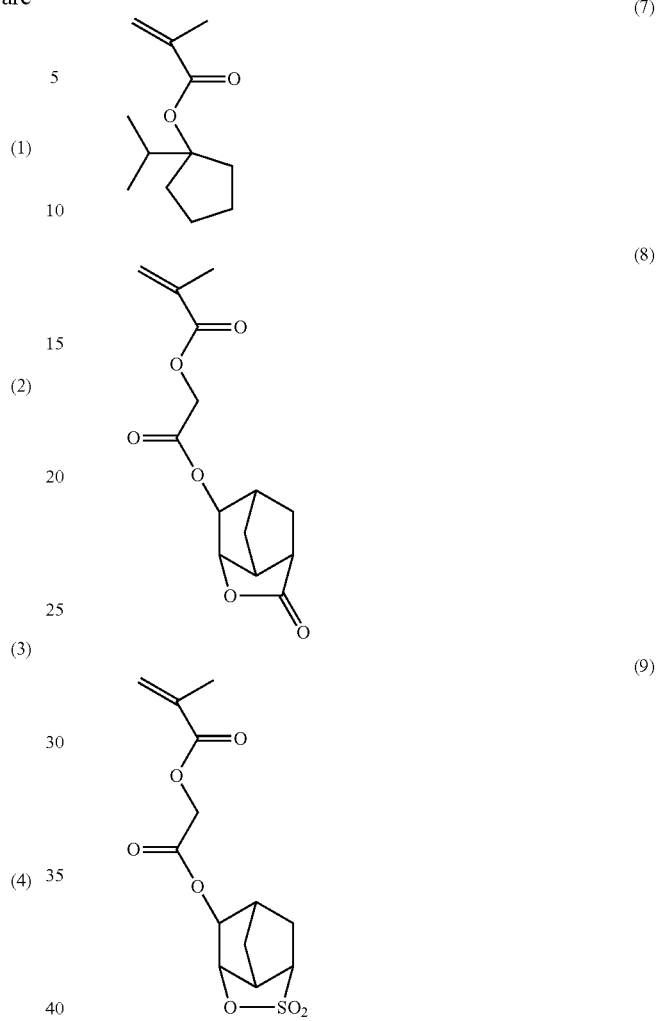

(7)
(8)
(9)

TABLE 1

| | | Polymeric compound | | | |
|---|---|---|---|---|---|
| | | 1 | 2 | 3 | 4 |
| Monomer | (1) | 46 | | | 15 |
| | (2) | 5 | | | |
| | (3) | 38 | | | |
| | (4) | 11 | | | 10 |
| | (5) | | | | 43 |
| | (6) | | | | 9 |
| | (7) | | 53 | 51 | |
| | (8) | | 47 | | 23 |
| | (9) | | | 49 | |
| Mw | | 7.2k | 7.0k | 7.2k | 7.5k |
| Mw/Mn | | 1.68 | 1.68 | 1.68 | 1.67 |

Using the obtained polymeric compounds, positive resist compositions were produced with the blend ratio shown in Table 2 below (Examples 1 to 9 and Comparative Examples 1 to 3).

TABLE 2

| | Component (A) | Component (B) | Component (D) | Component (F) | Component (S) | |
|---|---|---|---|---|---|---|
| | | | | | (S)-1 | (S)-2 |
| Example 1 | (A)-1 [100] | (BQ)-1 [14.3] | (D)-1 [4.2] | (F)-1 [3.3] | (S)-1 [10] | (S)-2 [2500] |
| Example 2 | (A)-1 [100] | (BQ)-2 [14.71] | (D)-1 [4.2] | (F)-1 [3.3] | (S)-1 [10] | (S)-2 [2500] |
| Example 3 | (A)-1 [100] | (BQ)-3 [15.15] | (D)-1 [4.2] | (F)-1 [3.3] | (S)-1 [10] | (S)-2 [2500] |
| Example 4 | (A)-1 [100] | (BQ)-4 [20.77] | (D)-1 [4.2] | (F)-1 [3.3] | (S)-1 [10] | (S)-2 [2500] |
| Example 5 | (A)-1 [100] | (BQ)-5 [13.28] | (D)-1 [4.2] | (F)-1 [3.3] | (S)-1 [10] | (S)-2 [2500] |
| Example 6 | (A)-1 [100] | (BQ)-6 [13.41] | (D)-1 [4.2] | (F)-1 [3.3] | (S)-1 [10] | (S)-2 [2500] |
| Example 7 | (A)-1 [100] | (BQ)-7 [14.71] | (D)-1 [4.2] | (F)-1 [3.3] | (S)-1 [10] | (S)-2 [2500] |
| Example 8 | (A)-2 [100] | (BQ)-2 [14.71] | (D)-1 [4.2] | (F)-1 [3.3] | (S)-1 [10] | (S)-2 [2500] |
| Example 9 | (A)-3 [100] | (BQ)-2 [14.71] | (D)-1 [4.2] | (F)-1 [3.3] | (S)-1 [10] | (S)-2 [2500] |
| Comparative Example 1 | (A)-1 [100] | (B)-1 [10] | (D)-1 [4.2] | (F)-1 [3.3] | (S)-1 [10] | (S)-2 [2500] |
| Comparative Example 2 | (A)-2 [100] | (B)-1 [10] | (D)-1 [4.2] | (F)-1 [3.3] | (S)-1 [10] | (S)-2 [2500] |
| Comparative Example 3 | (A)-3 [100] | (B)-1 [10] | (D)-1 [4.2] | (F)-1 [3.3] | (S)-1 [10] | (S)-2 [2500] |

Using the obtained polymeric compounds, negative resist compositions were produced with the blend ratio shown in Table 3 below (Examples 10 to 13 and Comparative Example 4).

TABLE 3

| | Component (A) | Component (B) | Component (D) | Component (F) | Component (S) | |
|---|---|---|---|---|---|---|
| | | | | | (S)-1 | (S)-3 |
| Example 10 | (A)-4 [100] | (BQ)-2 [10] | (D)-1 [4.2] | (F)-2 [4.0] | (S)-1 [100] | (S)-3 [2300] |
| Example 11 | (A)-4 [100] | (BQ)-5 [14.71] | (D)-1 [4.2] | (F)-2 [4.0] | (S)-1 [100] | (S)-3 [2300] |
| Example 12 | (A)-4 [100] | (BQ)-6 [13.41] | (D)-1 [4.2] | (F)-2 [4.0] | (S)-1 [100] | (S)-3 [2300] |
| Example 13 | (A)-4 [100] | (BQ)-7 [14.71] | (D)-1 [4.2] | (F)-2 [4.0] | (S)-1 [100] | (S)-3 [2300] |
| Comparative Example 4 | (A)-4 [100] | (B)-1 [10] | (D)-1 [4.2] | (F)-2 [4.0] | (S)-1 [100] | (S)-3 [2300] |

In Tables 2 and 3, the reference characters indicate the following. Further, the values in brackets [ ] indicate the amount (in terms of parts by weight) of the component added.

(A)-1 to (A)-4: the aforementioned polymeric compounds 1 to 4

(BQ)-1 to (BQ)-7: compounds BQ-1 to BQ-7 synthesized above (B)-1: compound (B)-1 shown below (D)-1 and (D)-2: compounds (D)-1 and (D)-2 shown below (F)-1: a polymeric compound (F)-1 shown below [molar ratio: l/m=77/23, Mw: 23,100, Mw/Mn: 1.78.]

(F)-2: a polymeric compound (F)-2 shown below [molar ratio: l/m=52/48, Mw: 17,500, Mw/Mn: 1.61.]

(S)-1: γ-butyrolactone (S)-2: a mixed solvent of PGMEA/PGME/cyclohexanone=45/30/25 (weight ratio)

(S)-3: a mixed solvent of PGMEA/cyclohexanone=90/10 (weight ratio)

[Chemical Formula 69]

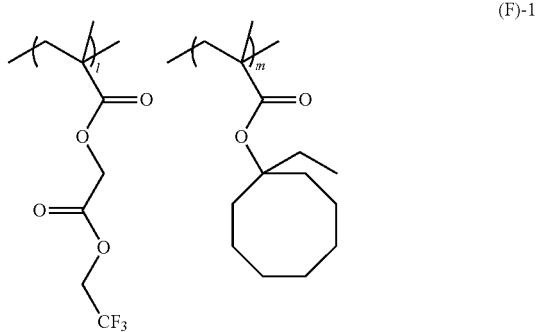

-continued

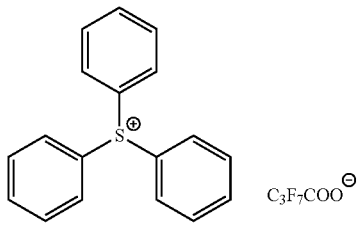

(D)-2

Formation of Positive-Tone Resist Pattern

Examples 1 to 9, Comparative Examples 1 to 3

An organic anti-reflection film composition (product name: ARC95, manufactured by Brewer Science Ltd.) was applied to an 12-inch silicon wafer using a spinner, and the composition was then baked at 205° C. for 60 seconds and dried, thereby forming an organic anti-reflection film having a film thickness of 90 nm.

Then, each of the positive resist compositions of Table 2 (Examples 1 to 9 and Comparative Examples 1 to 3) was applied to the antireflection film using a spinner, and was then prebaked (PAB) on a hotplate at 120° C. or 100° C. for 60 seconds and dried, thereby forming a resist film having a film thickness of 80 nm.

Subsequently, the resist film was selectively irradiated with an ArF excimer laser (193 nm) through a photomask (6% half tone), using an immersion lithography ArF exposure apparatus NSR-S609B (manufactured by Nikon Corporation; NA (numerical aperture)=1.07; Dipole (in/out=0.78/0.97) with Polano; immersion medium: water).

Further, a post exposure bake (PEB) was conducted at 100° C. or 90° C. for 60 seconds.

Thereafter, an alkali development was conducted for 10 seconds at 23° C. in a 2.38 wt % aqueous TMAH solution (product name: NMD-3; manufactured by Tokyo Ohka Kogyo Co., Ltd.), followed by water rinsing for 30 seconds using pure water, and drying by shaking.

As a result, in each of the examples, a 1:1 line and space pattern (LS pattern) having a line width of 50 nm and a pitch of 100 nm was formed.

<Evaluation of Positive-Tone Resist Pattern>

[Evaluation of Mask Error Factor (MEEF)]

In accordance with the same procedure as in the formation of the LS pattern, an LS pattern having a pitch of 100 nm was formed with the same exposure dose and using a mask pattern in which the target size of the line pattern was 45 to 54 nm (10 target sizes at intervals of 1 nm). The value of the mask error factor was determined as the gradient of a graph obtained by plotting the target size (nm) on the horizontal axis, and the actual size (nm) of the line pattern formed on the resist film using each mask pattern on the vertical axis. A MEEF value (gradient of the plotted line) closer to 1 indicates that a resist pattern faithful to the mask pattern was formed. The results are shown in Table 4.

[Evaluation of Line Width Roughness (LWR)]

With respect to each of the above LS patterns, the space width at 400 points in the lengthwise direction of the space were measured using a measuring scanning electron microscope (SEM) (product name: S-9380, manufactured by Hitachi High-Technologies Corporation; acceleration voltage: 300V). From the results, the value of 3 times the standard deviation s (i.e., 3s) was determined, and the average of the 3s values at 400 points was calculated as a yardstick of LWR. The results are shown in Table 4.

The smaller this 3s value is, the lower the level of roughness of the line width, indicating that a LS pattern with a uniform width was obtained.

[Evaluation of Exposure Latitude (EL Margin)]

With respect to the exposure dose with which the above LS pattern is formed, the exposure dose with which an LS pattern having a dimension of the target dimension ±5% was determined, and the EL margin (unit: %) was determined by the following formula. The results are shown in Table 4.

EL margin(%)=(|E1−E2|/Eop)×100

In the formula, E1 represents the exposure dose (mJ/cm$^2$) for forming an LS pattern having a line width of 47.5 nm, and E2 represents the exposure dose (mJ/cm$^2$) for forming an LS pattern having a line width of 52.5 nm.

The larger the value of the "EL margin", the smaller the change in the pattern size by the variation of the exposure dose.

In the calculation of EL margin, "Eop" means the optimum exposure dose (mJ/cm$^2$). The Eop was determined by a normal method.

TABLE 4

| | PAB/PEB (° C.) each 60 sec | EL margin | LWR (nm) | MEEF |
|---|---|---|---|---|
| Example 1 | 120/110 | 7.20% | 6.15 | 3.33 |
| Example 2 | 120/110 | 8.00% | 5.68 | 3.07 |
| Example 3 | 120/110 | 8.10% | 5.72 | 3.02 |
| Example 4 | 120/110 | 7.60% | 6.09 | 3.21 |
| Example 5 | 120/110 | 8.50% | 5.81 | 3.18 |
| Example 6 | 120/110 | 8.40% | 6.03 | 3.13 |
| Example 7 | 120/110 | 7.70% | 6.11 | 3.15 |
| Example 8 | 120/110 | 7.80% | 5.22 | 2.95 |
| Example 9 | 120/110 | 8.30% | 5.31 | 2.99 |
| Comparative Example 1 | 100/90 | 6.90% | 6.31 | 3.45 |
| Comparative Example 2 | 100/90 | 6.90% | 6.25 | 3.37 |
| Comparative Example 3 | 100/90 | 7.10% | 6.2 | 3.36 |

From the results shown above, it was confirmed that the resist compositions of Examples 1 to 9 exhibited excellent lithography properties (such as MEEF, LWR and EL margin), as compared to the resist compositions of Comparative Examples 1 to 3.

Formation of Negative-Tone Resist Pattern

Examples 10 to 13, Comparative Example 4

An organic anti-reflection film composition (product name: ARC29A, manufactured by Brewer Science Ltd.) was applied to an 12-inch silicon wafer using a spinner, and the composition was then baked at 205° C. for 60 seconds, thereby forming an organic anti-reflection film having a film thickness of 89 nm.

Then, each of the negative resist compositions of Table 3 was applied to the antireflection film using a spinner, and was then prebaked (PAB) on a hotplate at 100° C., 105° C. or 120° C. for 60 seconds and dried, thereby forming a resist film having a film thickness of 100 nm.

Subsequently, the resist film was selectively irradiated with an ArF excimer laser (193 nm) through a photomask (6% half tone), using an immersion lithography ArF exposure apparatus NSR-S609B (manufactured by Nikon Corporation; NA (numerical aperture)=1.07; Dipole (in/out=0.78/0.97) with Polano; immersion medium: water).

Further, a post exposure bake (PEB) was conducted at 85° C. or 80° C. for 60 seconds.

Next, a solvent development was conducted at 23° C. for 13 seconds using 2-heptanone, followed by drying by shaking.

As a result, in each of the examples, a contact hole pattern in which holes having a diameter of 55 nm were equally spaced (pitch: 110 nm) was formed (hereafter, this contact hole pattern is referred to as "CH pattern").

<Evaluation of Negative-Tone Resist Pattern>
[Evaluation of Exposure Latitude (EL Margin)]

The exposure does with which each CH pattern could be formed with a hole diameter of 55 nm±5% (i.e., 53 nm or 58 nm) was determined, and EL margin (unit: %) was determined by the following formula. The results are shown in Table 5.

EL margin(%)=(|E1−E2|/Eop)×100

E1: Exposure dose (mJ/cm$^2$) with which a CH pattern having a hole diameter of 53 nm was formed
E2: Exposure dose (mJ/cm$^2$) with which a CH pattern having a hole diameter of 58 nm was formed The larger the value of the "EL margin", the smaller the change in the pattern size by the variation of the exposure dose.

In the calculation of EL margin, "Eop" means the optimum exposure dose (mJ/cm$^2$). The Eop was determined by a normal method.

[Evaluation of Circularity]

With respect to each CH pattern obtained above, 25 holes in the CH pattern were observed from the upper side thereof using a measuring scanning electron microscope (SEM) (product name: S-9380, manufactured by Hitachi High-Technologies Corporation; acceleration voltage: 300V), and the distance from the center of each hole to the outer periphery of the hole was measured in 24 directions. From the results, the value of 3 times the standard deviation σ (i.e., 3σ) was determined. The results are shown in Table 5.

The smaller this 3σ value is, the higher the level of circularity of the holes.

[In-Plane Uniformity (CDU) of Pattern Size]

With respect to each CH pattern obtained above, 100 holes in the CH pattern were observed from the upper side thereof using a measuring scanning electron microscope (SEM) (product name: S-9380, manufactured by Hitachi High-Technologies Corporation; acceleration voltage: 300V), and the hole diameter (nm) of each hole was measured. From the results, the value of 3 times the standard deviation σ (i.e., 3σ) was determined. The results are indicated "CDU" in Table 5.

The smaller the thus determined 3σ value is, the higher the level of the dimension uniformity (CD uniformity) of the plurality of holes formed in the resist film.

TABLE 5

|  | PAB/PEB (° C.) each 60 sec | EL margin | Circularity | CDU |
|---|---|---|---|---|
| Example 10 | 120/85 | 6.50% | 2.72 | 8.93 |
| Example 11 | 120/85 | 5.70% | 2.86 | 8.35 |
| Example 12 | 120/85 | 6.10% | 2.88 | 9.11 |
| Example 13 | 120/85 | 5.90% | 2.81 | 9.25 |
| Comparative Example 4 | 120/85 | 4.70% | 3.18 | 10.07 |

From the results shown above, it was confirmed that the resist compositions of Examples 10 to 13 exhibited excellent lithography properties such as EL margin, depth of focus, circularity and CDU, as compared to the resist composition of Comparative Example 4.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A compound represented by general formula (b1) shown below:

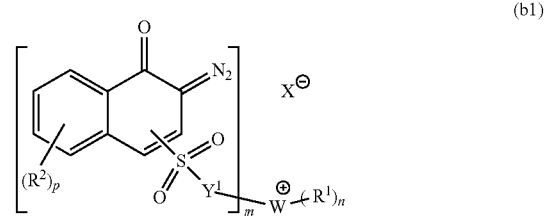

(b1)

wherein Y$^1$ represents a divalent linking group; W represents S, Se or I; R$^1$ represents a hydrocarbon group with or without a substituent; R$^2$ represents an alkyl group of 1 to 5 carbon atoms or an alkoxy group of 1 to 5 carbon atoms; when W represents I, m+n=2, and when W represents S or Se, m+n=3, provided that m≥1 and n≥0; p represents an integer of 0 to 5; and X$^−$ represents a counteranion.

2. The compound according to claim 1, wherein Y$^1$ is represented by any one of general formulae (Y-lg-1) to (Y-lg-14) shown below:

(Y-lg-1)

(Y-lg-2)

(Y-lg-3)

(Y-lg-4)

(Y-lg-5)

-continued (Y-lg-6) 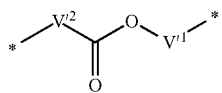

(Y-lg-7) 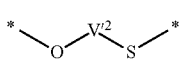

(Y-lg-8) 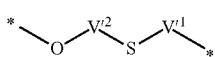

(Y-lg-9) 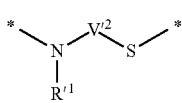

(Y-lg-10) 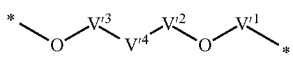

(Y-lg-11) 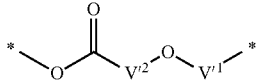

(Y-lg-12) 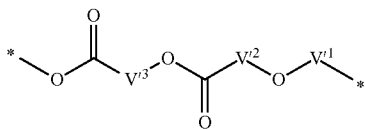

(Y-lg-13) 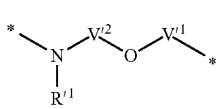

(Y-lg-14) 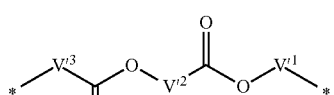

wherein $V^{r1}$ to $V^{r3}$ each independently represents a divalent hydrocarbon group with or without a substituent; $V^{r4}$ represents a divalent hydrocarbon group with or without a substituent; $R^{r1}$ a hydrogen atom or an alkyl group of 1 to 5 carbon atoms; and * represents a valence bond, provided that The valence bond on the left-hand side is bonded to $SO_2$ in general formula (b1), and the valence bond on the right-hand side is bonded to $W^+$ in general formula (b1).

3. The compound according to claim 2, wherein $V^{r1}$ represents a divalent aromatic hydrocarbon group with or without a substituent.

4. The compound according to claim 2, wherein $V^{r1}$ represents an arylene group or an aralkylene group.

5. The compound according to claim 2, wherein $V^{r2}$ and $V^{r3}$ each independently represents an alkylene group with or without a substituent.

6. The compound according to claim 2, wherein $V^{r2}$ and $V^{r3}$ each independently represents a chain-like alkylene group with or without a substituent.

7. The compound according to claim 2, wherein $V^{r4}$ represents an alkylene group of 1 to 5 carbon atoms.

8. The compound according to claim 1, wherein the cation moiety is represented by any one of formulae shown below:

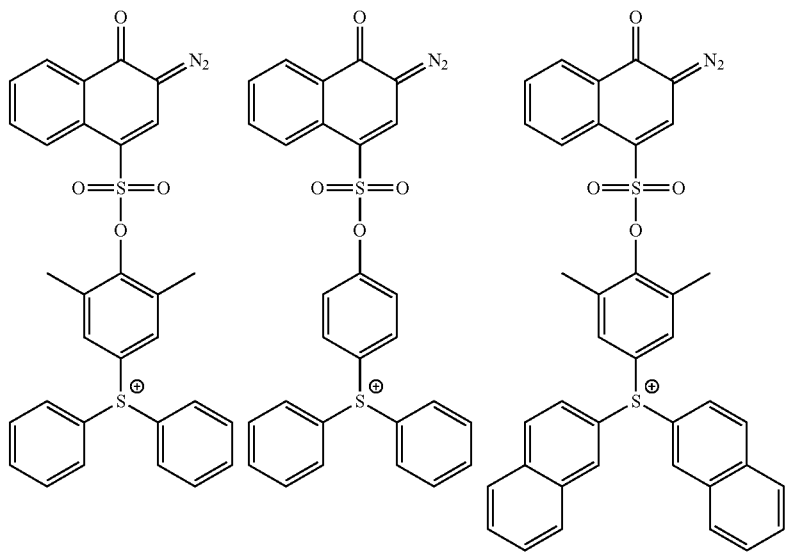

135
136
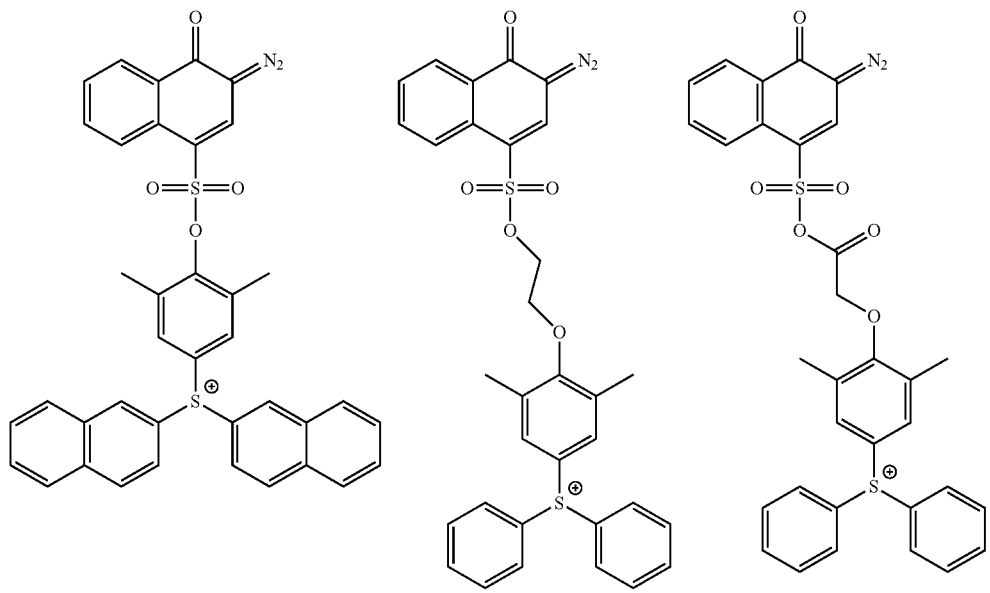
-continued
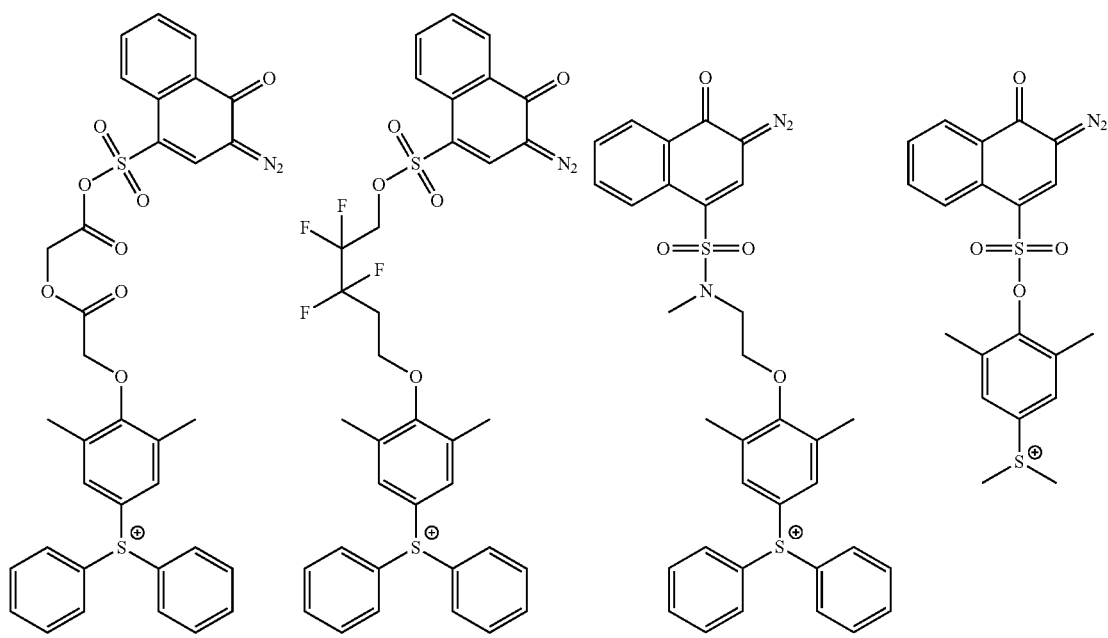
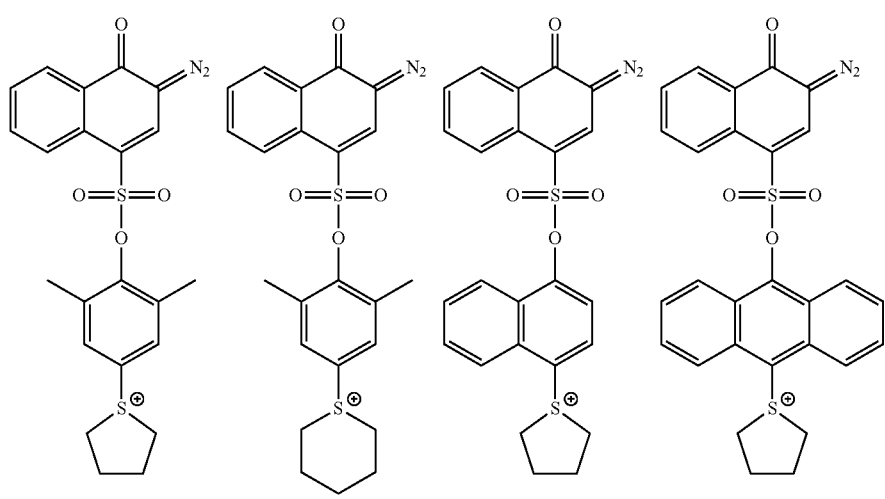

137                                           138
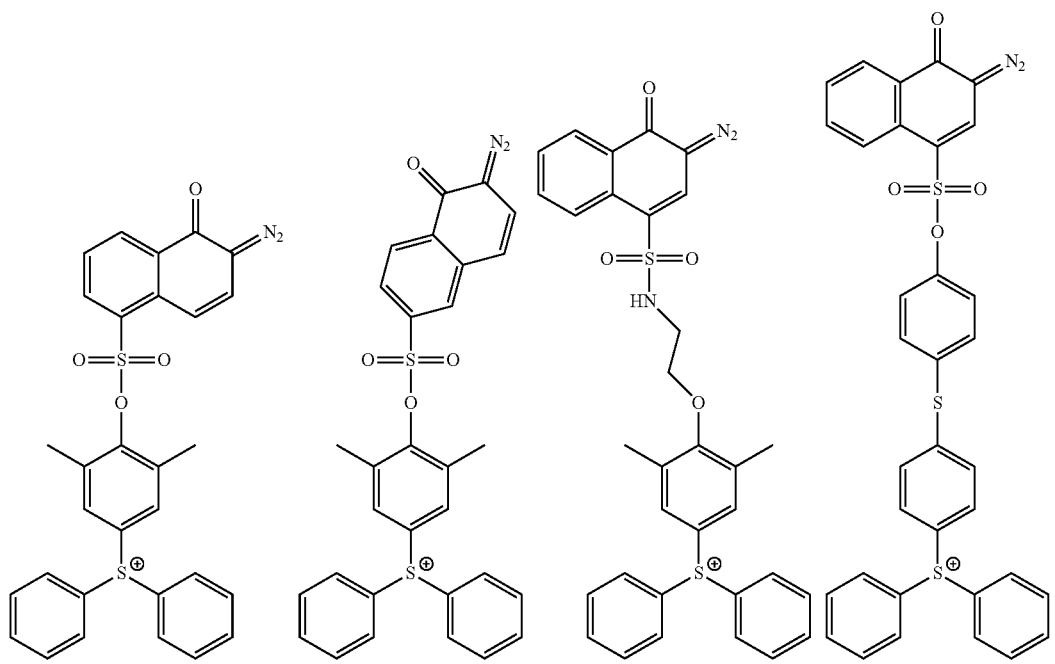
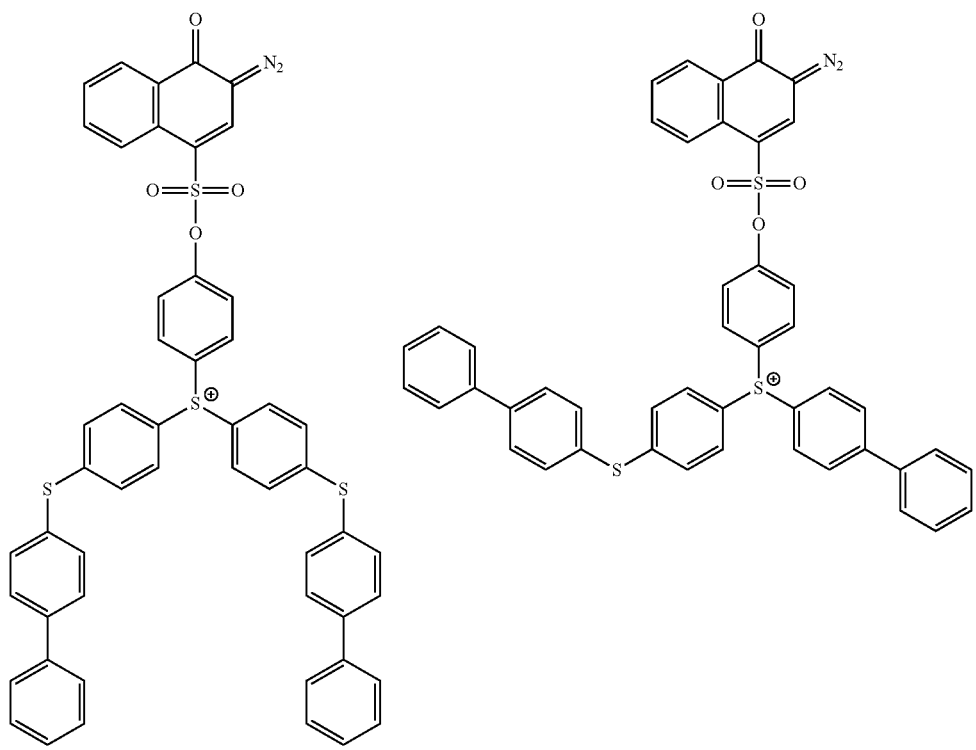
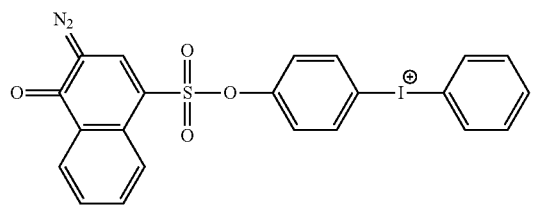

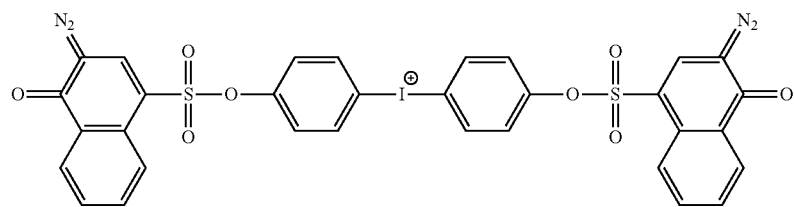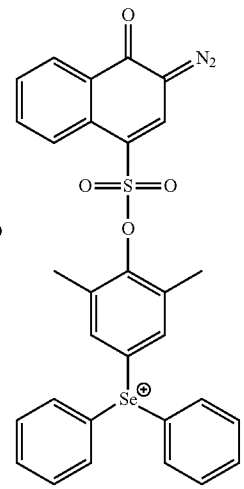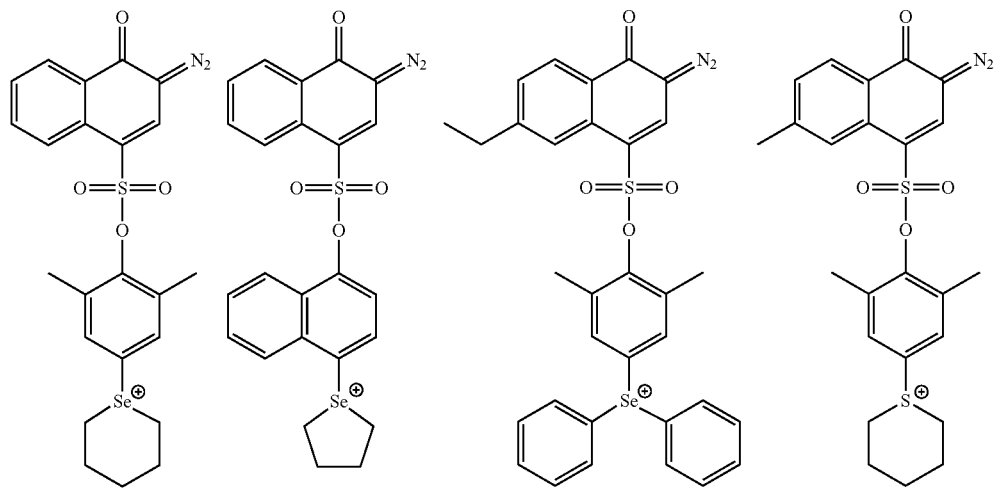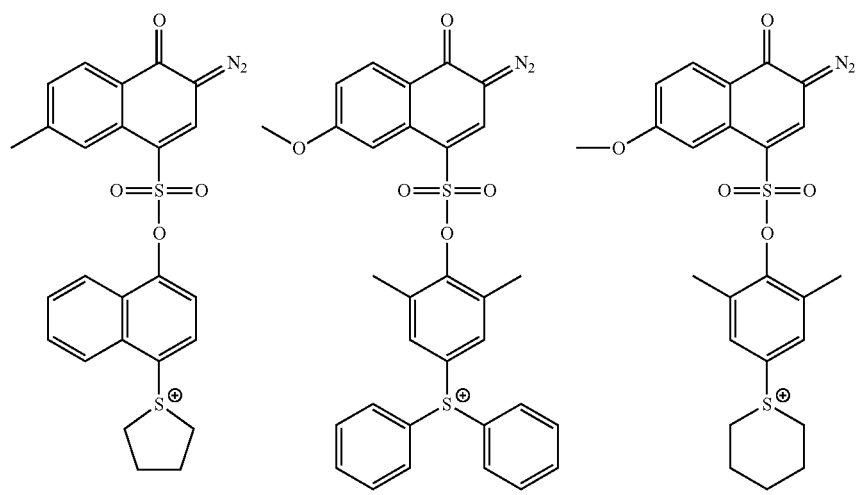

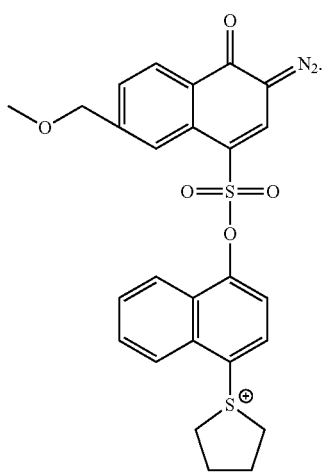

9. The compound according to claim 1, wherein X⁻ represents a sulfonate anion, a carboxylate anion, an imide anion, a methide anion, a carboanion, a borate anion, a halogen anion, a phosphate anion, an antimonate anion and an arsenate anion.

10. A resist composition comprising:
a base component (A) which exhibits changed solubility in an alkali developing solution under action of acid, and
an acid generator component (B) which generates acid upon exposure, the acid generator component (B) comprising an acid generator (B1) comprising a compound represented by general formula (b1-1) shown below:

(b1-1)
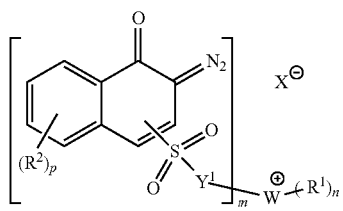

wherein Y¹ represents a divalent linking group; W represents S, Se or I; R¹ represents a hydrocarbon group with or without a substituent; R² represents an alkyl group of 1 to 5 carbon atoms or an alkoxy group of 1 to 5 carbon atoms; when W represents I, m+n=2, and when W represents S or Se, m+n=3, provided that m≥1 and n≥0; p represents an integer of 0 to 5; and X⁻ represents a counteranion.

11. The resist composition according to claim 10, wherein Y¹ is represented by any one of general formulae (Y-lg-1) to (Y-lg-14) shown below:

(Y-lg-1)
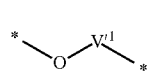

(Y-lg-2)
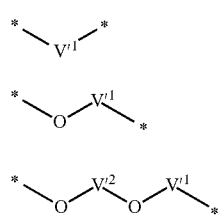

(Y-lg-3)
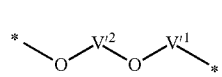

-continued (Y-lg-4)
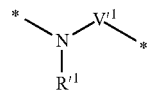

(Y-lg-5)
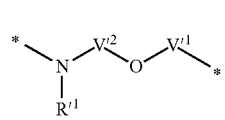

(Y-lg-6)
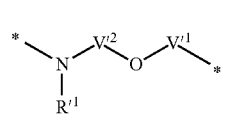

(Y-lg-7)
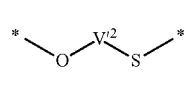

(Y-lg-8)
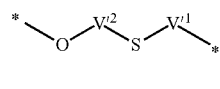

(Y-lg-9)
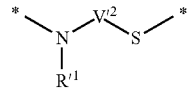

(Y-lg-10)
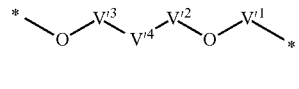

(Y-lg-11)
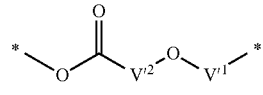

(Y-lg-12)
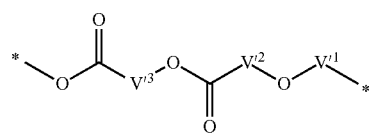

(Y-lg-13)
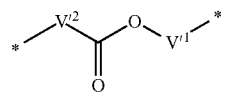

-continued

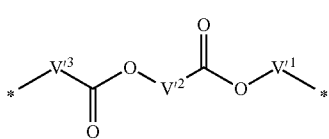
(Y-lg-14)

wherein $V'^1$ to $V'^3$ each independently represents a divalent hydrocarbon group with or without a substituent; $V'^4$ represents a divalent hydrocarbon group with or without a substituent; a hydrogen atom or an alkyl group of 1 to 5 carbon atoms; and * represents a valence bond, provided that The valence bond on the left-hand side is bonded to $SO_2$ in general formula (b1), and the valence bond on the right-hand side is bonded to W in general formula (b1).

12. The resist composition according to claim 11, wherein $V'^1$ represents a divalent aromatic hydrocarbon group with or without a substituent.

13. The resist composition according to claim 11, wherein $V'^1$ represents an arylene group or an aralkylene group.

14. The resist composition according to claim 11, wherein $V'^2$ and $V'^3$ each independently represents an alkylene group with or without a substituent.

15. The resist composition according to claim 11, wherein $V'^2$ and $V'^3$ each independently represents a chain-like alkylene group with or without a substituent.

16. The resist composition according to claim 11, wherein $V'^4$ represents an alkylene group of 1 to 5 carbon atoms.

17. The resist composition according to claim 10, wherein the cation moiety is represented by any one of formulae shown below:

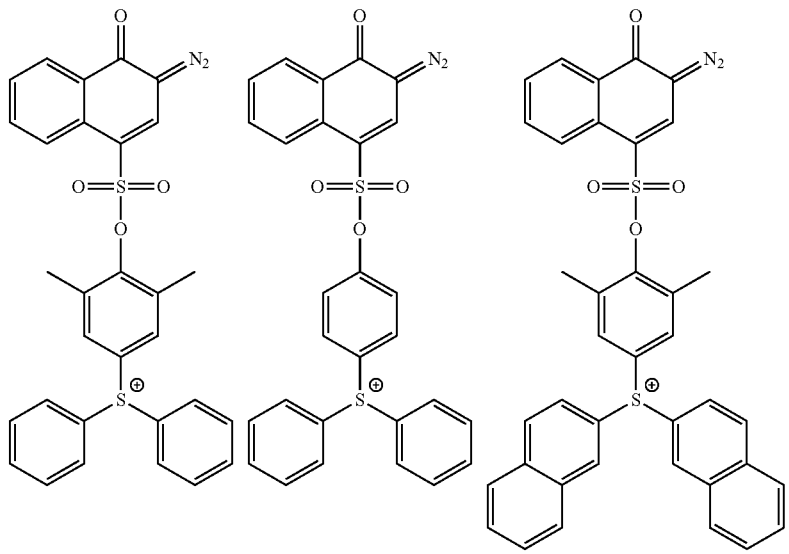

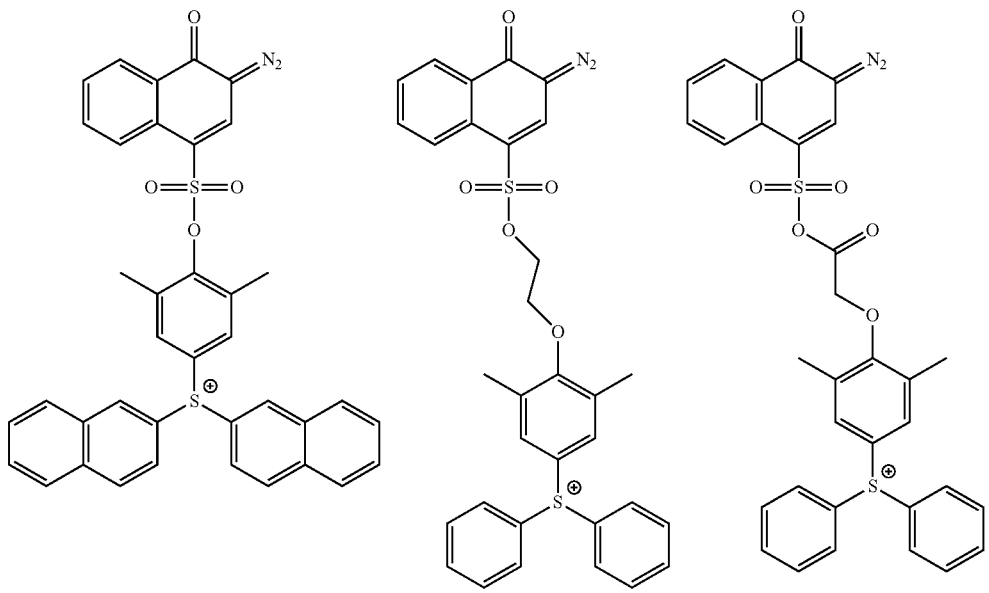

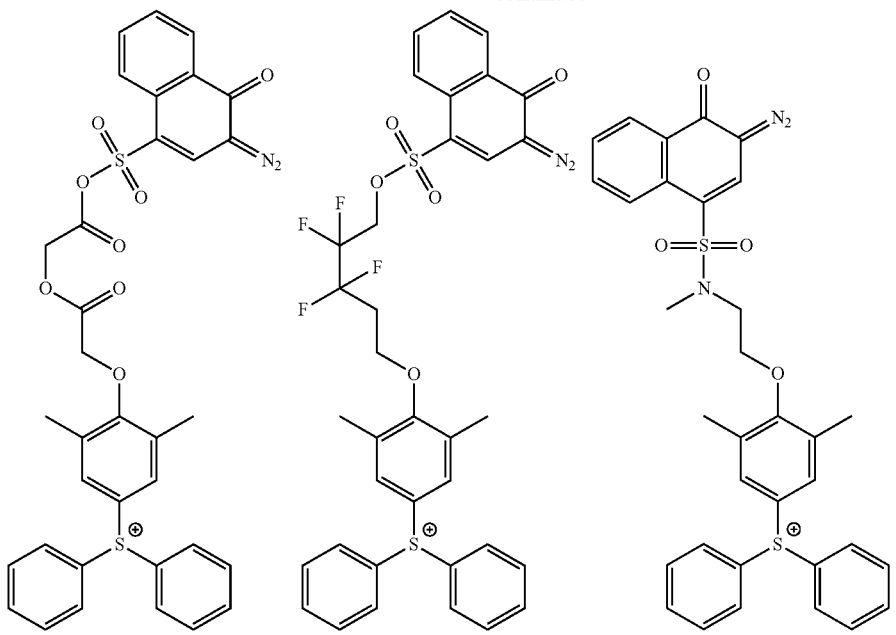
-continued
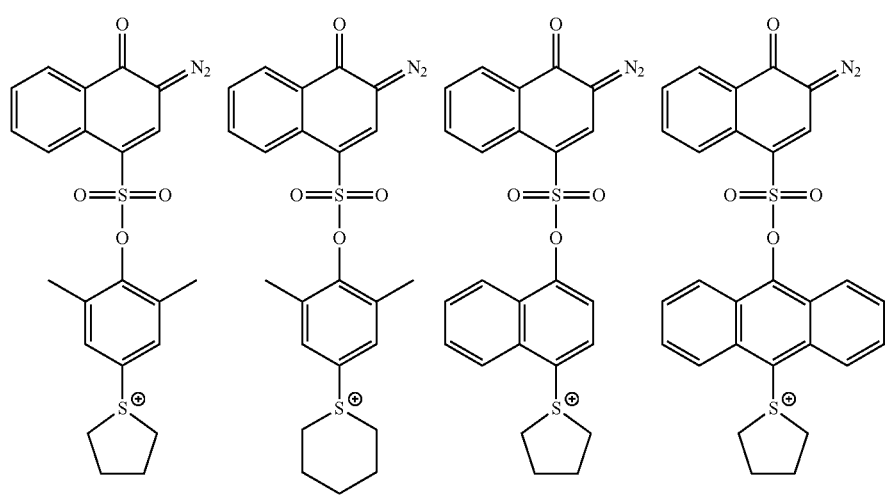

147
148
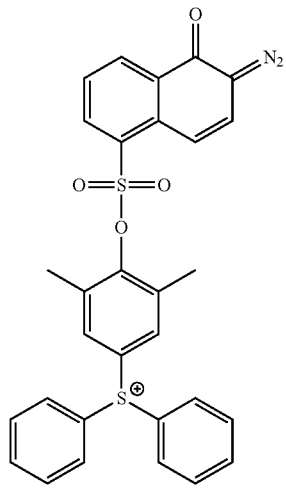
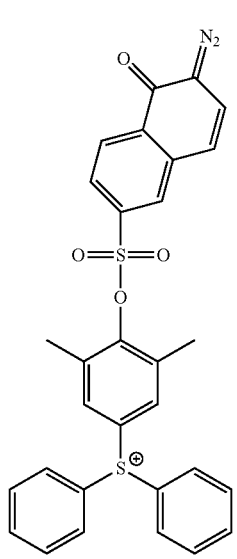
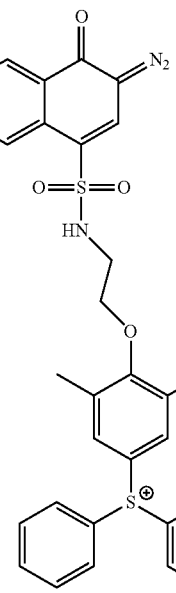
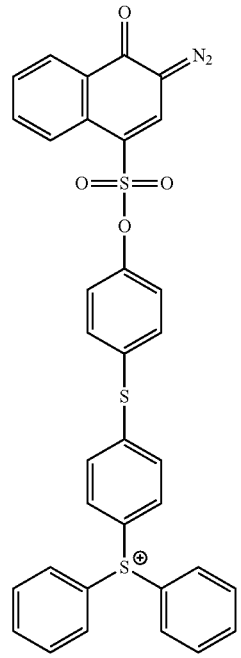
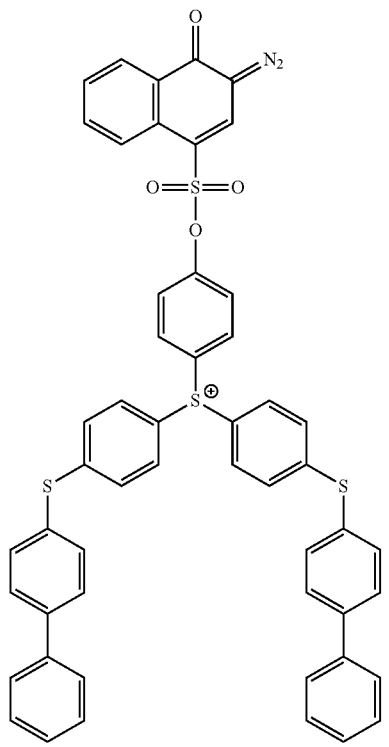
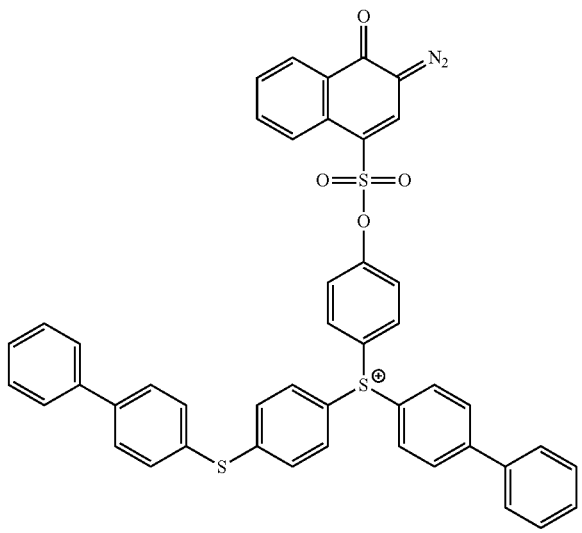
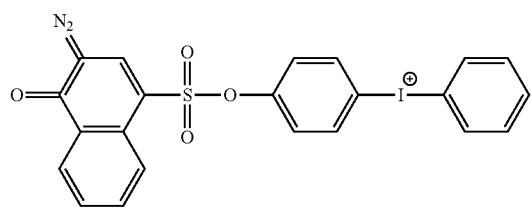

149
150
-continued
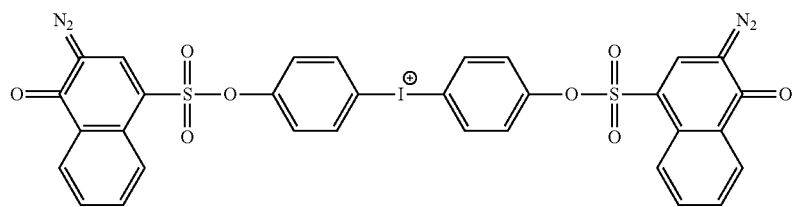
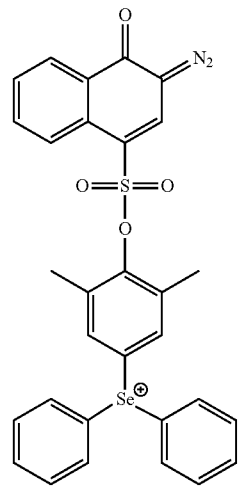
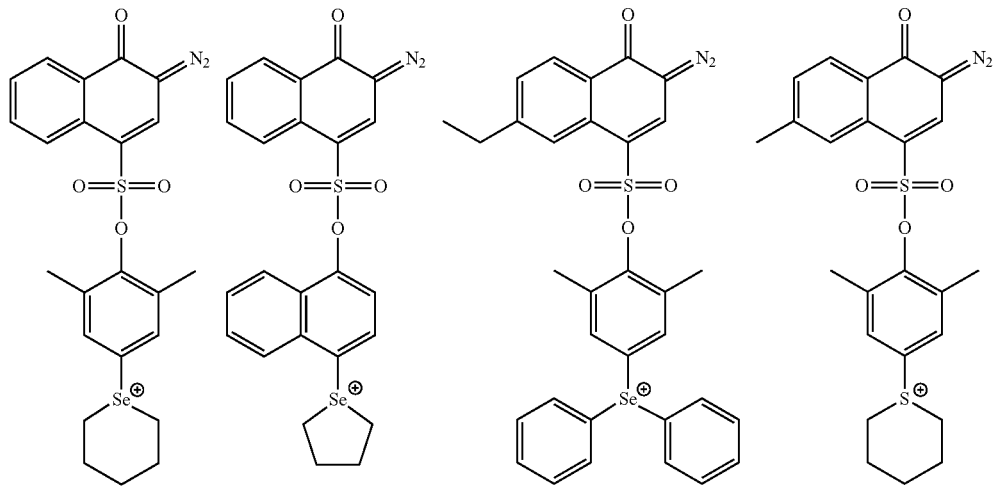
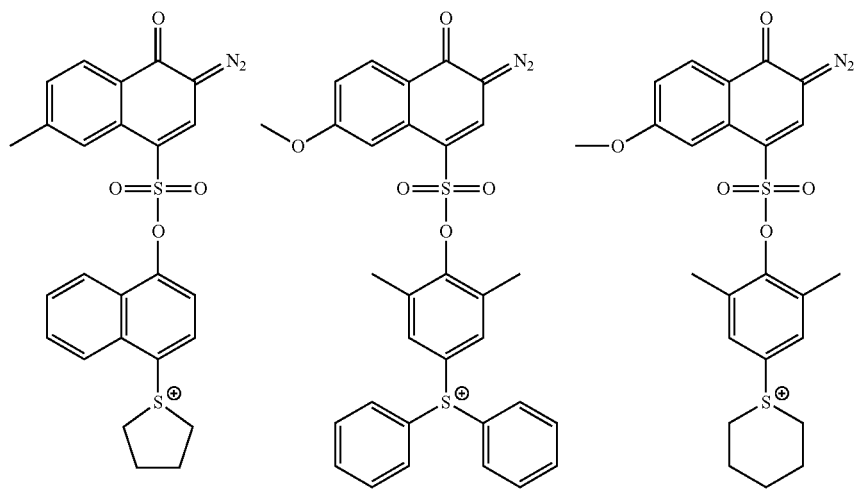

-continued

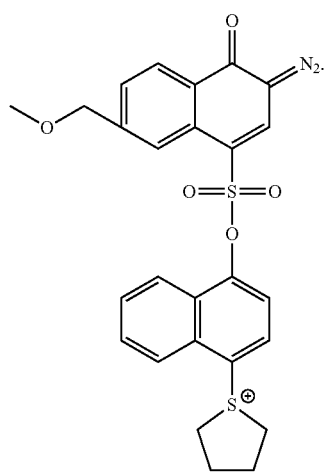

18. The resist composition according to claim 10, wherein $X^-$ represents a sulfonate anion, a carboxylate anion, an imide anion, a methide anion, a carboanion, a borate anion, a halogen anion, a phosphate anion, an antimonate anion and an arsenate anion.

19. A method of forming a resist pattern, comprising:
applying the resist composition according to claim 10 to form a resist film on a substrate,
subjecting the resist film to patterned exposure, and
subjecting the resist film to developing to form a resist pattern.

* * * * *